US009409879B2

(12) United States Patent
Davioud-Charvet et al.

(10) Patent No.: US 9,409,879 B2
(45) Date of Patent: Aug. 9, 2016

(54) TOTAL SYNTHESIS OF REDOX-ACTIVE 1.4-NAPHTHOQUINONES AND THEIR METABOLITES AND THEIR THERAPEUTIC USE AS ANTIMALARIAL AND SCHISTOMICIDAL AGENTS

(75) Inventors: Elisabeth Davioud-Charvet, Strasbourg (FR); Don Antoine Lanfranchi, Sarrola Carcopino (FR); Laure Johann, Bitche (FR); David Lee Williams, Oak Park, IL (US); Elena Cesar Rodo, Strasbourg (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/007,172

(22) PCT Filed: Mar. 29, 2012

(86) PCT No.: PCT/EP2012/055741
§ 371 (c)(1),
(2), (4) Date: Nov. 29, 2013

(87) PCT Pub. No.: WO2012/131010
PCT Pub. Date: Oct. 4, 2012

(65) Prior Publication Data
US 2014/0121238 A1 May 1, 2014

(30) Foreign Application Priority Data

Mar. 29, 2011 (EP) .................................... 11305346

(51) Int. Cl.
*A61K 31/47* (2006.01)
*C07D 311/86* (2006.01)
*A61K 31/352* (2006.01)
*C07D 213/44* (2006.01)
*C07D 215/20* (2006.01)
*C07D 311/78* (2006.01)
*C07D 311/82* (2006.01)
*C07C 46/00* (2006.01)
*C07C 49/84* (2006.01)
*C07C 50/24* (2006.01)
*C07C 50/32* (2006.01)
*C07D 213/50* (2006.01)
*C07D 215/24* (2006.01)

(52) U.S. Cl.
CPC ............ *C07D 311/86* (2013.01); *A61K 31/352* (2013.01); *A61K 31/47* (2013.01); *C07C 46/00* (2013.01); *C07C 49/84* (2013.01); *C07C 50/24* (2013.01); *C07C 50/32* (2013.01); *C07D 213/44* (2013.01); *C07D 213/50* (2013.01); *C07D 215/20* (2013.01); *C07D 215/24* (2013.01); *C07D 311/78* (2013.01); *C07D 311/82* (2013.01)

(58) Field of Classification Search
None
See application file for complete search history.

(56) References Cited

FOREIGN PATENT DOCUMENTS

| EP | 2269996 A1 | 1/2011 |
| WO | 2009118327 A1 | 10/2009 |
| WO | WO 2009118327 A1 * | 10/2009 |

OTHER PUBLICATIONS

Bachman et al., "Compounds of Pharmaceutical Interest from 4-Methoxy-1-Naphthylamine", 1946, pp. 454-462, XP-002638959.
Drake et al., "Quinolinequinones. I. Quinones and Hydroquinones Related to Pentaquine", Contribution from the Department of Chemistry, University of Maryland, 1951, vol. 73, pp. 544-550, XP-002638960.
Nasr et al., "Synthesis of Benzo-Benzothiopyranoquinolines (Pyridobenzothioxanthones) as Possible Schistosomicidal and Antitumor Agents", Pharmazie, 1978, vol. 33, H. 7, pp. 424-426, XP002638958.
Ohkawa et al., "Dual Inhibitors of Thromboxane A2 Synthase and 5-Lipoxygenase with Scavenging Activity of Active Oxygen Species. Synthesis of a Novel Series of (3-Pyridylmethyl)benzoquinone Derivatives", Journal of Medicinal Chemistry, 1991, vol. 34, No. 1, XP002638952.
Waske et al., "Photoacylations of 2-substituted 1,4-naphthoquinones: a concise access to biologically active quinonoid compounds", Tetrahedron Letters, 2006, vol. 47, pp. 1329-1332, XP25003467.
International Search Report, dated May 8, 2012, from corresponding PCT application.
Akoachere et al., "In Vitro Assessment of Methylene Blue on Chloroquine-Sensitive and -Resistant Plasmodium falciparum Strains Reveals Synergistic Action with Artemisinins", Antimicrobial Agents and Chemotherapy, 2005, vol. 49, No. 11, pp. 4592-4597.
Anstey et al., "Elevated levels of methaemoglobin in Tanzanian children with severe and uncomplicated malaria", Transactions of the Royal Society of Tropical Medicine and Hygiene, 1996, vol. 90, pp. 147-151.
Bachu et al., "Synthesis of a C8 oxygenated pyranonaphthoquinone: a useful precursor to dimeric pyranonaphthoquinones", Tetrahedron, 2008, vol. 64, pp. 3343-3350.
Bauer et al., "A Fluoro-Analogue of the Menadione Derivative M5 is a Suicide Substrate of Human Glutathione Reductase. Crystal Structure of the Alkylated Enzyme", Fluorine-Based Suicide Substrate of Glutathione Reductase, pp. S1-S12. J Amer Chem Soc 2006.
Bauer et al., "A Fluoro Analogue of the Menadione Derivative 6-[2'-(3'-Methyl)-1',4'-naphthoquinolyl]hexanoic Acid Is a Suicide Substrate of Glutathione Reductase. Crystal Structure of the Alkylated Human Enzyme", Journal of American Chemical Society, 2006, vol. 128, pp. 10784-10794.
Bernadou et al., "Biomimetic Chemical Catalysts in the Oxidative Activation of Drugs", Adv. Synth. Catal., 2004, vol. 346, pp. 171-184.

(Continued)

*Primary Examiner* — Heidi Reese
(74) *Attorney, Agent, or Firm* — Young & thompson

(57) ABSTRACT

Naphthoquinones, azanaphthoquinones and benxanthones, their process of synthesis and methods of their use as antimalarial or antischistosomal agents.

12 Claims, 12 Drawing Sheets

(56) References Cited

OTHER PUBLICATIONS

Figure 1:
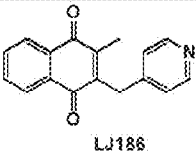
Figure 1:
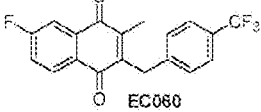
Figure 1:
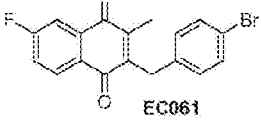
Figure 1:
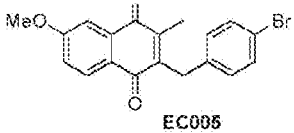
Figure 1:
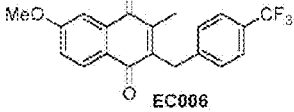
Figure 1:
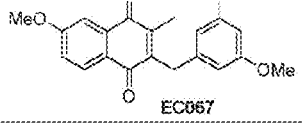
Figure 1:
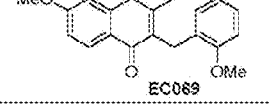
Figure 1:
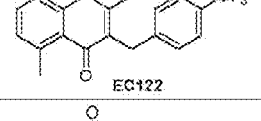
Figure 1:
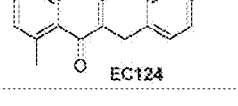
Figure 1:
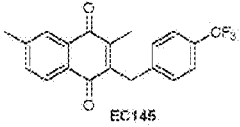
Figure 1:
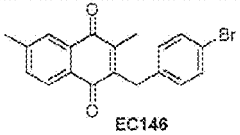
Figure 1:
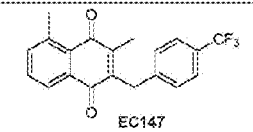
Figure 1:
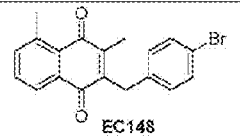
Figure 1:
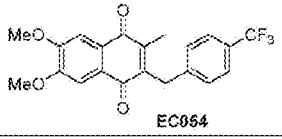
Figure 1:
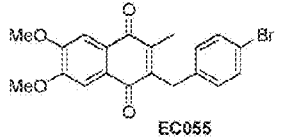
Figure 1:
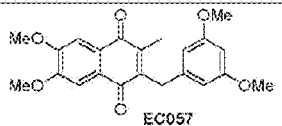
Figure 1:
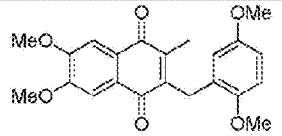
Figure 1:
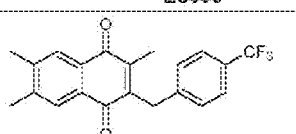
Figure 1:
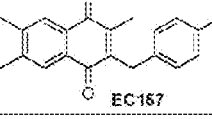
Figure 1:
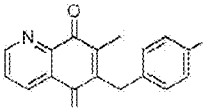
Figure 1:
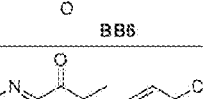
Figure 1:
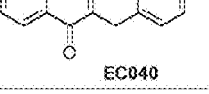
Figure 1:
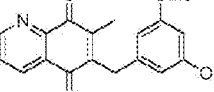
Figure 1:
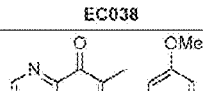
Figure 1:
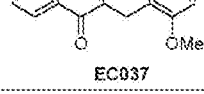
Figure 1:
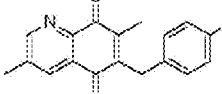
Figure 1:
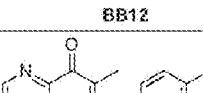
Figure 1:
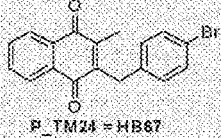
Figure 1:
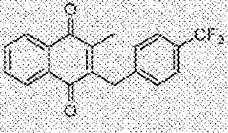
Figure 1:
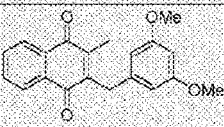
Figure 1:
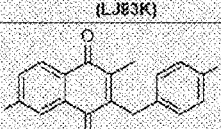
Figure 1:
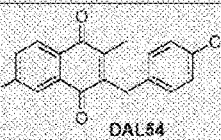
Figure 1:
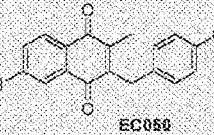
Figure 1:
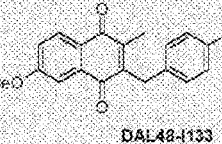
Figure 1:
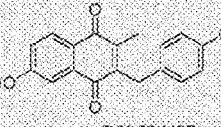
Figure 1:
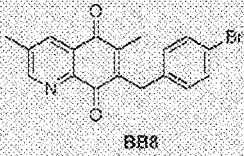
Figure 1:
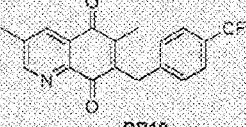
Figure 1:
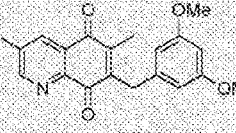
Figure 1:
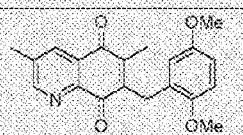
Figure 1:
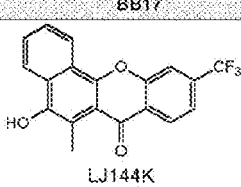
Figure 1:
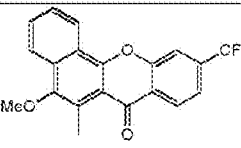
Figure 1:
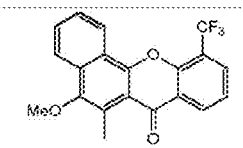
Figure 1:
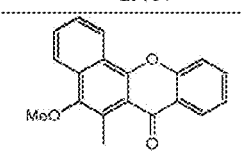

Biot et al., "5-Substituted Tetrazoles as Bioisosteres of Carboxylic Acids. Bioisosterism and Mechanistic Studies on Glutathione Reductase Inhibitors as Antimalarials", Journal of Medicinal Chemistry. 2004, vol. 47, No. 24, pp. 5972-5983.
Cohen et al., "Complex Formation between Chloroquine and Ferrihaemic Acid in vitro, and its effect on the Antimalarial Action of Chloroquine", Nature, 1964, vol. 202, pp. 805-806.
Davioud-Charvet et al., "A Prodrug Form of a Plasmodium falciparum Glutathione Reductase Inhibitor Conjugated with a 4-Anilinoquinoline", Journal of Medicinal Chemistry, 2001, vol. 44, No. 24, pp. 4268-4276.
Desjardins et al., "Quantitative Assessment of Antimalarial Activity In Vitro by a Semiautomated Microdilution Technique", Antimicrobial Agents and Chemotherapy, 1979, vol. 16, No. 6, pp. 710-718.
Dorn et al., "Malarial haemozoin/$\beta$-haematin supports haem polymerization in the absence of protein", Letters to Nature, 1995, vol. 374, pp. 269-271.
Egan, Timothy J., "Interactions of quinoline antimalarials with hematin in solution", 2006, vol. 100, pp. 916-926.
Friebolin et al., "Antimalarial Dual Drugs Based on Potent Inhibitors of Glutathione Reductase from Plasmodium falciparum", Journal of Medicinal Chemistry, 2008, vol. 51, No. 5, pp. 1260-1277.
Friebolin et al., "Antimalarial Dual Drugs Based on Potent Inhibitors of Glutathione Reductase from Plasmodium falciparum", Supporting Information, Potent Antimalarial 1,4-Naphthoquinone Derivatives, 2008, pp. S1-S6.
Goldberg et al., "The Pathway of Hemoglobin Degradation in Malaria Parasites", Parasitology Today, 1992, vol. 8, No. 8, pp. 280-283.
Jambou et al., "Resistance of Plasmodium falciparum field isolates to in-vitro artemether and point mutations of the SERCA-type PfATPase6", Lancet, 2005, vol. 366, pp. 1960-1963.
Kanzok et al., "Substitution of the Thioredoxin System for Glutathione Reductase in *Drosophila melanogaster*", Science, 2001, vol. 291, pp. 643-646.
Krauth-Siegel et al., "Dithiol Proteins as Guardians of the Intracellular Redox Milieu in Parasites: Old and New Drug Targets in Trypanosomes and Malaria-Causing Plasmodia", Angewandte Chem. Int. Ed., 2005, vol. 44, pp. 690-715.
Liard et al., "A New Synthesis of $\alpha$-Tetralones", Tetrahedron Letters, 1997, vol. 38, No. 10, pp. 1759-1762.
Lim et al., "Decreased In Vitro Susceptibility of Plasmodium falciparum Isolates to Artesunate, Mefloquine, Chloroquine, and Quinine in Cambodia from 2001 to 2007", Antimicrobial Agents and Chemotherapy, 2010, vol. 54, No. 5, pp. 2135-2142.
Meierjohann et al., "Regulation of intracellular glutathione levels in erythrocytes infected with chloroquine-sensitive and chloroquine-resistant Plasmodium falciparum", Biochem. J., 2002, vol. 368, pp. 761-768.
Meissner et al., "Methylene blue for malaria in Africa: results from a dose-finding study in combination with chloroquine", Malaria Journal, 2006, vol. 5:84, http://www.malariajournal.com/content/5/1/84.
Melman et al., "Reduced Susceptibility to Praziquantel among Naturally Occurring Kenyan Isolates of Schistosoma Mansoni", Plos Neglected Tropical Diseases, 2009, vol. 3, Issue 8, e504, pp. 1-10.
Minami et al., "Reduction of o-Acylphenols through Ethyl o-cylphenylcarbonates to 0-Alkylphenols with Sodium Borohydride", Chem. Pharm. Bull., 1979, vol. 27, pp. 1490-1494.
Monti et al., "A Novel Endogenous Antimalarial: Fe(II)-Protoporphyrin IX$\alpha$(Heme) Inhibits Hematin Polymerization to $\beta$-Hematin (Malaria Pigment) and Kills Malaria Parasites", Biochemistry, 1999, vol. 38, pp. 8858-8863.
Noranate et al., "Rapid Dissemination of Plasmodium falciparum Drug Resistance Despite Strictly Controlled Antimalarial Use", Plos One, 2007, Issue 1, e139, pp. 1-12.
O'Brien et al., "Investigation of the Alamar Blue (resazurin) fluorescent dye for the assessment of mammalian cell cytotoxicity", Eur. J. Biochem., 2000, vol. 267, pp. 5424-5426.
Pearce et al., "Inhibitors of Cholesterol Biosynthesis. 2. Hypocholesterolemic and Antioxidant Activities of Benzopyran and Tetrahydronaphthalene Analogues of the Tocotrienols", J. Med. Chem., 1994, vol. 37, pp. 526-541.
Quiclet-Sire et al., "A Practical Variation on the Paal-Knorr Pyrrole Synthesis", Synlett, 2003, No. 1, pp. 75-78.
Schirmer et al., "Disulfide-Reductase Inhibitors as Chemotherapeutic Agents: The Design of Drugs for Trypanosomiasis and Malaria", Angew. Chem. Int. Ed. Engl., 1995, vol. 34, pp. 141-154.
Trager et al., "Human Malaria Parasites in Continuous Culture", Reports, Science, 1976, vol. 193, pp. 673-675.
Vargas et al., "Total Synthesis of 10-Norparvulenone and of O-Methylasparvenone Using a Xanthate-Mediated Free Radical Addition-Cyclization Sequence", Organic Letters, 2003, vol. 5, No. 20, pp. 3717-3719.
Vippagunta et al., "Characterization of chloroquine-hematin $\mu$-oxo dimer binding by isothermal titration calorimetry", Biochimica et Biophysica Acta, 2000, vol. 1475, pp. 133-140.
Wenzel et al., "Antimalarial versus Cytotoxic Properties of Dual Drugs Derived From 4-Aminoquinolines and Mannich Bases: Interaction with DNA", Antimalarial and Cytotoxic 4-Aminoquinolines, Supporting Information, pp. S1-S9. J. Med Chem 2010.
Wenzel et al., "Antimalarial versus Cytotoxic Properties of Dual Drugs Derived From 4-Aminoquinolines and Mannich Bases: Interaction with DNA", Journal of Medical Chemistry, 2010, vol. 53, pp. 3214-3226.
Zarchin et al., "Digestion of the host erythrocyte by malaria parasites is the primary target for quinoline-containing antimalarials", Biochemical Pharmacology, 1986, vol. 35, No. 14, pp. 2435-2442.
Zoungrana et al., "Safety and Efficacy of Methylene Blue Combined with Artesunate or Amodiaquine for Uncomplicated Falciparum Malaria: A Randomized Controlled Trial from Burkina Faso", Plos One, 2008, vol. 3, No. 2, e1630, pp. 1-7.

\* cited by examiner

| Structure | IC$_{50}$ (nM) against Pf Dd2 strain | IC$_{50}$ (nM) against Pf 3D7 strain | Toxicity IC$_{50}$ (μM) Human MRC-5 |
|---|---|---|---|
|  LJ186 | 73.17-110.4 nM** 109.4 nM*** | 119.8 nM | 3.12 μM |
|  EC060 | 59.1 ± 15.9**** | | > 64.0 |
|  EC061 | | | |
|  EC005 | 3230.0**** | | > 64.0 |
|  EC006 | 3187.0**** | | > 64.0 |
|  EC067 | | | |
|  EC069 | 1527.8 ± 659.1**** | | > 64.0 |
|  EC122 | 3501.0**** | | |
|  EC124 | 1860 ± 2.5**** | | |

| Structure | IC₅₀ (nM) against Pf Dd2 strain | IC₅₀ (nM) against Pf 3D7 strain | Toxicity IC₅₀ (μM) Human MRC-5 |
|---|---|---|---|
|  EC145 | 314.7 ± 183.0**** | | |
|  EC146 | 930.6 ± 18.1**** | | |
|  EC147 | 5838.0 ± 3500.0**** | | |
|  EC148 | 3292.0 ± 534.0**** | | |
|  EC054 | 2082.5 ± 1602.4**** | | > 64.0 |
|  EC055 | | | |
|  EC057 | 1746.0 ± 958.0**** | | > 64.0 |
|  EC058 | | | |
|  EC156 | 3094.5 ± 38.5**** | | |

| Structure | IC$_{50}$ (nM) against Pf Dd2 strain | IC$_{50}$ (nM) against Pf 3D7 strain | Toxicity IC$_{50}$ (µM) Human MRC-5 |
|---|---|---|---|
|  EC167 | 2706.0 ± 18.0**** | | |
|  BB6 | 8348 nM** <br> 9131.2 nM*** | 9516.6 nM | 5.90 µM |
|  EC040 | > 3,200 nM | > 3,200 nM | 6.93 µM |
|  EC038 | > 3,100 nM | > 3,100 nM | 2.15 µM |
|  EC037 | > 3,100 nM | > 3,100 nM | 1.78 µM |
|  BB12 | > 2,800 nM | > 2,800 nM | 2.28 µM |
|  BB49 | > 2,900 nM | > 2,900 nM | 9.19 µM |
|  BB48 | > 3,000 nM | > 3,000 nM | 0.67 µM |
|  BB27 | > 3,000 nM | > 3,000 nM | 0.95 µM |

| Structure | IC$_{50}$ (nM) against Pf Dd2 strain | IC$_{50}$ (nM) against Pf 3D7 strain | Toxicity IC$_{50}$ (µM) Human MRC-5 |
|---|---|---|---|
| Chloroquine | * 80.2 to 147.7 nM<br> 63.5 to 131.1 nM<br>* 134.0 to 147.7 nM<br>** 75.1 ± 6.7 nM | 7.9 nM<br>***8.6 nM | >32.00 µM |
|  P_TM24 = HB67 | 54 nM*<br>97.7 nM<br>70.4 ± 27.3 nM | 100.6 nM | >32.00 µM |
|  P_TM29 | 69.2 nM<br>43.2 ± 27.3 nM | 67.5 nM | >32.00 µM |
|  P_TM58 (LJ83K) | 21-51 nM*<br>153.4 nM** | 167.4 nM** | >64.00 µM |
|  DAL53-I141 | 149.6-199.5 nM<br>224.9 nM*<br>76.5 ± 19.0** | 177.3 nM | 19.4 µM |
|  DAL54 | 53.7 ± 7.4**** | | |
|  EC050 | 177.9 ± 54.8**** | | 7.06 |
|  DAL48-I133 | 125.0 ± 49.3**** | | |
|  DAL50-I137 | 163.9 ± 55.9**** | | |

FIGURE 1 (Cont'd)

| Structure | IC$_{50}$ (nM) against Pf Dd2 strain | IC$_{50}$ (nM) against Pf 3D7 strain | Toxicity IC$_{50}$ (μM) Human MRC-5 |
|---|---|---|---|
| EC125 | 163.2**** | | |
| EC172 | 2481.5 ± 190.5**** | | |
| EC019 | 138.6 ± 90.8**** | | >64.0 |
| EC021 | 138.3 ± 82.5**** | | >64.0 |
| KU1-050p | 3347**** | | 7.74 |
| DAL13-147 | 607.9 nM* | 1.7-2.4 μM** | 6.41 μM |
| DAL29-135 | 1715 nM*** | 727 nM | 4.45 μM |
| BB4 | 2174.2 nM** | 1510.8 nM | 2.58 μM |
| BB10 | 1206.35 nM*** | 1349.7 nM | 5.25 μM |

| Structure | IC$_{50}$ (nM) against Pf Dd2 strain | IC$_{50}$ (nM) against Pf 3D7 strain | Toxicity IC$_{50}$ (µM) Human MRC-5 |
|---|---|---|---|
|  BB8 | 249.5-340.8 nM** 691.35 nM*** | 340.2 nM** | 30.05 µM |
|  BB19 | 364.7 nM | > 367 nM | 2.95 µM |
|  BB16 | 623.5 nM*** | 442.5 nM | 4.00 µM |
|  BB17 | 437.5 nM*** | 391.5 nM | 1.87 µM |
|  LJ144K | 613 nM** | 457 nM** | > 64 µM |
|  LJ152K | | > 5 µM** | > 64 µM |
|  LJ161 | | > 5 µM** | > 64 µM |
|  LJ115 | | > 5 µM** | > 64 µM |

FIGURE 4

| Compound | Structure | IC$_{50}$ in 3mM DTNB reduction assay | Worm death at 48 hr (%) | |
|---|---|---|---|---|
| | | | +RBC 50 μM | -RBC 50 μM |
| Benzyl series | | | | |
| LJ81K (P_TM60) (benzyl series) | 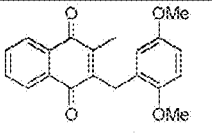 P_TM60 (LJ81K) | ~36% inhibition Poor SmTGR inhibitors, likely reversible and poor substrate, likely SmTGR inhibitor prodrug | 86 % D hairy phenotype | 83 % D hairy phenotype |
| LJ83K (P_TM58) (benzyl series) | 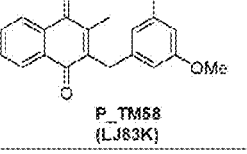 P_TM58 (LJ83K) | ~34% inhibition Poor SmTGR inhibitors, likely reversible and poor substrate, likely SmTGR inhibitor prodrug | 83 % D hairy phenotype | 83 % D hairy phenotype |
| DAL48-I133 | 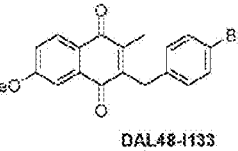 DAL48-I133 | 6.6 μM | 50% D hairy phenotype | 50% D hairy phenotype |
| DAL50-I137 | 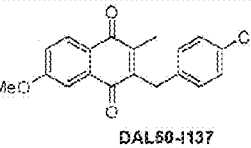 DAL50-I137 | 15 μM | 95 % D | 50 % D |
| DAL53-I141 | 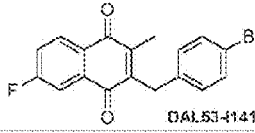 DAL53-I141 | 4.5 μM | 80 % D | 71 % D |
| EC050 | 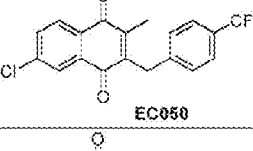 EC050 | ~90% inhibition (IC$_{50}$ = 6.6 μM) | | 100 % D (24h) |
| EC060 | 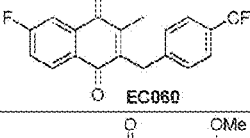 EC060 | ~81% inhibition (IC$_{50}$ = 19 μM) | | 0 % D |
| EC069 | 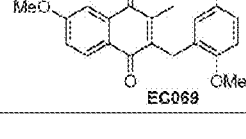 EC069 | ~100% inhibition (IC$_{50}$ = 5.8 μM) | | 0 % D |

Figure 4:
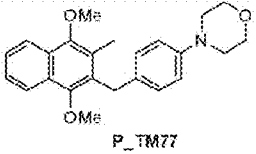
Figure 4:
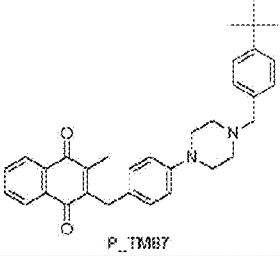

FIGURE 4 (Cont'd)

| Compound | Structure | | | |
|---|---|---|---|---|
| EC054 | EC054 | ~88% inhibition (IC$_{50}$ = 12.6 µM) | | 0 % D |
| EC057 | EC057 | ~0% inhibition | | 10 % D (40h) |
| DAL13-I47 (azamenadione) | DAL13-I47 | 12 µM | NA | NA |
| DAL 29-135 (azamenadione) | DAL29-135 | ~43% inhibition | 50% D | 50% D |

| Compound | Structure | Inhibition (%) IC$_{50}$ in 3mM DTNB reduction assay | Worm death at 48 hr (%) | |
|---|---|---|---|---|
| | | | +RBC at 50/10/5 µM compound | -RBC |
| DAL13-I47 | DAL13-I47 | 4.33 µM | 0/0/0 | |
| BB8 | BB8 | 6.02 µM | ~<40%D at 50 µM | ~<40%D at 50 µM |
| BB6 | BB6 | 11.2 µM | ~30%D at 50 µM | ~30%D at 50 µM |
| BB12 | BB12 | 332 nM | 0/0/0 worms slow at 50 µM | |

FIGURE 4 (Cont'd)

| Compound | Structure | Inhibition (%) IC$_{50}$ in 3mM DTNB reduction assay | Worm death at 48 hr (%) +RBC at 50/10/5 µM compound 01/31/2011 | -RBC |
|---|---|---|---|---|
| BB19 | BB19 | ~58% inhibition | 93/7/0 | |
| BB49 | BB49 | ~71% inhibition | 100/53/0 may prevent Hz formation | |
| BB4 | BB4 | 3.9 µM | <50%D at 50 µM | 50%D at 50 µM |
| BB16 | BB16 | 20.4 µM | ~<60%D at 50 µM | ~<40%D at 50 µM |
| BB48 | BB48 | ~53% inhibition | 0/0/0 worms slow at 50 µM | |
| BB10 | BB10 | ~70 % inhibition (SmTGR: 5 nM; compound: 50 µM) | <40%D at 50 µM | <40%D at 50 µM |
| BB17 | BB17 | ~48 % inhibition (SmTGR: 5 nM; compound: 50 µM) | ~<70%D at 50 µM | ~<60%D at 50 µM |
| BB27 | BB27 | ~53% inhibition | 100/13/0 | |

FIGURE 4 (Cont'd)

| Compound | Structure | Inhibition (%) IC$_{50}$ in 3mM DTNB reduction assay | Worm death at 24hr (%) + 10 μM Hb at 50 μM compound |
|---|---|---|---|
| Benzyl/Benzoyl series | | | |
| P_TM23 (benzoyl) | 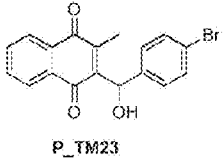 P_TM23 | ~62% inhibition | 25% D |
| P_TM40 (benzoyl) | 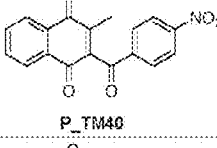 P_TM40 | ~93% inhibition 7.58 μM | D |
| P_TM46 (benzoyl) | 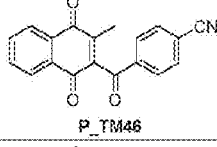 P_TM46 | ~42% inhibition | 45% D |
| P_TM47 (benzoyl) | 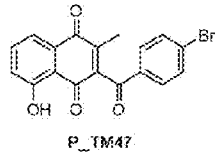 P_TM47 | ~55% inhibition | 60% D |
| KU1-050p | 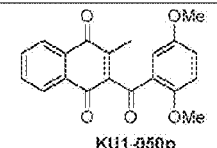 KU1-050p | ~21% inhibition | 10 % D (48h) |
| P_TM50 (benzyl) | 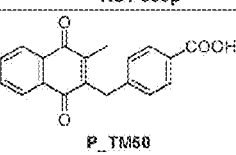 P_TM50 | ~90% inhibition (12.65 μM) | 65% D |
| P_TM72 (benzyl) | 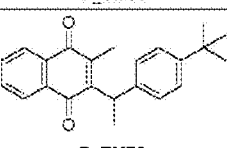 P_TM72 | ~0% inhibition | 30% D |
| P_TM17 (benzoyl) | 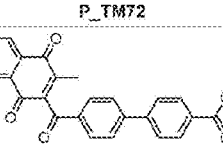 P_TM17 | ~77% inhibition | 40% D |

Treatments 1 and 4:  T1 = LJ83K - 2 x 33 mg/kg
T4 = control

TOTAL SYNTHESIS OF REDOX-ACTIVE 1.4-NAPHTHOQUINONES AND THEIR METABOLITES AND THEIR THERAPEUTIC USE AS ANTIMALARIAL AND SCHISTOMICIDAL AGENTS

The present invention relates to a new process for synthesizing 1.4-naphthoquinones and their metabolites and to their application in therapeutics.

*Plasmodium falciparum* and *Schistosoma mansoni* are blood feeding parasites digesting the host's hemoglobin. and detoxifying the toxic heme into an insoluble polymer called hemozoin.

*Plasmodium* parasites are exposed to elevated fluxes of reactive oxygen species during the life cycle in the human host and therefore high activities of intracellular antioxidant systems are needed. The most important antioxidative system consists of thiols which are regenerated by disulfide reductases; these include three validated drug targets the glutathione reductases (GR) of the malarial parasite *Plasmodium falciparum* and of human erythrocytes as well as the thioredoxin reductase of *P. falciparum* (Schirmer et al. *Angew. Chem. Int. Ed. Engl.* 1995, 34. 141-54; Krauth-Siegel et al. *Angew. Chem. Int. Ed. Engl.* 2005, 44, 690-715). One validated target against the malarial parasite *Plasmodium falciparum* is the enzyme glutathione reductase which reduces glutathione disulfide to its thiol form glutathione on the expense of NADPH. Glutathione is implicated in the development of chloroquine resistance: an elevation of the glutathione content in *P. falciparum* leads to increased resistance to chloroquine, while glutathione depletion in resistant strains restores sensitivity to chloroquine (Meierjohan et al. *Biochem. J.* 200, 368, 761-768). High intracellular glutathione levels depend inter alia on the efficient reduction of glutathione disulfide by GR and by reduced thioredoxin (Kanzok et al. *Science* 2001, 291, 643-646). The contribution to the reversal of drug resistance or to a synergistic effect by GR inhibitors like methylene blue is currently investigated for the commonly used antimalarial drugs chloroquine, amodiaquine, artesunate in clinical trials (Zoungrana et al. *PLoS One,* 2008. 3:e1630; Meissner et al. *Malar J.* 2006. 5:84; Akoachere et al. *Antimicrob. Agents Chemother.* 2005, 49, 4592-7). Derivatives of menadione per se were shown to be potent inhibitors both of human and *Plasmodium falciparum* glutathione reductases acting in the low micromolar range in parasitic assays with *P. falciparum* in cultures (Biot et al. *J. Med. Chem.* 47. 5972-5983; Bauer et al. *J. Am. Chem. Soc.* 2006. 128. 10784-10794). The dual drugs combining a 4-aminoquinoline and a menadione-based GR inhibitor exhibited high antimalarial potencies in the low nanomolar range in the malarial assays in vitro. (Davioud-Charvet et al. *J. Med. Chem.* 2001, 44, 4268-4276; Friebolin et al., *J. Med. Chem.* 2008. 51. 1260-77; Wenzel et al. *J. Med. Chem.* 2010. 53, 3214-26).

The malarial parasite *Plasmodium falciparum* digests a large amount of its host cell hemoglobin during its erythrocytic cycle as source of essential nutrients (Zarchin et al. *Biochem. Pharmacol.* 198, 35, 2435-2442). The digestion is a complex process that involves several proteases and takes place in the food vacuole of the parasite leading to the formation of iron II ferroprotoporphyrin (FPIX) (Goldberg et al. *Parasitol. Today.* 1992, 8, 280-283) as toxic byproduct for the parasite which is immediately oxidized to FPIX($Fe^{3+}$). Due to the toxicity of FPIX the parasites have developed a detoxification process in which FPIX($Fe^{3+}$) (hematin) is polymerized forming inert crystals of hemozoin or malaria pigment (Dorn et al. *Nature* 1995, 374, 269-271). FPIX($Fe^{2+}$) is an inhibitor of hematin polymerization (Monti et al. *Biochemistry* 1999. 38, 8858-8863). Early observations indicated that free FPIX ($Fe^{3+}$) is able to form complexes with aromatic compounds bearing nitrogen, e.g. pyridines, 4-aminoquinolines (Cohen et al. *Nature* 1964, 202, 805-806; Egan et al. *J. Inorg. Biochem.* 2006, 100, 916-926) and it is now well established that 4-aminoquinolines can form μ-oxodimers with FPIX thus preventing the formation of hemozoin. Consequently, an increase of free heme concentration in the food vacuole is responsible for killing the parasite (Vippagunta et al. *Biomed. Biochim. Acta* 2000, 1475, 133-140). In the presence of reactive oxygen species iron-porphyrin complexes (e.g. free heme) are catalysts for oxidation reactions. Released in large quantities in the food vacuole of the parasite they are thought to strongly influence the activity of a drug under the specific acidic conditions of the malarial food vacuole. Drug metabolites can be more active than its precursor (pro-drug effect) or toxic (Bernadou et al. *Adv. Synth. Catal.* 2004, 346, 171-184).

The reduction of methemoglobin($Fe^{3+}$) into hemoglobin ($Fe^{2+}$) is of great importance in the treatment of malaria. Since the malarial parasite is much more capable of using methemoglobin as nutrient and digests methemoblobin faster than hemoglobin the reduction of methemoglobin can be used to slow down the parasite's methemoglobin digestion by reducing its concentration. A second reason to target the reduction of methemoglobin is that methemoglobin, the ferric form of hemoglobin, is not capable of oxygen transport. High levels of methemoglobin are found during *Plasmodium vivax* infections (Anstey et al. *Trans. R. Soc. Trop. Med. Hyg.* 1996, 90, 147-151). A reduced oxygen carrying capacity of blood due to anaemia is even worsened by reduction in oxygen carrying capacity from even a modest concentration of methemoglobin leading to an impaired supply of oxygen for the tissue; a specific situation observed in cerebral malaria.

The two major antioxidant defense lines in *Plasmodium* are provided by the glutathione and the thioredoxin systems. Both systems are NADPH-dependent and are driven by homodimeric FAD-dependent oxido-reductases, namely glutathione reductase (PfGR) and thioredoxin reductase (PfTrxR). Both GRs from the human erythrocyte and from the malarial parasite are essential proteins for the survival of the malarial parasite infecting red blood cells and were identified as targets of antimalarial drugs. They maintain the redox equilibrium in the cytosol by catalyzing the physiological reaction: NADPH+$H^+$+GSSG→$NADP^+$+2 GSH, in particular in the course of the pro-oxidant process of hemoglobin digestion in the intraerythrocytic plasmodial cycle. The parasite evades the toxicity of the released heme by expressing two major detoxification pathways, i.e. hemozoin formation in the food vacuole and an efficient thiol network in the cytosol. Hemozoin formation is inhibited by 4-aminoquinolines such as chloroquine (CQ) and heme FPIX($Fe^{2+}$). The thiol network maintained by GR is inhibited by numerous redox-cyclers including 1,4-naphthoquinones disclosed in patent application WO in the name of the inventors, phenothiazinium derivatives as methylene blue (MB) and the natural phenazine pyocyanin (PYO), and nitroaromatics. Methylene blue, an efficient GR subversive substrate, was the first synthetic antimalarial drug used in human medicine at the beginning of the 20th century but was abandoned with the launch of chloroquine in the 40s'. Its reduced form (LMB) is known to reduce $Fe^{3+}$ to $Fe^{2+}$ from both methemoglobin (MetHb) and heme (FPIX) species.

Since the malarial parasite *Plasmodium falciparum* multiplies in human erythrocytes, most drugs are directed against this stage of the life cycle of the parasite.

The most administered drugs are chloroquine and 4-aminoquinoline derivatives, and artemisinin and arthemether derivatives. Present malaria treatment (recommended by WHO) is based on combination therapy: artemisinin combined therapy (ACT). Highly and multi-drug-resistant *Plasmodium* strains spread all over the world. For instance, very recent studies showed that resistant *Plasmodium falciparum* strains to artemether (artemisinin analogue) appeared in French Guiana and Senegal (Jambou et al. *Lancet.* 2005, 366, 1960-3; XX). Also, decreased in vitro susceptibility of *Plasmodium falciparum* isolates to artesunate, mefloquine, chloroquine, and quinine in Cambodia from 2001 to 2007 were observed (Noranate N et al. *PLoS One* 2007, 2:e139; Lim et al. *Antimicrob. Agents Chemother.* 2010, 54, 2135-42).

The chemotherapy of schistosomiasis is currently based on only one drug, Praziquantel (PZQ). Drug resistances developed by both parasites are emerging and there is an urgent need for new antiparasitic drugs. While PZQ is very effective in schistosomiasis treatment and has a very low toxicity, it has limited action against larval parasites. This leads to ineffective cures in areas of high transmission. Furthermore, there is evidence of evolving PZQ-resistant parasites in Egypt, suggesting the urgency for the development of novel schistosomicidal agents. Clinical drug resistance against PZQ has also been noted in Kenya (Melman S D et al. *PLoS Negl. Trop. Dis.* 2009, 3:e504). Artemisinin-based antischistosomal drugs have good activity against larval parasites, but limited activity against adult parasites. The use of the same molecules (ex: artemisinin) to treat both malaria and schistosomiasis put the antimalarial application at risk if multi-resistant parasites appear.

There is therefore still a need for compounds having efficiency against malaria and schistosomiasis without the usual drawbacks of the existing drugs. Furthermore, there is a need for compounds which are easy to formulate in pharmaceutical compositions.

In international application WO 2009/118327 the inventors disclosed a new series of compounds based on the 2-methyl-1,4-naphthoquinone core (named menadione). These compounds were 3-benzylmenadione derivatives (benzylNQ) and most of them were synthesized in one step with satisfactory yields. The series was tested in in vitro tests against the chloroquine-sensitive strain 3D7, the chloroquine-resistant strain K1, the multidrug-resistant strain Dd2 and against a Pf-GHA parasite strain in vitro. The compounds showed antimalarial effects in the low nM range while displaying moderate cytotoxicity in the µM range and no hemolysis of red blood cells at therapeutic doses. The most active compounds were also tested in a mouse model infected by *P. berghei* displaying significant decrease in parasitemia at 30 mg/kg (ip and po), Now the inventors developed new methodologies for total synthesis of polysubstituted 3-benzylmenadione derivatives and aza analogues. They also studied the potential metabolism of these compounds, synthesized the putative metabolites and investigated the mechanism of action. The metabolites, the benz[c]-xanthen-7-ones (benzxanthones), were tested in the hematin polymerization assay.

The inventors also studied new uses of the molecules, described in the present patent application, as antiparasitic agents to target blood-feeding parasites, including the protozoans *Plasmodium, Eimeria* and *Babesia,* the helminths including the worm *Schistosoma,* and more broadly the external blood-feeding parasites like fleas and ticks, to treat humans and animals (cattle, pets), in human and veterinary medicines, as prophylactics or as treatments, respectively.

In the publication *Journal of Medicinal Chemistry* 1991, Vol. 34, N° 1 p. 270 a product code-named n° 25 belonging to the chemical family of the Pyridylmethyl naphtoquinones is disclosed.

Consequently, a first object of the invention are compounds of formula (I)

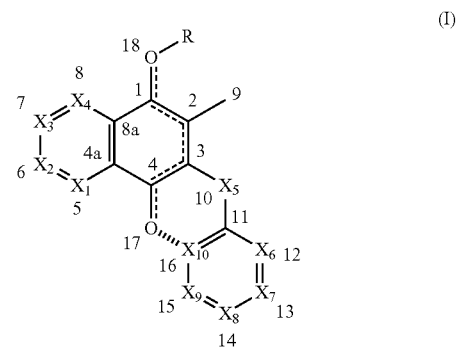

(I)

wherein:
either $X_1$, $X_2$, $X_3$ and $X_4$ represent all carbon atoms,
either one of $X_1$, $X_2$, $X_3$ and $X_4$ represents a nitrogen atom and the three others represent carbon atoms,
either $X_1$ and $X_4$ represent a nitrogen atom and both $X_2$ and $X_3$ represent carbon atoms,
the bond - - - - - between O in position 17 and $X_{10}$ represents no bond or a single bond,
the bond ══ represents either a single bond or a double bond,
$X_5$ represents CO or $CH_2$ or CHOH,
$X_6$, $X_7$, $X_8$, $X_9$ and $X_{10}$ represent all carbon atoms or one of them represents a nitrogen atom and the four others are carbon atoms,
with the proviso that
  i) when the bond - - - - - between O17 and $X_{10}$ represents a single bond, then the bonds ══ between atoms in positions C1/O18 and C4/O17 are single bonds, the bonds between carbons in positions C1/C2 and C3/C4 are double bonds, the bond between carbons in positions C2/C3 is a simple bond, and R represents a hydrogen atom or an acetyl group and $X_{10}$ is not a nitrogen atom and
  ii) when the bond - - - - - between O17 and $X_{10}$ represents no bond, then R does not exist and the bonds ══ between atoms C1/O18 and C4/O17 are double bonds, the bonds between carbons in positions C1/C2 and C3/C4 are simple bonds, the bond between carbons in positions C2/C3 is a double bond, and $X_1$, $X_2$, $X_3$ and $X_4$ when they are carbon atoms being optionally substituted by:
  a hydrogen atom,
  a halogen atom,
  a hydroxy group,
  a triflate group,
  a phosphate group,
  a linear or branched ($C_1$-$C_4$)alkyl group,
  a linear or branched ($C_1$-$C_4$)alkoxy group,
  a thio($C_1$-$C_4$)alkoxy group,
  a pentafluorosulfanyl group,
  —$SCF_3$
  —$SCH_2F$,
  a trifluoromethyl group,
  a trifluoromethoxy group, $X_6, X_7, X_8, X_9, X_{10}$—except when atoms O17 and $X_{10}$ are bound by a simple bond and $X_{10}$ is a quarternary carbon atom—being optionally substituted by:
a hydrogen atom,
a halogen atom,
a hydroxy group,
a linear or branched $(C_1-C_4)$alkyl group,
a linear or branched $(C_1-C_4)$alkoxy group,
a thio$(C_1-C_4)$alkoxy group,
a pentafluorosulfanyl group,
a trifluoromethyl group,
a trifluoromethoxy group,
a difluoromethoxy group,
a difluoromethyl group,
—COOH,
—COO$(C_1-C_4)$alkyl group,
—CONR$_1$(CH$_2$)$_m$CN, with $R_1$ being a hydrogen atom or a linear or branched $(C_1-C_4)$alkyl group and m=1, 2 or 3,
—CSNR$_1$(CH$_2$)$_m$CN, with $R_1$ being a hydrogen atom or a linear or branched $(C_1-C_4)$alkyl group m=1, 2 or 3,
—CONR$_1$Het with $R_1$ being a hydrogen atom or a linear or branched $(C_1-C_4)$alkyl group, Het representing a pyridine-2-yl group, said group optionally substituted by an amino group in -6 or by a —CONH$_2$ group in -5,
—NO$_2$,
—CN,
—NR$_2$R$_3$ with $R_2$ and $R_3$ representing each independently a hydrogen atom, an amino protecting group selected from the group comprising Boc group and $(C_1-C_4)$alkyl group, or $R_2$ and $R_3$ forming with the nitrogen atom which bears them a cyclic group selected from the group comprising morpholine, piperidine, and piperazine groups, said cyclic groups being optionally substituted,
an aryl group or an aryl group substituted by one or several substituents selected from the group comprising a $(C_1-C_4)$alkyl group, a —NO$_2$ group, a —COOR$_4$ with $R_4$ selected from a hydrogen atom and a linear or branched $(C_1-C_4)$alkyl group, a —NR$_5$R$_6$ with $R_5$ and $R_6$ independently selected from the group comprising a hydrogen atom and a linear or branched $(C_1-C_4)$alkyl group,
a heterocyclic group selected from the group comprising morpholinyl group or piperidinyl, or piperazinyl group, each of said group being optionally substituted by one or several substituents selected from the group comprising a linear or branched $(C_1-C_4)$alkyl group, —COOCH$_2$CH$_3$, or a group and the pharmaceutically acceptable derivatives thereof,
for their use as antiparasitic agents to target blood-feeding parasites,
with the proviso that when the blood-feeding parasite is *Plasmodium*, then when $X_1, X_2, X_3$ and $X_4$ are all carbon atoms, or when $X_1$ is a nitrogen atom, and $X_2, X_3$ and $X_4$ are all carbon atoms, then at least one of $X_6, X_7, X_8, X_9$ and $X_{10}$ represents a nitrogen atom.

The present invention also deals with compounds of formula (Ip)

(Ip)

wherein:
either $X_1, X_2, X_3$ and $X_4$ represent all carbon atoms,
either one of $X_1, X_2, X_3$ and $X_4$ represents a nitrogen atom and the three others represent carbon atoms,
either $X_1$ and $X_4$ represent a nitrogen atom and both $X_2$ and $X_3$ represent carbon atoms,
the bond ----- between O in position 17 and $X_{10}$ represents no bond or a single bond,
the bond ═══ represents either a single bond or a double bond,
$X_5$ represents CO or CH$_2$ or CHOH,
$X_6, X_7, X_8, X_9$ and $X_{10}$ represent all carbon atoms or one of them represents a nitrogen atom and the four others are carbon atoms,
with the proviso that
i) when the bond ----- between O17 and $X_{10}$ represents a single bond, then the bonds ═══ between atoms in positions C1/O18 and C4/O17 are single bonds, the bonds between carbons in positions C1/C2 and C3/C4 are double bonds, the bond between carbons in positions C2/C3 is a simple bond, and R represents a hydrogen atom or an acetyl group and $X_{10}$ is not a nitrogen atom and
ii) when the bond ----- between O17 and $X_{10}$ represents no bond, then R does not exist and the bonds ═══ between atoms C1/O18 and C4/O17 are double bonds, the bonds between carbons in positions C1/C2 and C3/C4 are simple bonds, the bond between carbons in positions C2/C3 is a double bond, and
$X_1, X_2, X_3$ and $X_4$ when they are carbon atoms being optionally substituted by:
a hydrogen atom,
a halogen atom,
a hydroxy group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—SCF$_3$
—SCH$_2$F,
a trifluoromethyl group,
a trifluoromethoxy group,
$X_6, X_7, X_8, X_9, X_{10}$—except when atoms O17 and $X_{10}$ are bound by a simple bond and $X_{10}$ is a quarternary carbon atom—being optionally substituted by:
a hydrogen atom,
a halogen atom,
a hydroxy group,
a linear or branched $(C_1-C_4)$alkyl group,
a linear or branched $(C_1-C_4)$alkoxy group,
a thio$(C_1-C_4)$alkoxy group,
a pentafluorosulfanyl group, a trifluoromethyl group,
a trifluoromethoxy group,
a difluoromethoxy group,
a difluoromethyl group,
—COOH,
—COO($C_1$-$C_4$)alkyl group,
—CONR$_1$(CH$_2$)$_m$CN, with R$_1$ being a hydrogen atom or a linear or branched ($C_1$-$C_4$)alkyl group and m=1, 2 or 3,
—CSNR$_1$(CH$_2$)$_m$CN, with R$_1$ being a hydrogen atom or a linear or branched ($C_1$-$C_4$)alkyl group m=1, 2 or 3,
—CONR$_1$Het with R$_1$ being a hydrogen atom or a linear or branched ($C_1$-$C_4$)alkyl group, Het representing a pyridine-2-yl group, said group optionally substituted by an amino group in -6 or by a —CONH$_2$ group in -5,
—NO$_2$,
—CN,
—NR$_2$R$_3$ with R$_2$ and R$_3$ representing each independently a hydrogen atom, an amino protecting group selected from the group comprising Boc group and ($C_1$-$C_4$)alkyl group, or R$_2$ and R$_3$ forming with the nitrogen atom which bears them a cyclic group selected from the group comprising morpholine, piperidine, and piperazine groups, said cyclic groups being optionally substituted,
an aryl group or an aryl group substituted by one or several substituents selected from the group comprising a ($C_1$-$C_4$)alkyl group, a —NO$_2$ group, a —COOR$_4$ with R$_4$ selected from a hydrogen atom and a linear or branched ($C_1$-$C_4$)alkyl group, a —NR$_5$R$_6$ with R$_5$ and R$_6$ independently selected from the group comprising a hydrogen atom and a linear or branched ($C_1$-$C_4$)alkyl group,
a heterocyclic group selected from the group comprising morpholinyl group or piperidinyl or piperazinyl group, each of said group being optionally substituted by one or several substituents selected from the group comprising a linear or branched ($C_1$-$C_4$)alkyl group, —COOCH$_2$CH$_3$, or a group

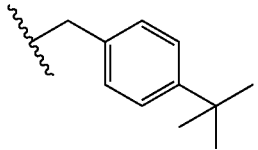 [SMILES: *Cc1ccc(C(C)(C)C)cc1]

and the pharmaceutically acceptable derivatives thereof,
for their use as antiparasitic agents to target blood-feeding parasites,
with the proviso that when the blood-feeding parasite is Plasmodium, then when X$_1$, X$_2$, X$_3$ and X$_4$ are all carbon atoms, or when X$_1$ is a nitrogen atom, and X$_2$, X$_3$ and X$_4$ are all carbon atoms, then at least one of X$_6$, X$_7$, X$_8$, X$_9$ and X$_{10}$ represents a nitrogen atom.

According to the instant invention, blood-feeding parasites includes the protozoans Plasmodium, Eimeria, and Babesia, the helminths including the worm Schistosoma, and more broadly the external blood-feeding parasites like fleas and ticks. Thus the compounds according to the invention may be used to treat humans and animals (cattle, pets), in human and veterinary medecines, as prophylaxics or as treatments, respectively. The following blood-feeding parasites may be cited Schistosoma mansoni, Schistosoma haematobium, Schistosoma japonicum, Schistosoma mekongi, Schistosoma intercalatum, Schistosoma bovis and Schistosoma nasale, Plasmodium falciparum, Plasmodium vivax, Plasmodium ovale, Plasmodium malariae, Babesia divergens, Babesia microti, and all Eimeria spp. being principal cause of coccidiosis, highly pathogenic, especially in young domesticated mammals, herbivores, and birds.

According to the present invention, a "pharmaceutically acceptable salt" is a pharmaceutically acceptable, organic or inorganic acid or base salt of a compound of the invention, Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, hydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

According to the invention, the term "halogen" refers to bromine atom, chlorine atom, fluorine atom or iodine atom.

According to the invention, the term "alkyl" refers to a straight or branched chain, saturated hydrocarbon having the indicated number of carbon atoms. A ($C_1$-$C_4$) alkyl is meant to include but is not limited to methyl, ethyl, propyl, isopropyl, butyl, sec-butyl, tert-butyl. An alkyl group can be unsubstituted or optionally substituted with one or more substituents selected from halogen atom, hydroxy group or amino group.

The term "alkoxy" refers to a —O-alkyl group having the indicated number of carbon atoms. A ($C_1$-$C_4$)alkoxy group includes —O-methyl, —O-ethyl, —O-propyl, —O-isopropyl, —O-butyl, —O-sec-butyl, —O-tert-butyl.

The term "thioalkoxy" refers to an S—O-alkyl group having the indicated number of carbon atoms. A thio($C_1$-$C_4$) alkoxy group includes S—O-methyl, S—O-ethyl, S—O-propyl, S—O-isopropyl, S—O-butyl, S—O-sec-butyl, S—O-tert-butyl.

The term "aryl" refers to a 6- to 18-membered monocyclic, bicyclic, tricyclic, or polycyclic aromatic hydrocarbon ring system. Examples of an aryl group include phenyl, naphthyl, pyrenyl, anthracyl, quinolyl, and isoquinolyl.

The term "heteroaryl" refers to small sized heterocycles including di- and tri-azoles, tetrazole, thiophene, furan, imidazole, In an advantageous embodiment according to the invention, the compounds used as antischistosomal agents are compounds of formula (I) wherein
X$_1$, X$_2$, X$_3$ and X$_4$ represent all carbon atoms, with X$_2$ or X$_3$ optionally substituted by a halogen atom or a linear or branched ($C_1$-$C_4$) alkoxy group,
the bond - - - - - between O in position 17 and X$_{10}$ represents no bond and the bonds ═ between atoms C1/O18 and C4/O17 are double bonds, the bonds between carbons in positions C1/C2 and C3/C4 are simple bonds, the bond between carbons in positions C2/C3 is a double bond, then R does not exist and $X_5$ represents CO or $CH_2$ or CHOH, $X_6$, $X_7$, $X_8$, $X_9$ and $X_{10}$ represent all carbon atoms with at least one of $X_6$, $X_7$, $X_8$, $X_9$, optionally substituted by a substituent selected from a halogen atom, a linear or branched ($C_1$-$C_4$)alkyl group, a linear or branched ($C_1$-$C_4$)alkoxy group, —a trifluoromethyl group, —a trifluoromethoxy group, —COOH, —CN, —$NO_2$, a —$NR_2R_3$ with $R_2$ and $R_3$ representing each independently a hydrogen atom, an amino protecting group selected from the group comprising Boc group and ($C_1$-$C_4$)alkyl group, or $R_2$ and $R_3$ forming with the nitrogen atom which bears them a cyclic group selected from the group comprising morpholine, piperidine, and piperazine groups, said cyclic groups being optionally substituted.

In another advantageous embodiment according to the invention, the compounds used as antischistosomal agents are compounds of formula (I) wherein $X_1$ represents a nitrogen atom and $X_2$, $X_3$ and $X_4$ carbon atoms, with at least one of $X_2$, $X_3$ and $X_4$ being optionally substituted by a linear or branched ($C_1$-$C_4$)alkyl group, the bond - - - - - between O in position 17 and $X_{10}$ represents no bond and the bonds ═══ between atoms C1/O18 and C4/O17 are double bonds, the bonds between carbons in positions C1/C2 and C3/C4 are simple bonds, $X_5$ represents $CH_2$, $X_6$, $X_7$, $X_8$, $X_9$ and $X_{10}$ represent all carbon atoms with at least one of $X_6$, $X_7$, $X_8$, $X_9$ optionally substituted by a substituent selected from a halogen atom, a linear or branched ($C_1$-$C_4$)alkoxy group and—a trifluoromethyl group.

Some compounds are new and are also part of the invention.

Consequently another object of the invention are new compounds of formula (Ia):

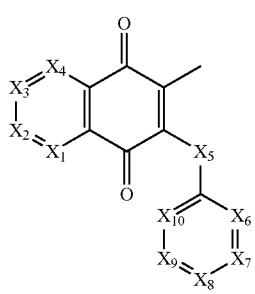

(Ia)

wherein either $X_1$, $X_2$, $X_3$ and $X_4$ represent all carbon atoms either $X_1$ represents a carbon atom and one of $X_2$, $X_3$ and $X_4$ represents a nitrogen atom and the two others represent carbon atoms, either $X_1$ and $X_4$ represent each a nitrogen atom and $X_2$ and $X_3$ represent a carbon atom, $X_5$ represents CO or $CH_2$ or CHOH, $X_6$, $X_7$, $X_8$, $X_9$ and $X_{10}$ represent all carbon atoms or one of them represents a nitrogen atom and the four others are carbon atoms, $X_1$, $X_2$, $X_3$, $X_4$, $X_6$, $X_7$, $X_8$, $X_9$ and $X_{10}$ when they are carbon atoms may be substituted as disclosed above, with the proviso than if $X_1$, $X_2$, $X_3$ and $X_4$ represent all carbon atoms or if $X_1$ represents a nitrogen atom, then at least one of $X_6$, $X_7$, $X_8$, $X_9$ and $X_{10}$ represents a nitrogen atom.

Another aspect of the invention are new compounds responding to formula (Ia):

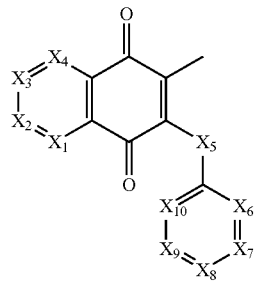

(Ia)

wherein either $X_1$, $X_2$, $X_3$ and $X_4$ represent all carbon atoms either $X_1$ represents a carbon atom and one of $X_2$, $X_3$ and $X_4$ represents a nitrogen atom and the two others represent carbon atoms, either $X_1$ and $X_4$ represent each a nitrogen atom and $X_2$ and $X_3$ represent a carbon atom, $X_5$ represents CO or $CH_2$ or CHOH, $X_6$, $X_7$, $X_8$, $X_9$ and $X_{10}$ represent all carbon atoms or one of them represents a nitrogen atom and the four others are carbon atoms, $X_1$, $X_2$, $X_3$, $X_4$, $X_6$, $X_7$, $X_8$, $X_9$ and $X_{10}$ when they are carbon atoms may be substituted as defined above, with the proviso than if $X_1$, $X_2$, $X_3$ and $X_4$ represent all carbon atoms or if $X_1$ represents a nitrogen atom, then at least one of $X_6$, $X_7$, $X_8$, $X_9$ and $X_{10}$ represents a nitrogen atom and if X1, X2, X3 and X4 all represent unsubstituted carbon atoms and X5 represents CH2 then neither X7 nor X9 represents a nitrogen atom.

The second part of the above disclaimer is intended to exclude the product code-named n° 25 in the publication Journal of Medicinal Chemistry 1991, Vol. 34, N° 1 p. 270.

In an advantageous embodiment, the compounds according to the invention are selected from the group comprising:

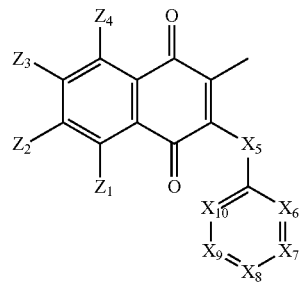

(Ia1)

-continued

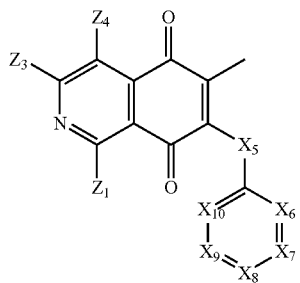
(Ia2)

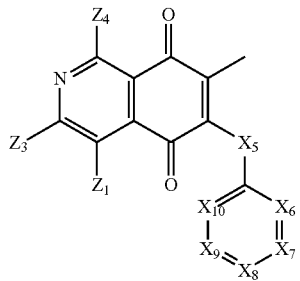
(Ia3)

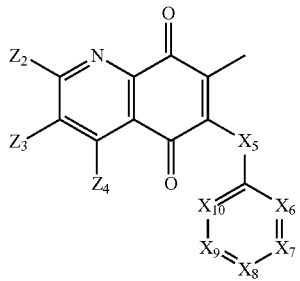
(Ia4)

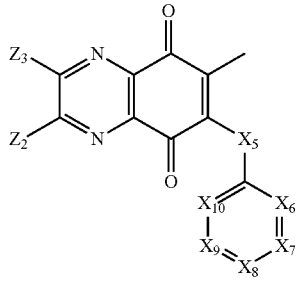
(Ia5)

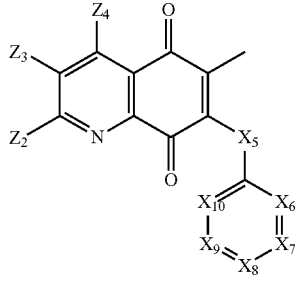
(Ia6)

wherein $Z_1$, $Z_2$, $Z_3$ et $Z_4$ represent each independently of the other,
a hydrogen atom,
a halogen atom,
a hydroxy group,
a triflate group,
a phosphate group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—SCF$_3$
—SCH$_2$F,
a trifluoromethyl group,
a trifluoromethoxy group, $X_6$, $X_7$, $X_8$, $X_9$ and $X_{10}$ are as defined above, with the proviso that in the compound of formula (Ia1) or of formula (Ia6) at least one of $X_6$, $X_7$, $X_8$, $X_9$ and $X_{10}$ represents a nitrogen atom.

In an other advantageous embodiment, the compounds according to the invention are selected from the group comprising:

(Ia1)

(Ia2)

(Ia3)

(Ia4)

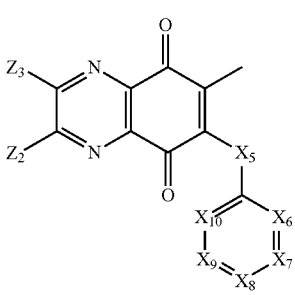

(Ia5)

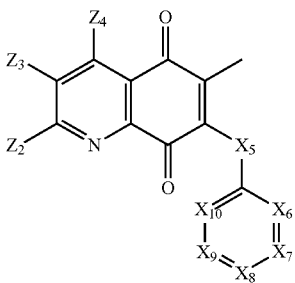

(Ia6)

wherein $Z_1$, $Z_2$, $Z_3$ et $Z_4$ represent each independently of the other,
- a hydrogen atom,
- a halogen atom,
- a hydroxy group,
- a linear or branched $(C_1-C_4)$alkyl group,
- a linear or branched $(C_1-C_4)$alkoxy group,
- a thio$(C_1-C_4)$alkoxy group,
- a pentafluorosulfanyl group,
- —$SCF_3$
- —$SCH_2F$,
- a trifluoromethyl group,
- a trifluoromethoxy group, $X_6$, $X_7$, $X_8$, $X_9$ and $X_{10}$ are as defined above, with the proviso that in the compound of formula (Ia1) or of formula (Ia6) at least one of $X_6$, $X_7$, $X_8$, $X_9$ and $X_{10}$ represents a nitrogen atom.

Another object of the invention are compounds of formula (Ib):

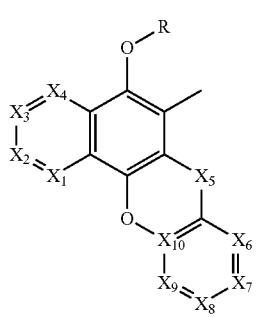

(Ib)

wherein
either $X_1$, $X_2$, $X_3$ and $X_4$ represent all carbon atoms,
or one of $X_1$, $X_2$, $X_3$ and $X_4$ represents a nitrogen atom and the three others represent carbon atoms,
or $X_1$ and $X_4$ represent a nitrogen atom and $X_2$ and $X_3$ represent carbon atoms,
$X_5$ represents CO or $CH_2$ or CHOH, $X_6$, $X_7$, $X_8$, $X_9$ and $X_{10}$ represent all carbon atoms or one of $X_6$, $X_7$, $X_8$, $X_9$ represents a nitrogen atom and the four others are carbon atoms, R represents a hydrogen atom, or an acetyl group, $X_1$, $X_2$, $X_3$, $X_4$, $X_6$, $X_7$, $X_8$ and $X_9$ when they are carbon atoms may be substituted as defined above.

Another object of the invention are compounds of formulas (Ia) and (Ib) and the pharmaceutically acceptable salts thereof for their use as drugs, especially as antiparasitic agents to target blood-feeding parasites.

Another object of the invention is the use of compounds of formulas (I) in general and in particular (Ia), (Ia1) to (Ia6) (Ib) and (Ip) and the pharmaceutically acceptable salts thereof in therapy and prophylaxis.

The instant invention also provides a method for the prevention or the treatment of parasitic disease due to blood-feedings parasites of humans, cattles and pets, in particular human diseases like malaria or schistosomasis comprising the administration to a patient in need thereof of a therapeutically effective amount of a compound of formula (I) as defined above.

In accordance with the invention, the compounds of formula (Ia), (Ia1) to (Ia6) (Ib) and (Ip) are useful in pharmaceutically acceptable compositions. Thus another object of the invention are pharmaceutically acceptable composition comprising at least one compound selected from compounds of formula (Ia), (Ia1) to (Ia6), (Ip) and (Ib) and salts thereof in combination with excipients and/or pharmaceutically acceptable diluents or carriers. Any conventional carrier material can be utilized. The carrier material can be an organic or inorganic inert carrier material, for example one that is suitable for oral administration. Suitable carriers include water, gelatin, gum arabic, lactose, starch, magnesium stearate, talc, vegetable oils, polyalkylene-glycols, glycerine and petroleum jelly. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding. The pharmaceutical preparations can be made up in any conventional form including a solid form for oral administration such as tablets, capsules, pills, powders, granules, and rectal suppositories. The pharmaceutical preparations may be sterilized and/or may contain adjuvants such as preservatives, stabilizers, wetting agents, emulsifiers, salts for varying the osmotic pressure and/or buffers.

The compositions of the invention can also be administered to a patient in accordance with the invention by topical (including transdermal, buccal or sublingual), or parenteral (including intraperitoneal, subcutaneous, intravenous, intradermal or intramuscular injection) routes.

The composition may comprise other active agents which may be one to three other antimalarial agents selected from the group comprising atovaquone, chloroquine, amodiaquine, mefloquine, ferroquine, artemisinin and the related peroxans from the pharmaceutical market like artesunate, arteether and artemether, menadione, methylene blue, proguanil, cycloguanil, chlorproguanil, pyrimethamine, primaquine, piperaquine, fosmidomycin, halofantrine, dapsone, trimethoprim, sulfamethoxazole, sulfadoxine, ascorbate, for a simultaneous, separated or sequential, or administration.

The composition may comprise other active agents which may be one to three other antischistosomal agents selected from the group comprising praziquantel, atovaquone, artemisinin and the related peroxans from the pharmaceutical market like artesunate, arteether and artemether, oxamniquine, dehydroemetine dichlorhydrate, emetine camsilate, emetine chlorhydrate, oltipraz, hycanthone mesilate, lucanthone chlorhydrate, ferroquine, ascorbate, for a simultaneous, separated or sequential, or administration.

A further object of the invention is a process for preparing compounds of formula (I):

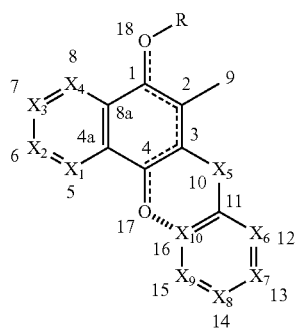

(I)

wherein:
either $X_1$, $X_2$, $X_3$ and $X_4$ represent all carbon atoms,
either one of $X_1$, $X_2$, $X_3$ and $X_4$ represents a nitrogen atom and the three others represent carbon atoms,
either $X_1$ and $X_4$ represent a nitrogen atom and $X_2$ and $X_3$ both represent carbon atoms,
the bond - - - - - between O in position 17 and $X_{10}$ represents no bond or a single bond,
the bond ≈ represents either a single bond or a double bond,
$X_5$ represents CO or $CH_2$ or CHOH,
$X_6$, $X_7$, $X_8$, $X_9$ and $X_{10}$ represent all carbon atoms or one of them represents a nitrogen atom and the four others are carbon atoms,
with the proviso that when the bond - - - - - between O17 and $X_{10}$ represents a single bond, then the bonds ≈ between atoms in positions C1/O18 and C4/O17 are single bonds, the bonds between carbons in positions C1/C2 and C3/C4 are double bonds, the bond between carbons in positions C2/C3 is a simple bond, and R represents a hydrogen atom or an acetyl group and $X_{10}$ is not a nitrogen atom and
$X_1$, $X_2$, $X_3$ and $X_4$ when they are carbon atoms being optionally substituted by:
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$,
—$SCH_2F$,
a trifluoromethyl group,
a trifluoromethoxy group,
$X_6$, $X_7$, $X_8$, $X_9$, $X_{10}$—except when atoms O17 and $X_{10}$ are bound by a simple bond and $X_{10}$ is a quarternary carbon atom—being optionally substituted by:
a hydrogen atom,
a halogen atom,
a hydroxy group,
a linear or branched ($C_1$-$C_4$)alkyl group,
a linear or branched ($C_1$-$C_4$)alkoxy group,
a thio($C_1$-$C_4$)alkoxy group, a pentafluorosulfanyl group,
a trifluoromethyl group,
a trifluoromethoxy group,
a difluoromethoxy group,
a difluoromethyl group,
—COOH,
—COO($C_1$-$C_4$)alkyl group,
—$CONR_1(CH_2)_m CN$, with $R_1$ being a hydrogen atom or a linear or branched ($C_1$-$C_4$)alkyl group and m=1, 2 or 3,
—$CSNR_1(CH_2)_m CN$, with $R_1$ being a hydrogen atom or a linear or branched ($C_1$-$C_4$)alkyl group m=1, 2 or 3,
—$CONR_1$Het with $R_1$ being a hydrogen atom or a linear or branched ($C_1$-$C_4$)alkyl group, Het representing a pyridine-2-yl group, said group optionally substituted by an amino group in -6 or by a —$CONH_2$ group in -5,
—$NO_2$,
—CN,
—$NR_2R_3$ with $R_2$ and $R_3$ representing each independently a hydrogen atom, an amino protecting group selected from the group comprising Boc group and ($C_1$-$C_4$)alkyl group, or $R_2$ and $R_3$ forming with the nitrogen atom which bears them a cyclic group selected from the group comprising morpholine, piperidine, and piperazine groups, said cyclic groups being optionally substituted.
an aryl group or an aryl group substituted by one or several substituents selected from the group comprising a ($C_1$-$C_4$)alkyl group, a —$NO_2$ group, a —$COOR_4$ with $R_4$ selected from a hydrogen atom and a linear or branched ($C_1$-$C_4$)alkyl group, a —$NR_5R_6$ with $R_5$ and $R_6$ independently selected from the group comprising a hydrogen atom and a linear or branched ($C_1$-$C_4$)alkyl group,
a heterocyclic group selected from the group comprising morpholinyl group or piperazinyl group, each of said group being optionally substituted by one or several substituents selected from the group comprising a linear or branched ($C_1$-$C_4$)alkyl group, —$COOCH_2CH_3$, or a group

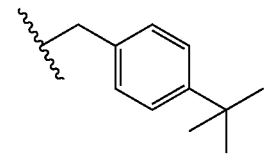 [SMILES: *Cc1ccc(C(C)(C)C)cc1]

said process comprising the step of reacting a compound of formula (II)

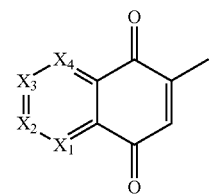

(II)

wherein $X_1$, $X_2$, $X_3$ and $X_4$ are as defined above with a compound of formula (III)

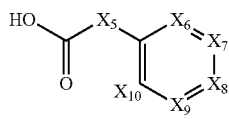

(III)

wherein $X_5$ represents CO or $CH_2$, $X_6$, $X_7$, $X_8$, $X_9$ and $X_{10}$ are as defined above in a Kochi-Anderson reaction to give a compound of formula (Ia)

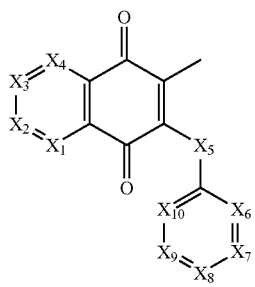

(Ia)

A further object of the invention is a proces further comprising the step of submitting a compound of formula (Ia) as obtained above

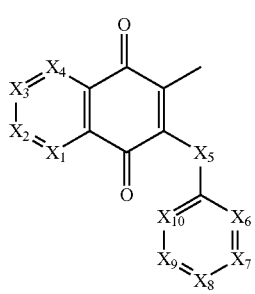

(Ia)

wherein $X_1$, $X_2$, $X_3$, $X_4$, $X_5$, $X_7$, $X_8$, $X_9$ are, as defined above and at least one of $X_6$ and $X_{10}$ bears a leaving group selected from the group comprising F, Cl, Br or OMe, to a reduction into hydronaphthoquinone followed by a intramolecular nucleophilic aromatic substitution to give a compound of formula (Ib)

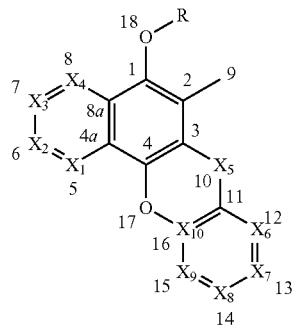

(Ib)

wherein $X_1$, $X_2$, $X_3$, $X_4$, $X_5$, $X_6$, $X_7$, $X_8$, $X_9$ and $X_{10}$ are, as defined above.

The invention has also as an object a process for preparing compounds of formula (Ia1)

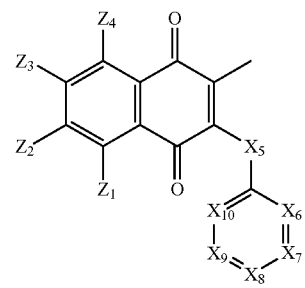

(Ia1)

wherein $X_5$, $X_6$, $X_7$, $X_8$, $X_9$ and $X_{10}$ are as defined above and $Z_1$, $Z_2$, $Z_3$ and $Z_4$ are selected from the group comprising
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$
—$SCH_2F$,
a trifluoromethyl group,
a trifluoromethoxy group,
wherein a compound of formula (IIa1)

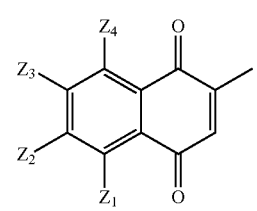

(IIa1)

wherein $Z_1$, $Z_2$, $Z_3$ and $Z_4$ are as defined above, is prepared by treating a compound of formula (IV)

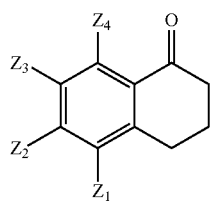

(IV)

with a base in a solvent like for example toluene in the presence of an alkylformate like ethylformate to yield a compound of formula (V)

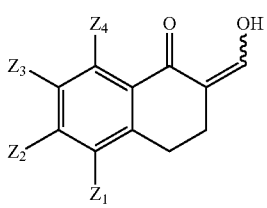

(V)

which is oxidised for example by 2,3-dichloro-5,6-dicyano-1,4-benzoquinone (or DDQ) in a solvent like dioxane to give a compound of formula (VI)

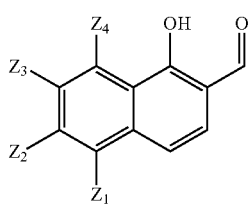

(VI)

which is treated with ethylchloroformate in a solvent like for example tetrahydrofurane (THF) in the presence of a base like for example triethylamine and of sodium tetrahydroboride to give a compound of formula (VII)

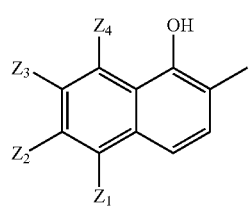

(VII)

which is treated by oxidation for example with phenyliodonium diacetate (PIDA) or [Bis(trifluoroacetoxy)iodo]benzene (PIFA) or Oxone®, in a solvent to yield a compound of formula (IIa1), said compound of formula (IIa1) being reacted in a Kochi-Anderson reaction with a compound of formula (III) as defined above to yield a compound of formula (Ia1).

The invention has also as an object a process for preparing compounds of formula (Ia1)

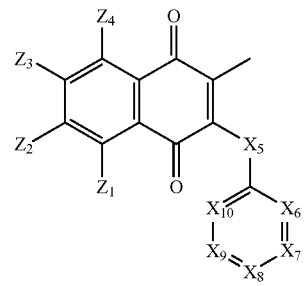

(Ia1)

wherein $X_5$, $X_6$, $X_7$, $X_8$, $X_9$ and $X_{10}$ are as defined above and $Z_1$, $Z_2$, $Z_3$ and $Z_4$ are selected from the group comprising a hydrogen atom, a halogen atom, a hydroxy group, a triflate group, a phosphate group, a linear or branched ($C_1$-$C_4$)alkyl group, a linear or branched ($C_1$-$C_4$)alkoxy group, a thio($C_1$-$C_4$)alkoxy group, a pentafluorosulfanyl group,

—$SCF_3$

—$SCH_2F$, a trifluoromethyl group, a trifluoromethoxy group, wherein a compound of formula (IIa1)

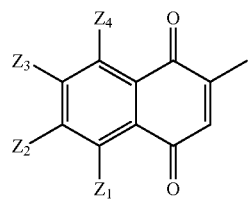

(IIa1)

wherein $Z_1$, $Z_2$, $Z_3$ and $Z_4$ are as defined above is prepared by treating a compound of formula (VIII)

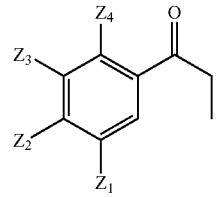

(VIII)

with bromine in an acidic medium to yield a compound of formula (IX)

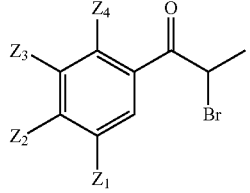

(IX)

which is submitted to a nucleopilic substitution to yield a compound of formula (X)

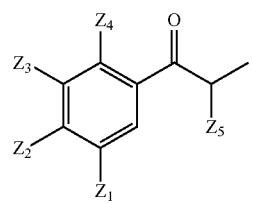

(X)

with $Z_5$ representing a xanthate group, like S(S)OEt, S(S)OMe or S(S)OPr which is submitted to a radical reaction to yield a compound of formula (XI)

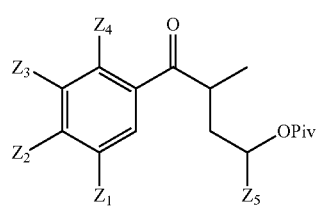

(XI)

which is cyclised into a tetralone of formula (XII)

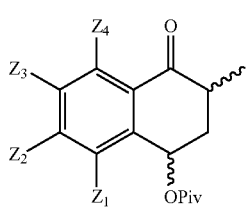

(XII)

which is deshydrated to give a compound of formula (VII)

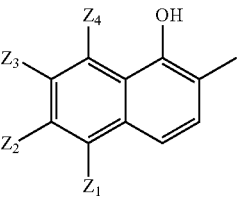

(VII)

which is treated by oxidation for example with phenyliodonium diacetate (PIDA) or [Bis(trifluoroacetoxy)iodo]benzene (PIFA) or Oxone® in a solvent like a mixture of water and acetonitrile to yield a compound of formula (IIa1) said compound of formula (IIa1) being reacted in a Kochi-Anderson reaction with a compound of formula (III) as defined above to yield a compound of formula (Ia1).

The invention has also as an object a process for preparing compounds of formula (Ia2)

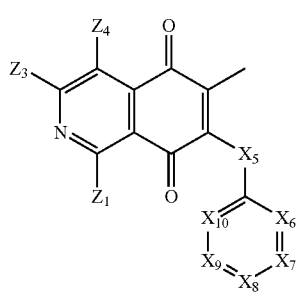

(Ia2)

wherein $X_5$, $X_6$, $X_7$, $X_8$, $X_9$ and $X_{10}$ are as defined above and $Z_1$, $Z_3$ and $Z_4$ are selected from the group comprising
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$
—$SCH_2F$,
a trifluoromethyl group,
a trifluoromethoxy group,
wherein a compound of formula (IIa2)

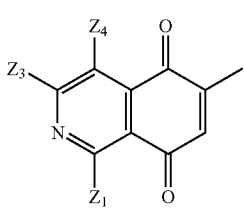

(IIa2)

wherein $Z_1$, $Z_3$ and $Z_4$ are as defined above, is prepared by reacting a compound of formula (XIII)

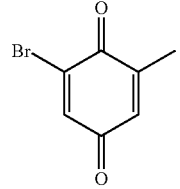
(XIII)

with a compound of formula (XVI)

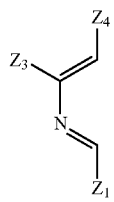
(XVI)

wherein $Z_1$, $Z_3$ and $Z_4$ are as defined above,
to yield a compound of formula (IIa2), said compound of formula (IIa2) being reacted in a Kochi-Anderson reaction with a compound of formula (III) as defined above to yield a compound of formula (Ia2).

The invention has also as an object a process for preparing compounds of formula (Ia3)

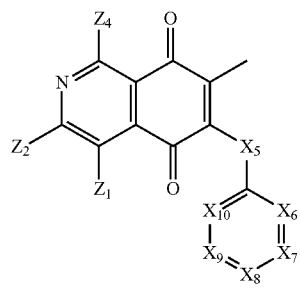
(Ia3)

wherein $X_5$, $X_6$, $X_7$, $X_8$, $X_9$ and $X_{10}$ are as defined above and $Z_1$, $Z_3$ and $Z_4$ are selected from the group comprising
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$
—$SCH_2F$,
a trifluoromethyl group,
a trifluoromethoxy group,
wherein a compound of formula (IIa3)

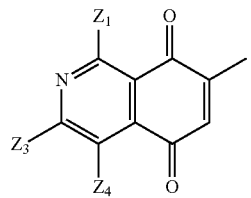
(IIa3)

wherein $Z_1$, $Z_2$ and $Z_4$ are as defined above is prepared by reacting a compound of formula (XIV)

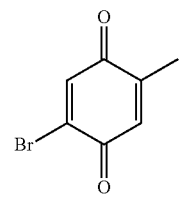
(XIV)

with a compound of formula (XVII)

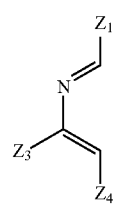
(XVII)

wherein $Z_1$, $Z_3$ and $Z_4$ are as defined above,
to yield a compound of formula (IIa3), said compound of formula (IIa3) being reacted in a Kochi-Anderson reaction with a compound of formula (III) as defined above to yield a compound of formula (Ia3).

The invention has also as an object a process for preparing compounds of formula (Ia4)

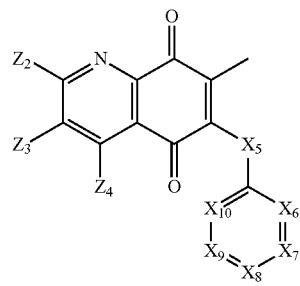
(Ia4)

wherein $X_5$, $X_6$, $X_7$, $X_8$, $X_9$ and $X_{10}$ are as defined above and $Z_2$, $Z_3$ and $Z_4$ are selected from the group comprising
a hydrogen atom,
a halogen atom,
a hydroxy group,
a triflate group,
a phosphate group,
a linear or branched ($C_1$-$C_4$)alkyl group, a linear or branched $(C_1$-$C_4)$alkoxy group,
a thio$(C_1$-$C_4)$alkoxy group,
a pentafluorosulfanyl group,
—$SCF_3$
—$SCH_2F$,
a trifluoromethyl group,
a trifluoromethoxy group,
wherein a compound of formula (IIa4)

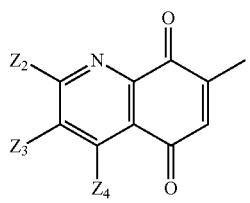
(IIa4)

is prepared by reacting a compound of formula (XIV)

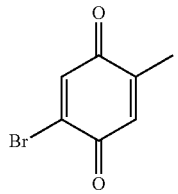
(XIV)

with a compound of formula (XVIII)

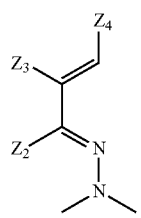
(XVIII)

wherein $Z_2$, $Z_3$ and $Z_4$ are as defined above, said compound of formula (IIa4) being reacted in a Kochi-Anderson reaction with a compound of formula (III) as defined above to yield a compound of formula (Ia4).

The invention has also as an object a process for preparing compounds of formula (Ia6)

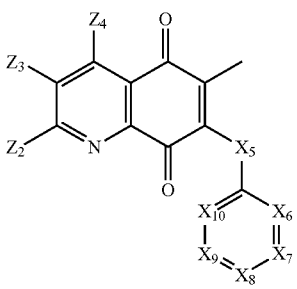
(Ia6)

wherein $X_5$, $X_6$, $X_7$, $X_8$, $X_9$ and $X_{10}$ are as defined above and $Z_2$, $Z_3$ and $Z_4$ are selected from the group comprising a hydrogen atom,
a halogen atom,
a hydroxy group,
a triflate group,
a phosphate group,
a linear or branched $(C_1$-$C_4)$alkyl group,
a linear or branched $(C_1$-$C_4)$alkoxy group,
a thio$(C_1$-$C_4)$alkoxy group,
a pentafluorosulfanyl group,
—$SCF_3$
—$SCH_2F$,
a trifluoromethyl group,
a trifluoromethoxy group,
wherein a compound of formula (IIa6)

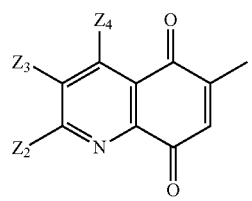
(IIa6)

wherein $Z_2$, $Z_3$ and $Z_4$ are as defined above is prepared by reacting a compound of formula (XIII)

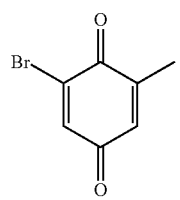
(XIII)

with a compound of formula (XVIII)

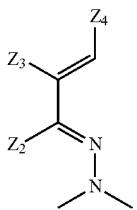
(XVIII)

wherein $Z_2$, $Z_3$ and $Z_4$ are as defined above, said compound of formula (IIa6) being reacted in a Kochi-Anderson reaction with a compound of formula (III) as defined above to yield a compound of formula (Ia6).

The invention has also as an object a process for preparing compounds of formula (Ia5)

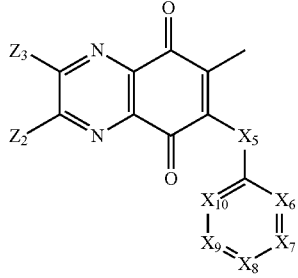

(Ia5)

wherein $X_5$, $X_6$, $X_7$, $X_8$, $X_9$ and $X_{10}$ are as defined before and $Z_2$ and $Z_3$ which are the same are selected from the group comprising

- a hydrogen atom,
- a halogen atom,
- a hydroxy group,
- a triflate group,
- a phosphate group,
- a linear or branched ($C_1$-$C_4$)alkyl group,
- a linear or branched ($C_1$-$C_4$)alkoxy group,
- a thio($C_1$-$C_4$)alkoxy group,
- a pentafluorosulfanyl group,
- —$SCF_3$
- —$SCH_2F$,
- a trifluoromethyl group,
- a trifluoromethoxy group, wherein a compound of formula (IIa5)

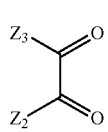

(IIa5)

wherein $Z_2$ et $Z_3$ which are the same are as defined above, is prepared by reacting a compound of formula (XIX)

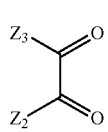

(XIX)

wherein $Z_2$ and $Z_3$ which are the same are as defined above, with a compound of formula (XX)

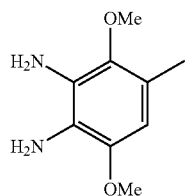

(XX)

said compound of formula (IIa5) being reacted in a Kochi-Anderson reaction with a compound of formula (III) as defined above to yield a compound of formula (Ia5).

The invention has also as an object a process for preparing a compound of formula (Ib1)

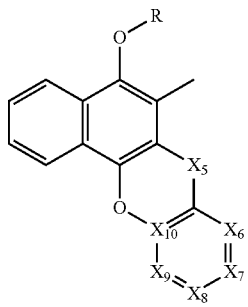

(Ib1)

wherein $X_5$ is CO, $X_6$, $X_7$, $X_8$, $X_9$, $X_{10}$ and R are as defined above wherein a 2-bromo-1,4-dimethoxy-3-methylnaphtalene of formula (XXI)

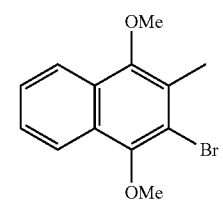

(XXI)

is reacted with a compound of formula (XXII)

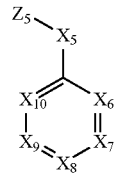

(XXII)

wherein $X_5$ is CO, $X_7$, $X_8$, $X_9$, are as defined before, $X_{10}$ and $X_6$ bear a leaving group selected from the group comprising F, Cl, Br and OMe and $Z_5$ represents an halogen atom or an alkoxy group, in particular a methoxy group.

in presence of a lithium base derivative to yield a compound of formula (XXIII)

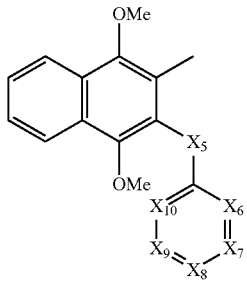

(XXIII)

which is treated with $BBr_3$ and a base like $K_2CO_3$ medium to give a compound of Another object of the invention is a process for preparing compounds of formula (I):

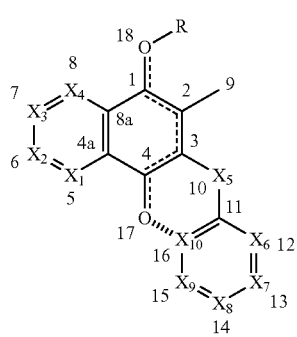

(I)

wherein:
either $X_1$, $X_2$, $X_3$ and $X_4$ represent all carbon atoms,
either one of $X_1$, $X_2$, $X_3$ and $X_4$ represents a nitrogen atom and the three others represent carbon atoms,
either $X_1$ and $X_4$ represent a nitrogen atom and $X_2$ and $X_3$ both represent carbon atoms,
the bond - - - - - between O in position 17 and $X_{10}$ represents no bond or a single bond,
the bond ═══ represents either a single bond or a double bond,
$X_5$ represents CO or $CH_2$ or CHOH,
$X_6$, $X_7$, $X_8$, $X_9$ and $X_{10}$ represent all carbon atoms or one of them represents a nitrogen atom and the four others are carbon atoms,
 i) when the bond - - - - - between O17 and $X_{10}$ represents a single bond, then the bonds ═══ between atoms in positions C1/O18 and C4/O17 are single bonds, the bonds between carbons in positions C1/C2 and C3/C4 are double bonds, the bond between carbons in positions C2/C3 is a simple bond, and R represents a hydrogen atom or an acetyl group and $X_{10}$ is not a nitrogen atom and
 ii) when the bond - - - - - between O17 and $X_{10}$ represents no bond, then R does not exist and the bonds ═══ between atoms C1/O18 and C4/O17 are double bonds, the bonds between carbons in positions C1/C2 and C3/C4 are simple bonds, the bond between carbons in positions C2/C3 is a double bond, and
$X_1$, $X_2$, $X_3$ and $X_4$ when they are carbon atoms being optionally substituted by:

a hydrogen atom,
a halogen atom,
a hydroxy group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—$SCF_3$,
—$SCH_2F$,
a trifluoromethyl group,
a trifluoromethoxy group,
$X_6$, $X_7$, $X_8$, $X_9$, $X_{10}$—except when atoms O17 and $X_{10}$ are bound by a simple bond and $X_{10}$ is a quarternary carbon atom—being optionally substituted by:
 a hydrogen atom,
 a halogen atom,
 a hydroxy group,
 a linear or branched $(C_1-C_4)$alkyl group,
 a linear or branched $(C_1-C_4)$alkoxy group,
 a thio$(C_1-C_4)$alkoxy group,
 a pentafluorosulfanyl group,
 a trifluoromethyl group,
 a trifluoromethoxy group,
 a difluoromethoxy group,
 a difluoromethyl group,
 —COOH,
 —COO$(C_1-C_4)$alkyl group,
 —$CONR_1(CH_2)_m CN$, with $R_1$ being a hydrogen atom or a linear or branched $(C_1-C_4)$alkyl group and m=1, 2 or 3,
 —$CSNR_1(CH_2)_m CN$, with $R_1$ being a hydrogen atom or a linear or branched $(C_1-C_4)$alkyl group m=1, 2 or 3,
 —$CONR_1$Het with $R_1$ being a hydrogen atom or a linear or branched $(C_1-C_4)$alkyl group, Het representing a pyridine-2-yl group, said group optionally substituted by an amino group in -6 or by a —$CONH_2$ group in -5,
 —$NO_2$,
 —CN,
 —$NR_2R_3$ with $R_2$ and $R_3$ representing each independently a hydrogen atom, an amino protecting group selected from the group comprising Boc group and $(C_1-C_4)$alkyl group, or $R_2$ and $R_3$ forming with the nitrogen atom which bears them a cyclic group selected from the group comprising morpholine, piperidine and piperazine groups, said cyclic groups being optionally substituted.
an aryl group or an aryl group substituted by one or several substituents selected from the group comprising a $(C_1-C_4)$alkyl group, a —$NO_2$ group, a —$COOR_4$ with $R_4$ selected from a hydrogen atom and a linear or branched $(C_1-C_4)$alkyl group, a —$NR_5R_6$ with $R_5$ and $R_6$ independently selected from the group comprising a hydrogen atom and a linear or branched $(C_1-C_4)$alkyl group,
a heterocyclic group selected from the group comprising morpholinyl group or piperidinyl or piperazinyl group, each of said group being optionally substituted by one or several substituents selected from the group comprising a linear or branched $(C_1-C_4)$alkyl group, —$COOCH_2CH_3$, or a group

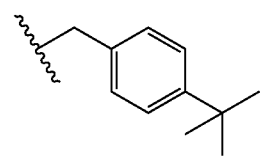 [SMILES: *Cc1ccc(C(C)(C)C)cc1]

said process comprising the step of reacting a compound of formula (II)

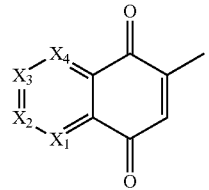

wherein $X_1$, $X_2$, $X_3$ and $X_4$ are as defined above with a compound of formula (III)

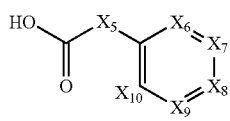

wherein $X_5$ is CO or $CH_2$, $X_6$, $X_7$, $X_8$, $X_9$ and $X_{10}$ are as defined above in a Kochi-Anderson reaction to give a compound of formula (Ia)

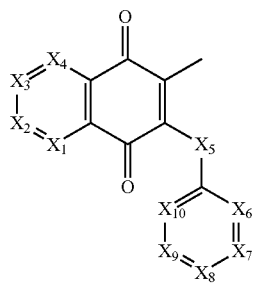

The compounds of formula (Ia) are polysubstituted naphthoquinones and are a subgroup of compounds of formula (I).

In an advantageous embodiment according to the invention, the process further comprises the step of submitting a compound of formula (Ia)

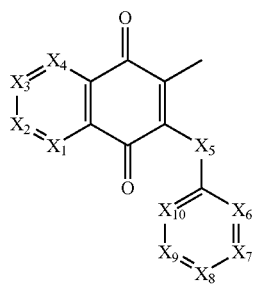

wherein $X_1$, $X_2$, $X_3$, $X_4$, $X_5$, $X_7$, $X_8$, $X_9$ are as defined above and at least one of $X_6$ and $X_{10}$ bears a leaving group selected from the group comprising F, Cl, Br or OMe, to a reduction into hydronaphthoquinone followed by a intramolecular nucleophilic aromatic substitution to give a compound of formula (Ib)

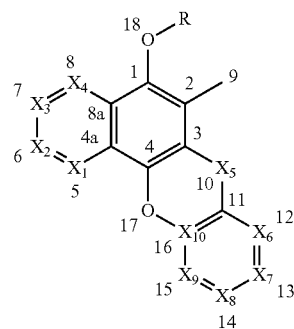

Compounds of formula (Ib) are called benz[c]xanthen-7-ones (shortened as benzxanthones) and are a subgroup of compounds of formula (I).

In another embodiment of the invention the process is used for preparing compounds of formula (Ia1)

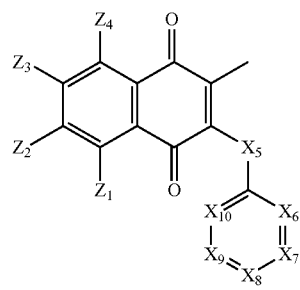

wherein $X_5$, $X_6$, $X_7$, $X_8$, $X_9$ and $X_{10}$ are as defined above and $Z_1$, $Z_2$, $Z_3$ and $Z_4$ are selected from the group comprising
a hydrogen atom,
a halogen atom,
a hydroxy group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—$SCF_3$,
—$SCH_2F$,
a trifluoromethyl group,
a trifluoromethoxy group,
wherein a compound of formula (IIa1)

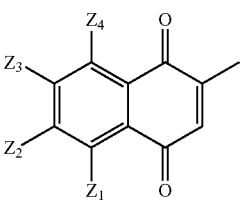

wherein $Z_1$, $Z_2$, $Z_3$ and $Z_4$ are as defined above, is prepared by treating a compound of formula (IV)

(IV)

[structure of formula IV: tetralone with Z1, Z2, Z3, Z4 substituents]

with a base in a solvent like for example toluene in the presence of an alkylformate like ethylformate to yield a compound of formula (V)

(V)

[structure of formula V]

which is oxidised for example by 2,3-dichloro-5,6-dicyano-1,4-benzoquinone (or DDQ) in a solvent like dioxane to give a compound of formula (VI)

(VI)

[structure of formula VI]

which is treated with ethylchloroformate in a solvent like for example tetrahydrofurane (THF) in the presence of a base like for example triethylamine and of sodium tetrahydroboride to give a compound of formula (VII)

(VII)

[structure of formula VII]

which is treated by oxidation for example with phenyliodonium diacetate (PIDA) or [Bis(trifluoroacetoxy)iodo]benzene (PIFA) or Oxone®, in a solvent to yield a compound of formula (IIa1), said compound of formula (IIa1) being reacted in a Kochi-Anderson reaction with a compound of formula (III) as defined above to yield a compound of formula (Ia1).

In another embodiment of the invention the process is used for preparing compounds of formula (Ia1)

(Ia1)

[structure of formula Ia1]

wherein $X_5$, $X_6$, $X_7$, $X_8$, $X_9$ and $X_{10}$ are as defined above and $Z_1$, $Z_2$, $Z_3$ and $Z_4$ are selected from the group comprising
  a hydrogen atom,
  a halogen atom,
  a hydroxy group,
  a linear or branched ($C_1$-$C_4$)alkyl group,
  a linear or branched ($C_1$-$C_4$)alkoxy group,
  a thio($C_1$-$C_4$)alkoxy group,
  a pentafluorosulfanyl group,
  —$SCF_3$
  —$SCH_2F$,
  a trifluoromethyl group,
  a trifluoromethoxy group,
wherein a compound of formula (IIa1)

(IIa1)

[structure of formula IIa1]

wherein $Z_1$, $Z_2$, $Z_3$ and $Z_4$ are as defined above is prepared by treating a compound of formula (VIII)

(VIII)

[structure of formula VIII]

with bromine in an acidic medium to yield a compound of formula (IX)

(IX)

[structure of formula IX]

which is submitted to a nucleopilic substitution to yield a compound of formula (X)

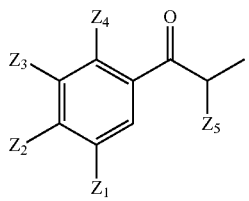
(X)

with $Z_5$ representing a xanthate group, like S(S)OEt, S(S)OMe or S(S)OPr which is submitted to a radical reaction to yield a compound of formula (XI)

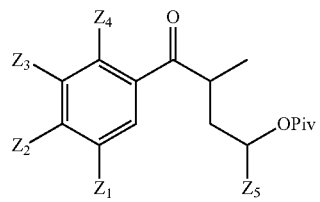
(XI)

which is cyclised into a tetralone of formula (XII)

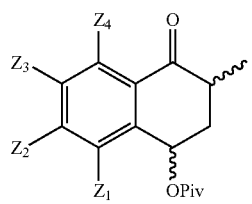
(XII)

which is deshydrated to give a compound of formula (VII)

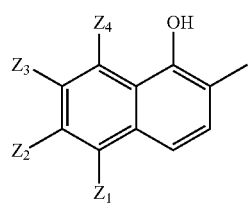
(VII)

which is treated by oxidation for example with phenyliodonium diacetate (PIDA) or [Bis(trifluoroacetoxy)iodo]benzene (PIFA) or Oxone® in a solvent like a mixture of water and acetonitrile to yield a compound of formula (IIa1), said compound of formula (IIa1) being reacted in a Kochi-Anderson reaction with a compound of formula (III) as defined above to yield a compound of formula (Ia1). This route is called the propiophenone route.

In another embodiment of the invention the process is used for preparing compounds of formula (Ia1)

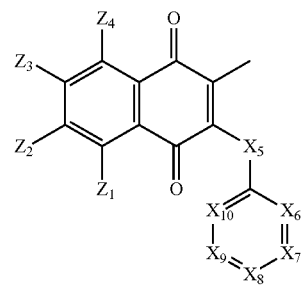
(Ia1)

wherein X5 X6, X7, X8, X9 and X10 are as defined above and Z1, Z2, Z3 and Z4 are selected from the group comprising a hydrogen atom, a halogen atom, a hydroxy group, a triflate group, a phosphate group, a linear or branched (C1-C4)alkyl group, a linear or branched (C1-C4)alkoxy group, a thio(C1-C4)alkoxy group, a pentafluorosulfanyl group,

—SCF$_3$

—SCH$_2$F, a trifluoromethyl group, a trifluoromethoxy group, wherein a compound of formula (IIa1)

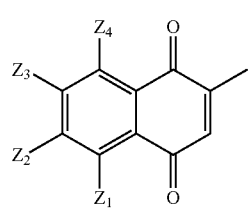
(IIa1)

wherein $Z_1$, $Z_2$, $Z_3$ and $Z_4$ are as defined above is prepared by treating a compound of formula (XIII)

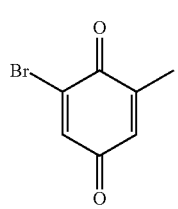
(XIII)

or a compound of formula (XIV)

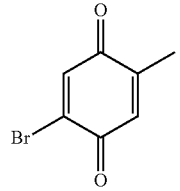
(XIV)

with a compound of formula (XV), pyridine and DDQ or SiO$_2$

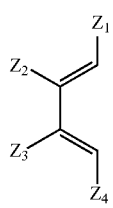
(XV)

wherein $Z_1$, $Z_2$, $Z_3$ and $Z_4$ are as defined above,
to yield a compound of formula (IIa1), said compound of formula (IIa1) being reacted in a Kochi-Anderson reaction with a compound of formula (III) as defined above to yield a compound of formula (Ia1). This route is called the Diels-Alder route.

In another embodiment of the invention the process is used for preparing compounds of formula (Ia2)

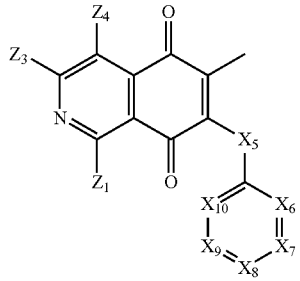
(Ia2)

wherein $X_5$, $X_6$, $X_7$, $X_8$, $X_9$ and $X_{10}$ are as defined above and $Z_1$, $Z_3$ and $Z_4$ are selected from the group comprising
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—SCF$_3$
—SCH$_2$F,
a trifluoromethyl group,
a trifluoromethoxy group, wherein a compound of formula (IIa2)

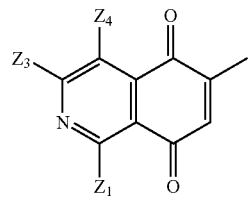
(IIa2)

wherein $Z_1$, $Z_3$ and $Z_4$ are as defined above, is prepared by reacting a compound of formula (XIII)

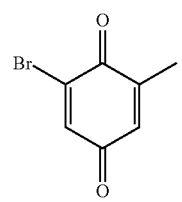
(XIII)

with a compound of formula (XVI)

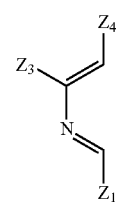
(XVI)

wherein $Z_1$, $Z_3$ and $Z_4$ are as defined above,
to yield a compound of formula (IIa2), said compound of formula (IIa2) being reacted in a Kochi-Anderson reaction with a compound of formula (III) as defined above to yield a compound of formula (Ia2).

Another object of the invention is a process for preparing compounds of formula (Ia3)

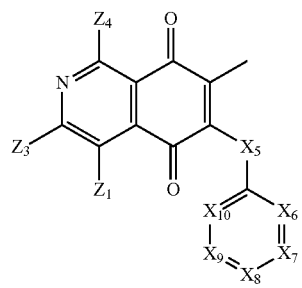
(Ia3)

wherein $X_5$, $X_6$, $X_7$, $X_8$, $X_9$ and $X_{10}$ are as defined above and $Z_1$, $Z_3$ and $Z_4$ are selected from the group comprising
a hydrogen atom,
a halogen atom,
a hydroxy group,
a triflate group, a phosphate group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—$SCF_3$
—$SCH_2F$,
a trifluoromethyl group,
a trifluoromethoxy group,
wherein a compound of formula (IIa3)

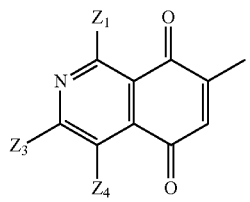
(IIa3)

wherein $Z_1$, $Z_2$ and $Z_4$ are as defined above is prepared by reacting a compound of formula (XIV)

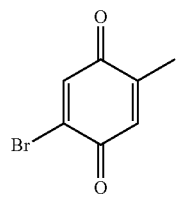
(XIV)

with a compound of formula (XVII)

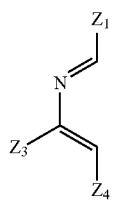
(XVII)

wherein $Z_1$, $Z_3$ and $Z_4$ are as defined above, to yield a compound of formula (IIa3), said compound of formula (IIa3) being reacted in a Kochi-Anderson reaction with a compound of formula (III) as defined above to yield a compound of formula (Ia3).

In another embodiment of the invention, the process is used for preparing compounds of formula (Ia4)

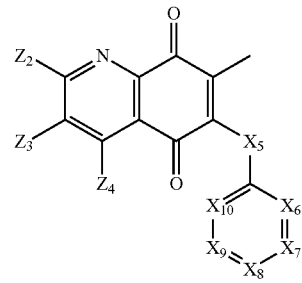
(Ia4)

wherein $X_5$, $X_6$, $X_7$, $X_8$, $X_9$ and $X_{10}$ are as defined above and $Z_2$, $Z_3$ and $Z_4$ are selected from the group comprising
a hydrogen atom,
a halogen atom,
a hydroxy group,
a triflate group,
a phosphate group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—$SCF_3$
—$SCH_2F$,
a trifluoromethyl group,
a trifluoromethoxy group,
wherein a compound of formula (IIa4)

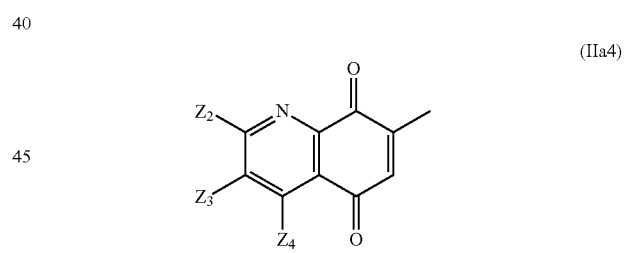
(IIa4)

is prepared by reacting a compound of formula (XIV)

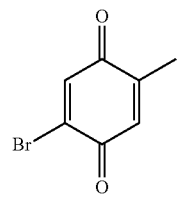
(XIV)

with a compound of formula (XVIII)

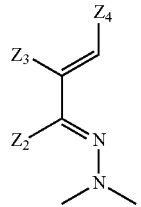
(XVIII)

wherein $Z_2$, $Z_3$ and $Z_4$ are as defined above, said compound of formula (IIa4) being reacted in a Kochi-Anderson reaction with a compound of formula (III) as defined above to yield a compound of formula (Ia4).

In another embodiment of the invention, the process is used for preparing compounds of formula (Ia6)

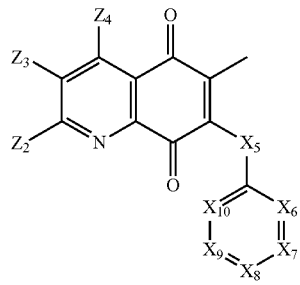
(Ia6)

corresponding to a compound of formula (Ia) wherein $X_1$ is a nitrogen atom, $X_2$, $X_3$ and $X_4$ are carbon atoms and
wherein $X_5$, $X_6$, $X_7$, $X_8$, $X_9$ and $X_{10}$ are as defined above and $Z_2$, $Z_3$ and $Z_4$ are selected from the group comprising
a hydrogen atom,
a halogen atom,
a hydroxy group,
a triflate group,
a phosphate group,
a linear or branched $(C_1\text{-}C_4)$alkyl group,
a linear or branched $(C_1\text{-}C_4)$alkoxy group,
a thio$(C_1\text{-}C_4)$alkoxy group,
a pentafluorosulfanyl group,
—$SCF_3$
—$SCH_2F$,
a trifluoromethyl group,
a trifluoromethoxy group,
wherein a compound of formula (IIa6)

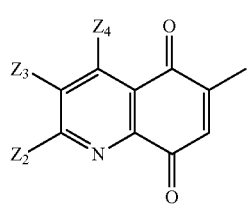
(IIa6)

wherein $Z_2$, $Z_3$ and $Z_4$ are as defined above is prepared by reacting a compound of formula (XIII)

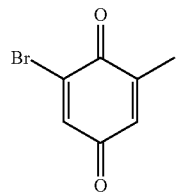
(XIII)

with a compound of formula (XVIII)

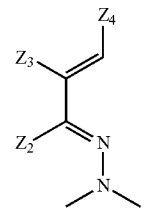
(XVIII)

wherein $Z_2$, $Z_3$ and $Z_4$ are as defined above, said compound of formula (IIa6) being reacted in a Kochi-Anderson reaction with a compound of formula (III) as defined above to yield a compound of formula (Ia6).

In another embodiment of the invention, the process is used for preparing compounds of formula (Ia5)

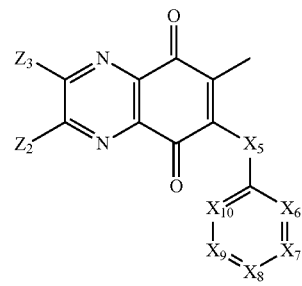
(Ia5)

wherein $X_5$, $X_6$, $X_7$, $X_8$, $X_9$ and $X_{10}$ are as defined before and $Z_2$ and $Z_3$ which are the same are selected from the group comprising
a hydrogen atom,
a halogen atom,
a hydroxy group,
a triflate group,
a phosphate group,
a linear or branched $(C_1\text{-}C_4)$alkyl group,
a linear or branched $(C_1\text{-}C_4)$alkoxy group,
a thio$(C_1\text{-}C_4)$alkoxy group,
a pentafluorosulfanyl group,
—$SCF_3$
—$SCH_2F$,
a trifluoromethyl group,
a trifluoromethoxy group, wherein a compound of formula (IIa5)

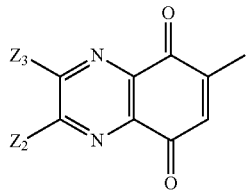
(IIa5)

wherein $Z_2$ et $Z_3$ which are the same are as defined above, is prepared by reacting a compound of formula (XIXI)

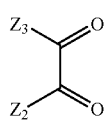
(XIX)

wherein $Z_2$ and $Z_3$ which are the same are as defined above, with a compound of formula (XIII)

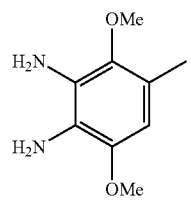
(XX)

said compound of formula (IIa5) being reacted in a Kochi-Anderson reaction with a compound of formula (III) as defined above to yield a compound of formula (Ia5).

In another embodiment of the invention, the process is used for preparing a compound of formula (Ib1)

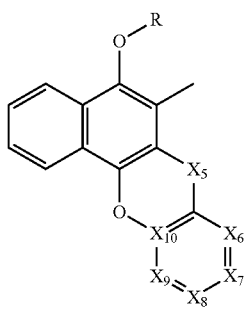
(Ib1)

wherein
$X_5$ is CO, $X_6$, $X_7$, $X_8$, $X_9$, $X_{10}$ and R are as defined before
wherein a 2-bromo-1,4-dimethoxy-3-methylnaphtalene of formula (XXI)

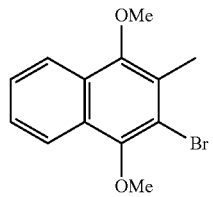
(XXI)

is reacted with a compound of formula (XXII)

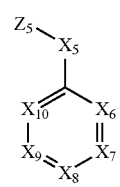
(XXII)

wherein $X_5$ is CO, $X_7$, $X_8$, $X_9$, are as defined before, $X_{10}$ and $X_6$ bear a leaving group selected from the group comprising F, Cl, Br and OMe and $Z_5$ represents an halogen atom or an alkoxy group, in particular a methoxy group.

in presence of a lithium base derivative to yield a compound of formula (XXIII)

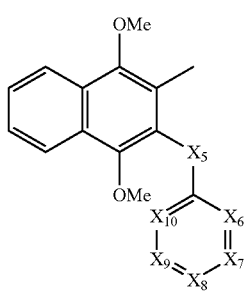
(XXIII)

which is treated with $BBr_3$ and a base like $K_2CO_3$ medium to give a compound of formula (Ib1).

The following examples 1 to 20 and the FIGS. 1 to 5 are intended as illustrations of a few embodiments of the invention.

FIG. 1 illustrates the antimalarial activity of polysubstituted-naphthoquinones, azanaphthoquinones, xanthones and benzxanthone derivatives according to the invention measured according to example 19 against P. falciparum Dd2 and 3D7 strains, both in the radioactive $^3H$ hypoxanthine incorporation assay and in the SYBRgreen assay. In the table, the asterisks (*, , *, ****) referred to the values determined for antimalarial chloroquine used as key control in three disctinct experiments (*, , *, ****). The cells of the table with grey background show structures of compounds disclosed in the international application WO 2009/118327 and used as references in the antimalarial assays.

Figure 2:
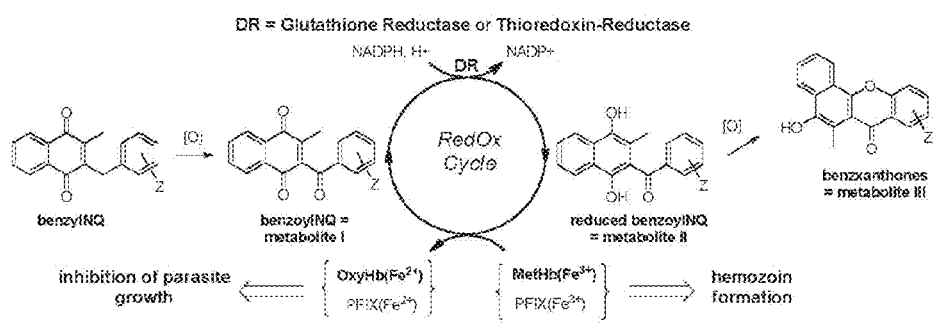

FIG. 2 illutrates the putative cascade of redox reactions generated in situ in the blood-feeding parasites responsible for the antiparasitic action of compounds (simplified in the structure) described in the present application.

Figure 3:
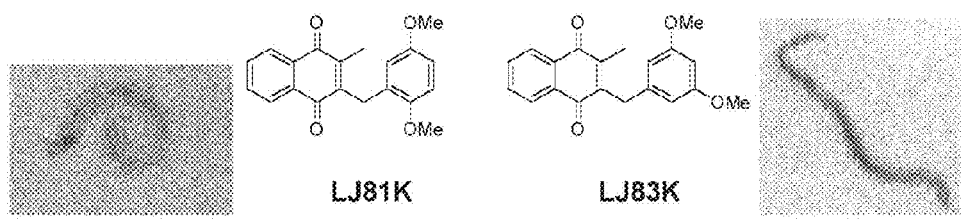

FIG. 3 illustrates profound morphological changes induced by two 3-benzylmenadione derivatives LJ83K (right) and LJ81K despite the weak TGR inhibitory capabilities.

FIG. 4 illustrates the antischistosomal effects of derivatives described in the invention measured according to example 20 against *S. mansoni* worms in cultures. D=100% dead, except when given with a number (% D) which indicated the percentage of dead worms. Addition of hemoglobin (Hb) was applied in order to favor drug metabolism through heme-catalyzed oxidations. Addition of red blood cells (RBC) was applied in order to favor drug metabolism through hemoglobin digestion and heme-catalyzed oxidations. In the table, the term "50/10/5" means that the compounds were tested at 50 µM, 10 µM and 5 µM.

Figure 5:
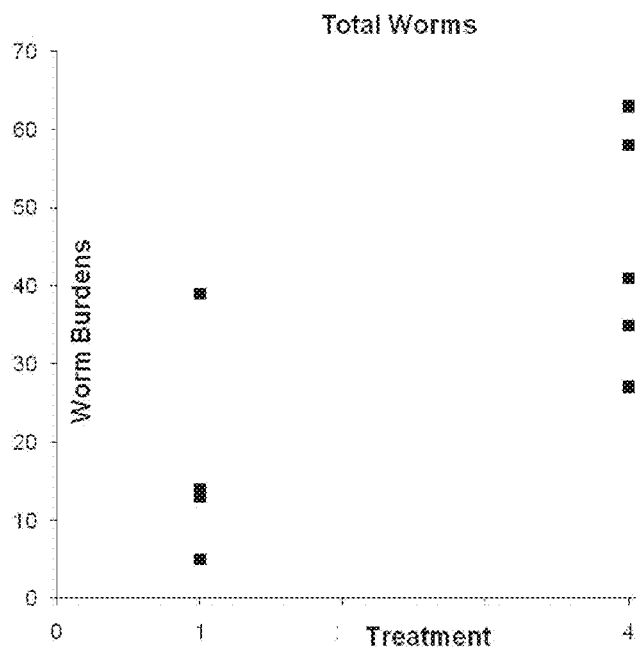

FIG. 5 illustrates the antischistosomal activity of LJ83K described in the invention measured according to example 20 against *S. mansoni* worms-infected mice. All injections were ip: the first injection was carried out six weeks post-infection, the second was performed two days later. Perfusion was 7 days after the second injection date. LJ83K (=P_TM58) was injected twice at 33 mg/kg.

EXAMPLE 1

General Procedure for Alpha-Formylation of Tetralone IV into V

It is based on the work disclosed by B. C. Pearce, R. A. Parker, M. E. Deason, D. D. Dischino, E. Gillepsie, A. A. Qureshi, K. Volk, J. J. Kim Wright *J. Med. Chem.* 1994, 37, 526-541.

A mixture of tetralone IV in toluene (1 eq, 0.45 mmol·mL$^{-1}$) and ethyl formate (2.0 eq) was prepared. The solution was cooled to −78° C. under Argon and mechanically stirred while potassium tert-butoxide (2.0 eq) was added in portions: the solution became milky and pinky. The solution was warmed to −5° C. until TLC monitoring (petroleumether/Et$_2$O: 3/1) indicated the completion of the reaction. The solution was quenched with 10% HCl (the pink solution disappeared) and the mixture extracted with Et$_2$O. The organic phases were dried (brine, MgSO$_4$) and concentrated in vacuo to yield alpha-formyl tetralone (usually as solid compound).

Note: usually the product does not need to be further purified and can be directly engaged in the next step.

1.1. 2-(hydroxymethylene)-6-methoxy-3,4-dihydronaphthalen-1(2H)-one

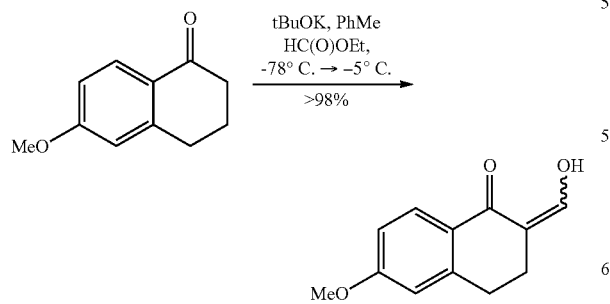

Yield: >98% (light brown solid)

$^1$H NMR (200 MHz, CDCl$_3$): δ=2.51 (t, 2H, J=7.3 Hz), 2.82 (t, 2H, J=7.3 Hz), 3.82 (s, 3H), 6.68 (d, 1H, J=2.4 Hz), 6.82 (dd, 1H, J=8.6 Hz, 2.4 Hz), 7.91 (d, 1H, J=8.6 Hz), ppm The spectroscopic and physical data were identical to those reported in the literature (S. H. Kim, J. R. Gunther, J. A. Katzenellenbogen *Org. Lett.* 2008, 10, 4931-4934).

1.2. 2-(hydroxymethylene)-7-methoxy-3,4-dihydronaphthalen-1(2H)-one

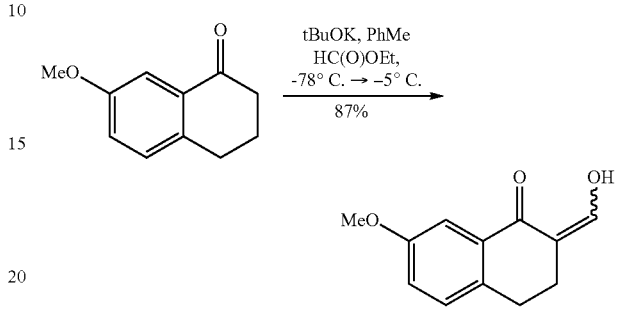

The compound was prepared in the conditions disclosed in 1.1.

Yield: 87% yellow powder $^1$H NMR (300 MHz, CDCl$_3$): δ=2.55-2.50 (m, 2H), 2.82-2.78 (m, 2H), 3.82 (s, 3H), 6.99 (dd, J=8.3 Hz, J=2.8 Hz, 1H), 7.12 (d, J=8.3 Hz, 1H), 7.45 (d, J=2.8 Hz, 1H), 8.11 (d, J=5.4 Hz, 1H), ppm $^{13}$C NMR (75 MHz, CDCl$_3$): δ=23.2 (CH$_2$), 27.9 (CH$_2$), 55.5 (OCH$_3$), 108.9 (CH), 109.4 (CH), 120.3 (CH), 129.1 (CH), 130.1 (C$_{quat}$), 130.1 (C$_{quat}$), 132.5 (C$_{quat}$), 134.1 (C$_{quat}$), 158.7 (C$_{quat}$), 175.5 (CH), 183.2 (C=O) ppm The spectroscopic and physical data were identical to those reported in the literature. (C. Bilger, P. Demerseman, R. Royer *Eur. J. Med. Chem.* 1987, 22, 363-5).

1.3. 2-(hydroxymethylene)-6,7-dimethoxy-3,4-dihydronaphthalen-1(2H)-one

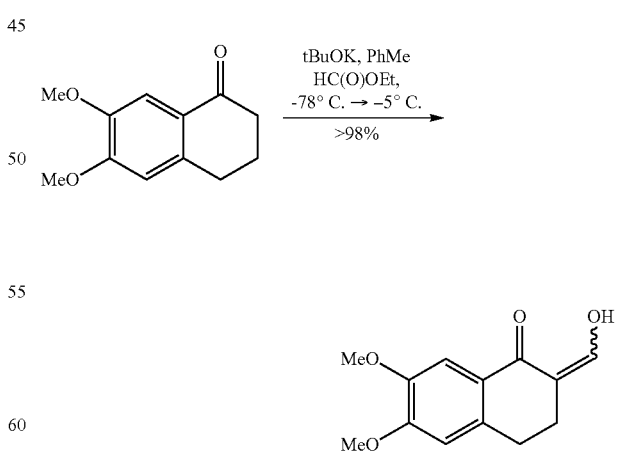

Yield: >98% (light brown solid)

$^1$H NMR (300 MHz, CDCl$_3$): δ=2.38 (t, J=7.1 Hz, 2H), 2.86 (t, J=7.1 Hz, 2H), 3.95 (s, 3H), 3.96 (s, 3H), 6.68 (s, 1H), 6.82 (s, 1H), 7.78 (d, J=7.0 Hz, 1H), ppm $^{13}$C NMR (75 MHz, CDCl$_3$): δ=23.7 (CH$_2$), 28.97 (CH$_2$), 56.1 (2×OCH$_3$), 108.2 (C$_{quat}$), 108.3 (CH), 110.3 (CH), 124.9 (C$_{quat}$), 137.0 (C$_{quat}$), 148.1 (C$_{quat}$), 153.24 (C$_{quat}$), 169.7 (CH), 186.1 (C=O) ppm

1.4. 2-(hydroxymethylene)-7-fluor-3,4-dihydronaphthalen-1(2H)-one

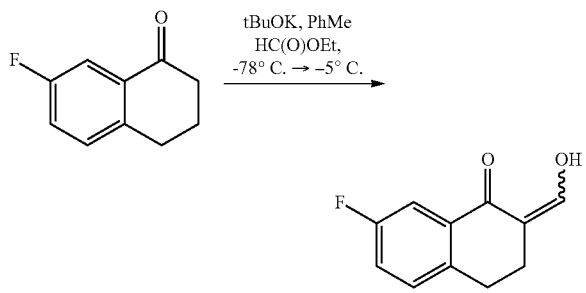

The compound was prepared in the conditions disclosed in 1.1.

Yield: 99% yellow powder $^1$H NMR (300 MHz, CDCl$_3$): δ=2.59 (t, J=7.1 Hz, 2H), 2.88 (t, J=7.1 Hz, 2H), 7.11-7.24 (m, 2H), 7.64 (d, J=9.1 Hz, J=2.8 Hz, 1H), 8.27 (d, J=5.4 Hz, 1H) ppm.

$^{13}$C NMR (75 MHz, CDCl$_3$): δ=22.7 (CH$_2$), 28.0 (CH$_2$), 108.5 (C$_{quat}$) 111.7 (d, J=22.8 Hz, CH), 119.7 (d, J$_{C-F}$=19.4 Hz, CH), 129.5 (d, J$_{C-F}$=7.3 Hz, CH), 133.2 (d, J=7.2 Hz, C$_{quat}$), 137.0 (d, J$_{C-F}$=3.2 Hz, C$_{quat}$), 161.8 (d, J$_{C-F}$=245.0 Hz, C$_{quat}$), 177.6 (CH), 180.8 (C=O) ppm.

EXAMPLE 2

General Procedure for Aromatisation of α-Formyl-Tetralone (V) into (VI)

It is based on the work disclosed by S. H. Kim, et al. (cited above).

To a solution of tetralone (V) in dioxanne (1.0 eq, 0.2 mmol·mL$^{-1}$) was added 2,3-Dichloro-5,6-dicyano-1,4-benzoquinone (or DDQ) (1.0 eq) at room temperature. A white precipitate appeared rapidly. After completion of the reaction (TLC monitoring), the white precipitate was removed by filtration. The filtrate was concentrated under reduced pressure.

The crude was purified by column chromatography (silica gel, eluant cyclohexane/Et$_2$O:3/1).

2.1. 1-hydroxy-6-methoxy-2-naphthaldehyde

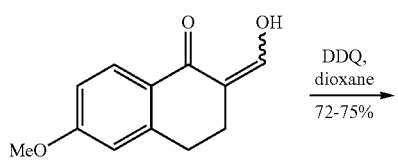

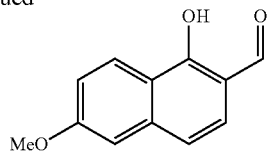

Yield: 72-75%

$^1$H NMR (200 MHz, CDCl$_3$): δ=3.96 (s, 3H), 7.09 (d, 1H, J=2.6 Hz), 7.18 (dd, 1H, J=9.2 Hz, 2.6 Hz), 7.26 (d, 1H, J=8.8 Hz), 7.45 (d, 1H, J=8.8 Hz), 8.35 (d, 1H, J=9.2 Hz), 9.90 (s, 1H), 12.70 (s, 1H) ppm The spectroscopic and physical data were identical to those reported in the literature. (S. H. Kim, et al. (cited above)

2.2. 1-hydroxy-7-methoxy-2-naphthaldehyde

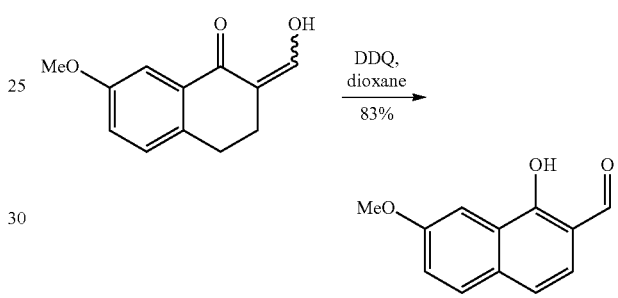

Yield: 83% yellow powder $^1$H NMR (300 MHz, CDCl$_3$): δ=12.40 (s, 1H), 9.81 (s, 1H), 7.56-7.51 (m, 2H), 7.20-7.10 (m, 3H), 3.81 (s, 3H) ppm.

$^{13}$C NMR (75 MHz, CDCl$_3$): δ=55.5 (OCH$_3$), 102.1 (CH), 114.6 (C$_{quat}$), 119.3 (CH), 123.3 (CH), 124.3 (CH), 125.5 (C$_{quat}$), 129.1 (CH), 132.9 (C$_{quat}$), 158.0 (C$_{quat}$), 160.5 (C$_{quat}$), 190.6 (C=O) ppm.

The spectroscopic and physical data were identical to those reported in the literature (C. Bilger, et al, cited above).

2.3. 1-hydroxy-6,7-methoxy-2-naphthaldehyde

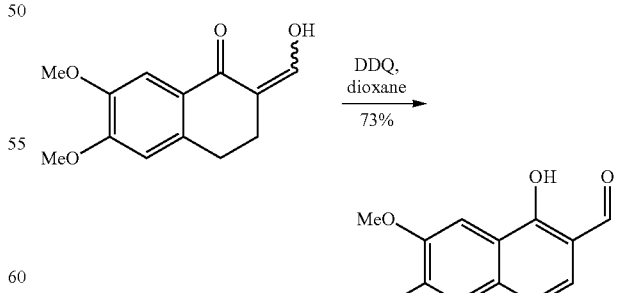

Yield: 73%

$^1$H NMR (300 MHz, CDCl$_3$): δ=3.99 (s, 3H), 4.00 (s, 3H), 7.05 (s, 1H), 7.24 (AB system, J=8.7 Hz, Δν=30.1 Hz, 2H), 7.56 (s, 1H), 9.90 (s, 1H), 12.55 (s, 1H) ppm $^{13}$C NMR (75 MHz, CDCl$_3$: δ=56.0 (OCH$_3$), 56.1 (OCH$_3$), 102.7 (CH), 106.4 (CH), 113.5 (C$_q$), 118.0 (CH), 119.6 (C$_q$), 125.6 (CH), 134.7 (C$_q$), 149.4 (C$_q$), 153.1 (C$_q$), 160.4 (C$_q$) 195.9 (C=O) ppm.

2.4. 1-hydroxy-7-fluor-2-naphthaldehyde

Yield: 87% yellow powder $^1$H NMR (300 MHz, CDCl$_3$): δ=12.54 (s, 1H), 10.01 (s, 1H), 8.04 (dd, J=8.9 Hz J=2.7 Hz) 7.80 (dd, J=8.9 Hz, J=5.4 Hz, 1H), 7.50-7.38 (m, 3H) ppm.

$^{13}$C NMR (75 MHz, CDCl$_3$): δ=108.2 (d, J$_{C-F}$=22.9 Hz, CH), 114.6 (C$_q$), 119.2 (CH) 125.5 (d, J$_{C-F}$=8.8 Hz, C$_{quat}$), 125.8 (d, J$_{C-F}$=2.6 Hz, CH) 130.0 (CH), 130.1 (CH), 134.3 (d, J=1.5 Hz, C$_{quat}$), 160.8 (d, J=247.0 Hz, C$_{quat}$), 160.9 (d, J=1.5 Hz, C$_{quat}$), 196.4 (C=O) ppm.

EXAMPLE 3

General Procedure for Reduction of 2-formyl-1-naphtols VI into VII

It is based on the work disclosed by N. Minami & S. Kijima *Chem. Pharm. Bull.* 1979, 27, 1490-1494.

To a solution of 2-formyl-1-naphtol in tetrahydrofuran (1.0 eq, 1 mmol·mL$^{-1}$) was added triethylamine (1.2 eq). The solution was cooled to 0° C. and then ethyl chloroformate (1.2 eq) was added over a period of 30 min. The solution was left under stirring during 30-60 min (white precipitates formation). The precipitates (triethylamine hydrochloride) were removed by filtration and washed with tetrahydrofuran (twice less than the amount used for the reaction). To the combined filtrates were added, at 5-15° C., an aqueous solution of NaBH$_4$ (4.0 eq, 2.6 M). When the addition was completed, the reaction mixture was stirred at room temperature for 1-2 h, then diluted with water. The solution was cooled to 0° C. and made acidic by the slow addition of aqueous HCl (10%) (FROZING!). The aqueous solution was extracted with Et$_2$O. The organic phases were washed with dilute solution of NaOH (10%), dried (brine, MgSO$_4$) and concentrated in vacuo to yield methylnaphtol (usually as a solid or an oil which crystallized on standing).

Note: usually the product does not need to be further purified and can be directly engaged in the next step.

3.1. 6-methoxy-2-methylnaphthalen-1-ol

Yield: 70%

This compound was reported in literature but was not described: Nowicki, Alexander W.; Turner, Alan B. *Chemistry & Industry* (London, United Kingdom) 1981, 14, 501-2.

$^1$H NMR (300 MHz, CD$_2$Cl$_2$): δ=2.37 (s, 3H), 3.90 (s, 3H), 5.19 (s, 10H), 7.11 (m, 2H), 7.24 (AB system, J=8.1 Hz, Δν=17.1 Hz, 2H), 8.03 (d, J=9.8 Hz, 1H) ppm $^{13}$C NMR (75 MHz, CD$_2$Cl$_2$): δ=15.7 (CH$_3$), 55.8 (OCH$_3$), 106.2 (CH), 114.8 (C$_q$), 118.3 (CH), 119.5 (CH), 120.1 (C$_q$), 123.2 (CH), 130.3 (CH), 135.3 (C$_q$), 149.4 (C$_q$), 158.1 (C$_q$) ppm MS (EI): m/z (%): 188.1 ([M]$^+$, 100), 145.0 (83), 115.0 (62), 189.1 ([M+H]$^+$, 15)

3.2. 7-methoxy-2-methylnaphthalen-1-ol

Yield: 66% yellow powder $^1$H NMR (300 MHz, CDCl$_3$): δ=7.65 (d, J=9.0 Hz, 1H), 7.42 (d, J=2.6 Hz, 1H), 7.30 (d, J=8.4 Hz, 1H), 7.10-7.06 (m, 1H), 3.93 (s, 3H), 2.38 (s, 3H) ppm.

$^{13}$C NMR (75 MHz, CDCl$_3$): δ=157.5 (C$_q$); 147.6 (C$_q$); 129.2 (CH); 129.0 (C$_q$) 126.5 (CH); 125.2 (C$_q$); 120.0 (CH); 118.2 (CH); 116.7 (C$_q$); 99.5 (CH); 55.4 (—OCH$_3$); 15.75 (CH$_3$) ppm.

3.3. 6,7-dimethoxy-2-methylnaphthalen-1-ol

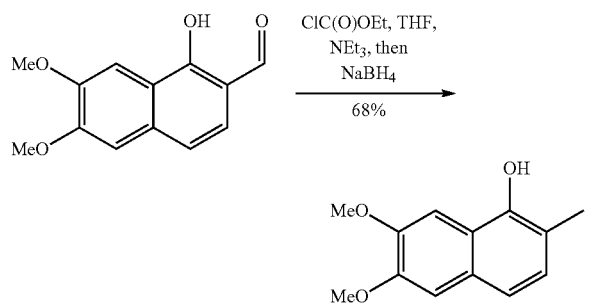

Yield: 68% (yellow powder)

$^1$H NMR (300 MHz, CDCl$_3$): δ=2.37 (s, 3H), 3.90 (s, 3H), 5.19 (s, 10H), 7.11 (m, 2H), 7.24 (AB system, J=8.1 Hz, Δν=17.1 Hz, 2H), 8.03 (d, J=9.8 Hz, 1H) ppm $^{13}$C NMR (75 MHz, CDCl$_3$): δ=15.58 (CH$_3$), 55.8 (OCH$_3$), 55.9 (OCH$_3$), 100.3 (CH), 106.2 (CH), 114.7 (C$_q$), 118.7 (CH), 119.6 (C$_q$), 127.2 (CH), 129.3 (C$_q$), 147.8 (C$_q$), 149.1 (C$_q$), 149.2 (C$_q$) ppm.

3.4. 7-fluor-2-methylnaphthalen-1-ol

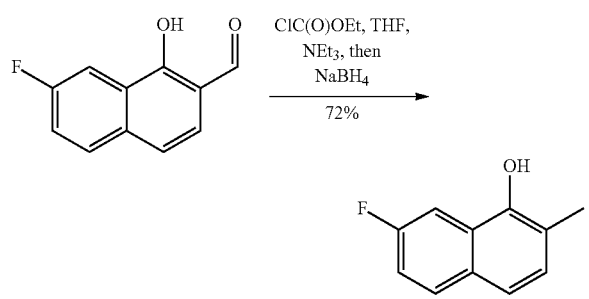

Yield: 72% yellow powder $^1$H NMR (300 MHz, CDCl$_3$): δ=7.90-7.36 (m, 1H), 7.29 (AB system, J=8.5 Hz, Δν=50.7 Hz, 2H) 7.24-7.17 (m, 1H), 2.41 (s, 3H) ppm.

$^{13}$C NMR (75 MHz, CDCl$_3$): δ=162.2 (C$_q$), 148.3 (d, J$_{C-F}$=5.7 Hz, C$_q$), 130.4 (C$_q$), 130.0 (d, J$_{C-F}$=8.9 Hz, CH), 128.2 (d, J$_{C-F}$=2.7 Hz, CH), 125.2 (d, J$_{C-F}$=8.6 Hz, C$_q$), 120.0 (d, J$_{C-F}$=1.1, CH), 117.3 (C$_q$), 115.7 (d, J$_{C-F}$=25.2 Hz, CH), 105.1 (d, J$_{C-F}$=22.4, CH), 15.7 (CH$_3$) ppm.

EXAMPLE 4

General Procedure for Oxidation of Methylnaphtols VII into Menadiones Ia1

It is based on the work from P. Bachu, J. Sperry, M. A. Brimble *Tetrahedron* 2008, 64, 3343-3350

To a stirred solution of naphtol (5.8 mmol, 1 eq) in acetonitrile (70 mL) and water (30 mL) at −5° C. was added [bis(trifluoroacetoxy)iodo]benzene (12.1 mmol, 2.1 eq) portionwise over 20-30 nm. After stirring for 30 nm at −5° C., the reaction mixture was stirred at RT for 1 h. Saturated NaHCO$_3$ solution was added to the reaction orange mixture and the reaction mixture extracted with Et$_2$O (3×120 mL). The combined organic extracts were washed with brine and dried over anhydrous MgSO$_4$. The crude was purified by flash chromatography on silica gel (eluant: hexanes/Et$_2$O).

4.1. 6-methoxy-2-methylnaphthalene-1,4-dione

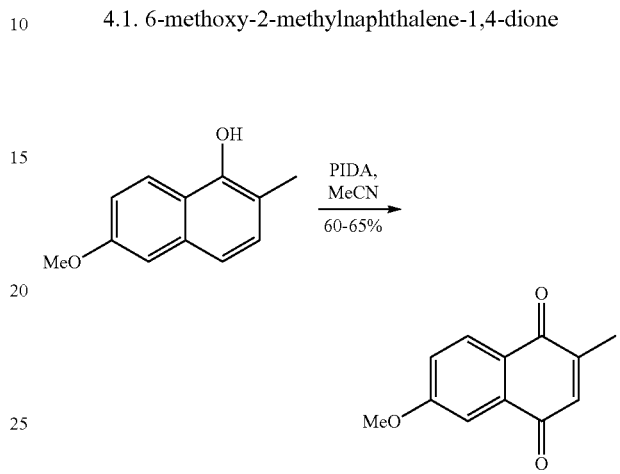

Yield: 60-65%

This compound was shortly described in Sidhu et al. *Indian Journal of Chemistry* 1968, 6, 681-91 m.p. 146-148° C. (Et$_2$O)

$^1$H NMR (300 MHz, CDCl$_3$): δ=2.17 (d, J=1.6 Hz, 3H), 3.93 (s, 3H), 6.78 (d, J=1.6 Hz, 1H), 7.17 (dd, J=8.6 Hz, J=2.7 Hz, 1H), 7.47 (d, J=2.7 Hz, 1H), 8.02 (d, J=8.6 Hz, 1H) ppm $^{13}$C NMR (75 MHz, CDCl$_3$): δ=16.5 (CH$_3$), 55.9 (OCH$_3$), 109.3 (CH), 120.2 (CH), 125.8 (C$_{quat}$), 129.0 (CH), 134.3 (C$_{quat}$), 135.2 (CH), 148.5 (C$_{quat}$), 164.0 (C$_{quat}$), 184.6 (C=O), 185.1 (C=O)

MS (EI):m/z (%): 202.1 ([M]$^+$, 100), 174.0 (29), 203.1 ([M+H]$^+$, 13):

elemental analysis calcd for C$_{12}$H$_{10}$O$_3$ (%) C, 71.28; H, 4.98. Found: C, 71.16; H, 5.05.

4.2. 6-methyl-2-methylnaphthalene-1,4-dione

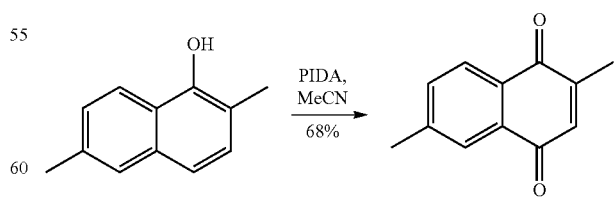

Yield: 68% yellow powder $^1$H NMR (300 MHz, CDCl$_3$): δ=7.99 (d, J=7.9 Hz, 1H), 7.85 (s, 1H), 7.52 (d, J=7.9 Hz, 1H), 6.81 (q, J=1.6 Hz, 1H), 2.49 (s, 3H), 2.19 (d, J=1.6 Hz, 3H) ppm $^{13}$C NMR (75 MHz, CDCl$_3$): δ=185.4 (C=O), 185.2 (C=O), 148.2 (C$_{quat}$), 144.7 (C$_{quat}$), 135.5 (CH), 135.0 (C$_{quat}$), 134.3 (CH), 132.2 (C$_{quat}$), 126.7 (CH), 126.4 (CH), 21.8 (CH$_3$), 16.5 (CH$_3$) ppm

4.3. 7-methoxy-2-methylnaphthalene-1,4-dione

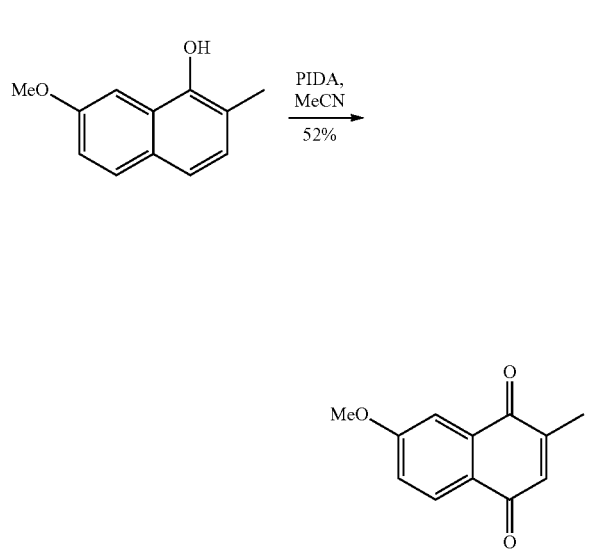

Yield: 52% yellow powder $^1$H NMR (300 MHz, CDCl$_3$): δ=8.03 (d, J=2.7 Hz, 1H), 7.56 (d, J=2.7 Hz, 1H), 7.21 (dd, J=8.6 Hz, J=2.7 Hz, 1H), 6.8 (q, J=1.6 Hz, 1H), 3.97 (s, 3H), 2.2 (d, J=1.6 Hz, 3H) ppm $^{13}$C NMR (75 MHz, CDCl$_3$): δ=$^{13}$C NMR (75 MHz, CDCl$_3$): δ=185.7 (C=O), 184.2 (C=O), 163.9 (C$_{quat}$), 147.6 (C$_{quat}$), 135.9 (CH), 134.1 (C$_{quat}$), 128.5 (CH), 125.8 (C$_{quat}$), 120.1 (CH), 109.9 (CH), 55.9 (OCH$_3$), 16.4 (CH$_3$) ppm.

MS (EI):m/z (%): 202.1 ([M]$^+$, 100)

elemental analysis calcd for C$_{12}$H$_{10}$O$_3$ (%) C, 71.28; H, 4.98. Found: C, 71.35; H, 4.90.

4.4. 6-fluoro-2-methylnaphthalene-1,4-dione

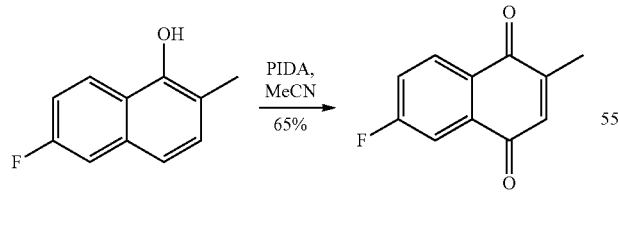

Yield: 65%

$^1$H NMR (200 MHz, CDCl$_3$): δ=2.22 (d, J=1.4 Hz, 3H), 6.88 (d, J=1.4 Hz, 1H), 7.72 (dd, 8.5 Hz, J=2.7 Hz, 1H), 7.40 (ddd, J=8.5 Hz, J$_{H-F}$=8.1 Hz, J=2.7 Hz, 1H) 8.16 (dd, J=8.5 Hz, J$_{H-F}$=5.3 Hz, 1H) ppm $^{13}$C NMR (75 MHz, CDCl$_3$): δ=184.2 (C=O), 183.7 (C=O), 166.3 (d, J$_{C-F}$=260.5 Hz, C$_q$), 148.5 (C$_q$), 135.6 (CH), 134.9 (d, J$_{C-F}$=8.0 Hz, C$_q$), 129.8 (d, J$_{C-F}$=8.7 Hz, CH), 125.6 (C$_q$), 120.7 (d, J$_{C-F}$=22.2 Hz, CH), 112.8 (d, J$_{C-F}$=23.7 Hz, CH), 16.5 (CH$_3$) ppm.

4.5. 6-chloro-2-methylnaphthalene-1,4-dione

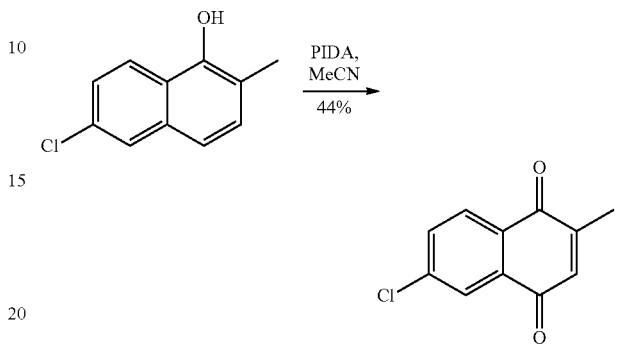

Yield: 44% yellow powder m.p. (hexane/ethyl acetate): 104-105° C.

$^1$H NMR (400 MHz, CDCl$_3$): δ=8.06 (d, J=8.6 Hz, 1H), 8.04 (d, J=2.2 Hz, 1H), 7.68 (dd, J=8.6 Hz, J=2.2 Hz, 1H), 6.86 (q, J=1.5 Hz, 1H), 2.21 (d, J=1.5 Hz, 3H) ppm $^{13}$C NMR (100 MHz, CDCl$_3$) δ=16.5 (CH$_3$), 126.3 (CH), 128.4 (CH), 130.4 (C$_{quat}$), 133.4 (C$_{quat}$), 133.7 (CH), 135.5 (CH), 140.7 (C$_{quat}$), 148.6 (C$_{quat}$), 183.8 (C=O), 184.6 (C=O)

MS (EI):m/z (%): 206.0 ([M]$^+$, 100), 207.1 ([M+H]$^+$, 15), 191.0 ([M-CH$_3$]$^+$, 5)

elemental analysis calcd for C$_{11}$H$_7$O$_2$Cl (%) C, 63.40; H, 3.41. Found C, 63.11; H, 3.49.

4.6. 6,7-dimethoxy-2-methylnaphthalene-1,4-dione

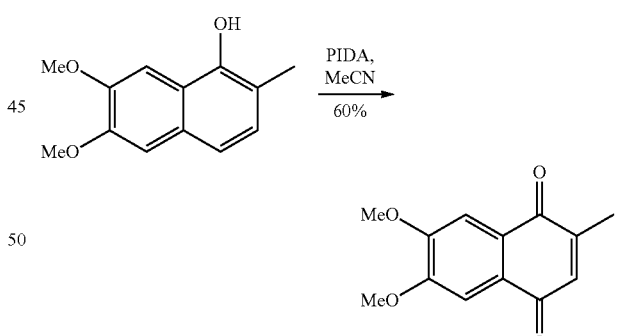

Yield: 60% orange powder m.p. (hexane/ethyl acetate): 183° C. dec.

$^1$H NMR (300 MHz, CDCl$_3$): δ=2.17 (d, J=1.5 Hz, 3H), 4.02 (s, 3H), 4.04 (s, 3H), 6.74 (q, J=1.5 Hz, 1H), 7.48 (s, 1H), 7.52 (s, 1H).

$^{13}$C NMR (75 MHz, CDCl$_3$) δ=16.6, 56.7 (2×OCH$_3$) 107.8, 108.2, 127.2, 127.3, 135.4, 147.9, 153.5, 153.6, 184.8, 185.2.

MS (EI):m/z (%): 232 ([M]$^+$, 100), 217 (([M-CH$_3$]$^+$, 8).

elemental analysis calcd for C$_{13}$H$_{12}$O$_4$ (%) C, 67.23; H, 5.21. Found: C, 66.99; H, 4.90.

The spectroscopic and physical data were identical to those reported in the literature (Bringmann G. and Al, 2011, 46, 5778-5789)

4.7. 7-fluoro-2-methylnaphthalene-1,4-dione

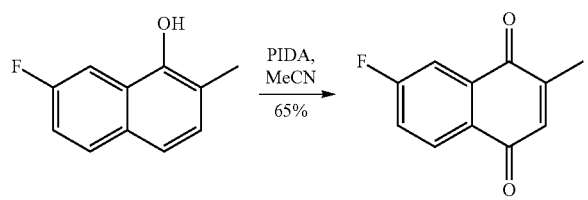

Yield: 65% yellow powder
m.p (hexane/ethyl acetate):109-110° C.
$^1$H NMR (300 MHz, CDCl$_3$): δ=8.1 (dd, J=8.3 Hz, J=5.3 Hz, 1H), 7.74 (dd, J=8.3 Hz, J=2.7 Hz, 1H), 7.21 (td, J=8.6 Hz, J=2.7 Hz, 1H), 6.8 (q, J=1.7 Hz, 1H), 3.97 (s, 3H), 2.20 (d, J=1.6 Hz, 3H) ppm.
$^{13}$C NMR (75 MHz, CDCl$_3$): δ=184.5 (C=O), 183.6 (C=O), 167.7 (C$_q$), 164.3 (C$_q$), 148.3 (d, J$_{C-F}$=2.0 Hz, CH), 135.8 (CH), 134.7 (d, J$_{C-F}$=7.7 Hz, C$_q$), 129.3 (d, J$_{C-F}$=8.9 Hz, CH), 128.9 (d, J$_{C-F}$=3.3, C$_q$), 120.8 (d, J$_{C-F}$=22.1, CH), 113.3 (d, J$_{C-F}$=22.1, CH), 16.4 (CH$_3$) ppm.
MS (EI):m/z (%): (190.0 [M]$^+$, 100), 191.0 ([M+H]$^+$, 13)
elemental analysis calcd for C$_{11}$H$_7$O$_2$F (%) C, 69.47; H, 3.71. Found C, 69.11; H, 3.49.

EXAMPLE 5

General Procedure for Alpha-Bromination of Propiophenone

It is based on the work from S. Uemura & S.-I. Fukuzawa *J. Chem. Soc., Perkin Trans. I*, 1986, 1983-1987

To a stirred solution of propiophenone in acetic acid (1 eq, 2.45 mmol·mL$^{-1}$) was added dropwise bromine/AcOH (1 eq, 20 mmol·mL$^{-1}$) keeping the temperature below 20° C. The reaction mixture was stirred at R.T. for 1-2 h, during which period the orange/red color of the mixture turned yellowish. The reaction mixture was poured in 10 volumes of water. The precipitated solids was filtered, washed with water and dried and directly used as such in the next step. (Note: sometimes the bromo compounds may not crystallize, the aqueous phase should then be extracted with an organic solvent such as dichloromethane).

5.1. 2-bromo-1-(4-fluorophenyl)propan-1-one

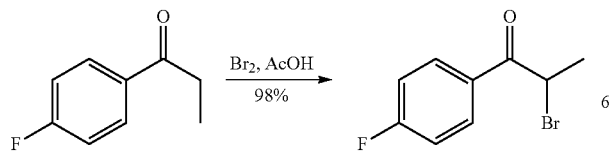

Yield: >98% (colorless oil, LACRYMATORY!!)
$^1$H NMR (200 MHz, CDCl$_3$): δ=1.90 (d, J=6.6 Hz, 3H), 5.25 (q, J=6.6 Hz, 1H), 7.16 (mc, 2H), 8.06 (dd, J=8.7 Hz, J$_{H-F}$=5.4 Hz, 2H) ppm Due to its lacrymatory nature the crude was directly engaged in the next step (6.1).

5.2. 2-bromo-1-p-tolylpropan-1-one

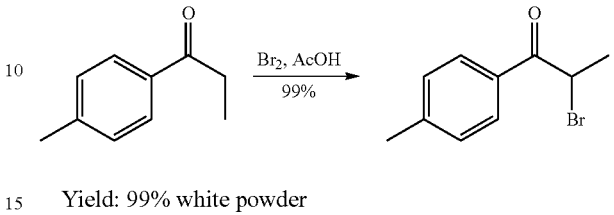

Yield: 99% white powder
$^1$H NMR (300 MHz, CDCl$_3$): δ=7.92 (d, J=8.3 Hz, 2H), 7.28 (d, J=8.3 Hz, 2H), 5.28 (q, J=6.6 Hz, 1H), 2.42 (s, 3H), 1.89 (d, J=6.6 Hz, 3H) ppm.

5.3. 2-bromo-1-(4-chlorophenyl)propan-1-one

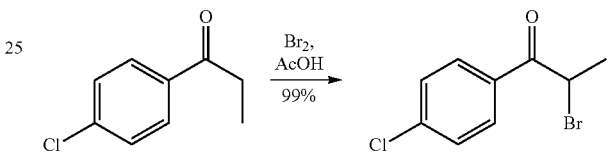

Yield: 99% white powder
$^1$H NMR (300 MHz, CDCl$_3$): δ=7.99 (d, J=8.6 Hz, 2H), 7.48 (d, J=8.6 Hz, 2H), 5.24 (q, J=6.6 Hz, 1H), 1.92 (d, J=6.6 Hz, 3H) ppm.

Due to its lacrymatory nature the crude was directly engaged in the next step (6.3).

EXAMPLE 6

General Procedure for Nucleophilic Substitution of α-Bromopropiophenone

It is based on the work from A. C. Vargas, B. Quiclet-Sire, S. Z. Zard *Org. Lett.* 2003, 5, 3717-3719

To a solution of α-bromopropiophenone in acetone (1 eq, 0.51 mmol·mL$^{-1}$) at 0° C. was added Potassium O-ethyl xanthate (1.1 eq) and the reaction mixture was stirred until disappearance of the starting material. Acetone was then evaporated and the resulting mixture was partitioned between water and dichloromethane. The organic phase was dried with brine and then MgSO$_4$. The crude was purified by flash chromatography on silica gel (cyclohexane/EtOAc).

6.1. O-ethyl S-1-(4-fluorophenyl)-1-oxopropan-2-yl carbonodithioate

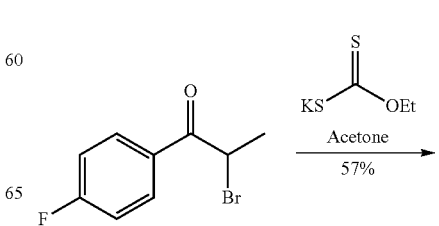

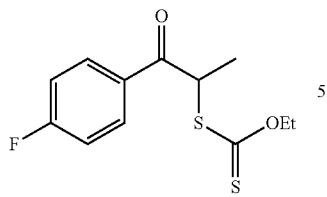

Yield: 57% (yellow oil)

This compound was mentioned twice in the literature (Liard et al. *Tetrahedron Lett.* 1997, 38, 1759-1762. Quiclet-Sire et al. *Synlett* 2003, 75-78) but without any analytical data.

$^1$H NMR (300 MHz, CDCl$_3$): δ=1.37 (t, J=7.2 Hz, 3H), 1.61 (d, J=7.1 Hz, 3H), 4.63 (q, J=7.2 Hz, 2H), 5.43 (q, J=7.1 Hz, 1H), 7.15 (mc, 2H), 8.05 (dd, J=8.7 Hz, J$_{H-F}$=5.4 Hz, 2H) ppm $^{13}$C NMR (75 MHz, CDCl$_3$): δ=13.7 (CH$_3$), 17.0 (CH$_3$), 49.9 (CH), 70.8 (CH$_2$), 115.9 (d, J$_{C-F}$=21.7 Hz, 2×CH), 131.3 (d, J$_{C-F}$"=9.1 Hz, 2×CH), 164.3 (C$_{quat}$), 167.7 (C$_{quat}$), 195.2 (C=O), 212.9 (C=S) ppm

6.2. O-ethyl S-1-oxo-1-p-tolylpropan-2-yl carbonodithioate

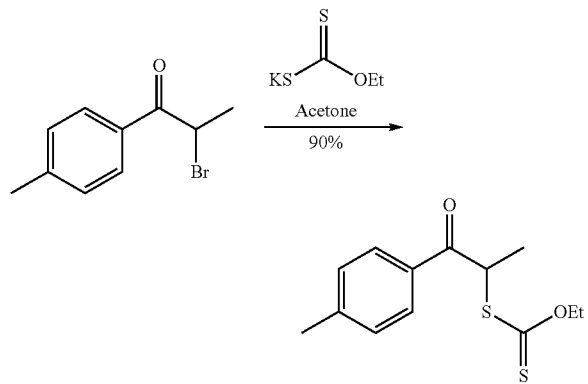

Yield: 90% brown oil $^1$H NMR (300 MHz, CDCl$_3$): δ=7.92 (d, J=7.1 Hz, 2H), 7.28 (d, J=8.2 Hz, 2H), 5.45 (q, J=7.1 Hz, 1H), 4.62 (q, J=7.2 Hz, 2H), 2.41 (s, 3H), 1.61 (d, J=7.2, 3H), 1.36 (t, J=7.1 Hz, 3H) ppm

6.3. S-1-(4-chlorophenyl)-1-oxopropan-2-yl O-ethyl carbonodithioate

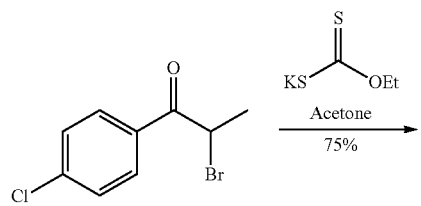

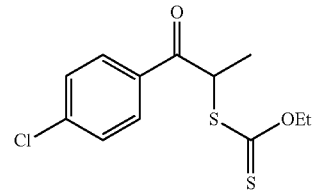

Yield: 75% brown oil $^1$H NMR (300 MHz, CDCl$_3$): δ=7.88 (d, J=8.5 Hz, 2H), 7.38 (d, J=8.25 Hz, 2H), 5.34 (q, J=7.1 Hz, 1H), 4.52 (q, J=7.2 Hz, 2H), 1.53 (d, J=7.1, 3H), 1.31 (t, J=7.2 Hz, 3H) ppm.

$^{13}$C NMR (75 MHz, CDCl$_3$): δ=13.7 (CH$_3$), 16.8 (CH$_3$), 49.9 (CH), 70.8 (CH$_2$), 129.1 (2×CH), 130.3 (2×CH), 133.4 (C$_{quat}$), 140.1 (C$_{quat}$), 195.6 (C=O), 212.8 (C=S) ppm.

EXAMPLE 7

General Procedure for Preparation of α-methyl-γ-O-pivalate-tetralones

It is based on the work from A. C. Vargas et al. cited above.

A solution of xanthate (15 mmol, 1 eq), vinyl pivalate (30 mmol, 2 eq) in 15 mL of dichloroethane was saturated with a stream of Argon for 10-15 min. The solution was refluxed under Argon. Laurolyl peroxide (DLP) was then added (5 mol %) to the refluxing solution followed by additional portions (2-3 mol %, every 1 h-1 h30). When TLC monitoring showed that starting material was consumed (after 6 to 8 additions of DLP), the solution was cooled to room temperature and filtrated through a column of basic alumina (eluant: dicholoromethane). The organic phase was evaporated. The crude was dissolved in dichloroethane (350 mL) and the solution was saturated with a stream of Argon for 10-15 nm. If the aromatic moiety bears an electrowithdrawing substituent then camphorsulfonic acid (CSA, 0.1 eq) is added. The solution was refluxed under Argon. Laurolyl peroxide (DLP) was then added to the refluxing solution followed by additional portions (20 mol %, every 1 h-1 h30). When TLC monitoring showed that starting material was consumed (after 1.2-1.4 eq of DLP), the solution was cooled to room temperature and filtrated through a column of basic alumina (eluant:dicholoromethane). The organic phase was evaporated. The crude was purified by flash chromatography (cyclohexane/EtOAc) on silica gel to obtain an oil which crystallized on standing.

7.1. cis- and trans-7-fluoro-3-methyl-4-oxo-1,2,3,4-tetrahydronaphthalen-1-yl pivalate

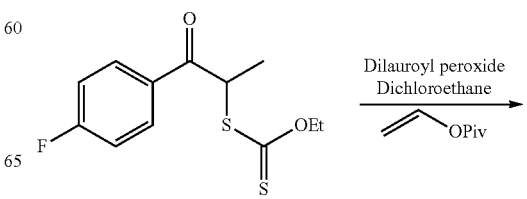

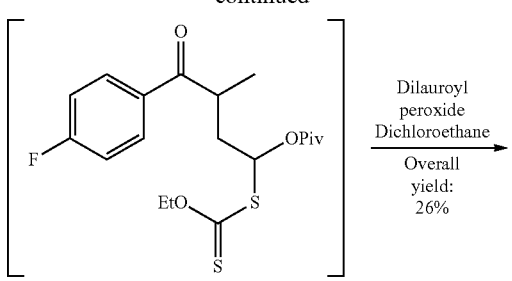
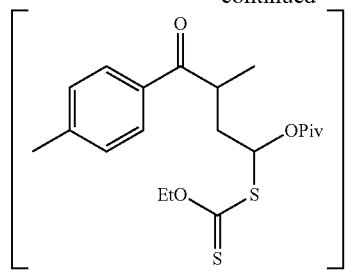

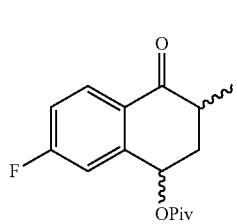

Yield: 26% (yellow oil which crystallized upon standing) after flash chromatography (silica gel, solvents:petroleumether/EtOAc 200/10). The title compounds were obtained as a mixture (1/1) of cis and trans diatereoisomers.

$^1$H NMR (300 MHz, CDCl$_3$): DIA1 δ=1.31 (s, 3H), 1.32 (s, 9H), 1.92 (mc, 1H), 2.49 (dt, J=12.5 Hz, J=4.7 Hz, 1H), 2.72 (mc, 1H), 6.15 (dd, J=11.2 Hz, J=4.7 Hz, 1H), 7.00 (ddd, J=9.5 Hz, J=2.7 Hz, J=0.9 Hz, 1H), 7.12 (m, 1H), 8.10 (dd, J=8.8 Hz, J=5.9 Hz, 1H) ppm $^1$H NMR (300 MHz, CDCl$_3$): DIA2 δ=1.19 (s, 9H), 1.28 (s, 3H), 2.17 (ddd, J=14.3 Hz, J=11.4 Hz, J=3.9 Hz, 1H), 2.35 (dt, J=14.3 Hz, J=4.6 Hz, 1H), 3.00 (mc, 1H), 6.06 (t, J=3.9 Hz, 1H), 7.11 (m, 2H), 8.10 (dd, J=8.8 Hz, J=5.9 Hz, 1H) ppm $^{13}$C NMR (75 MHz, CDCl$_3$): DIA1 δ=15.3 (CH$_3$), 27.2 (3×CH$_3$, t-Bu), 37.3 (CH$_2$), 39.0 (C$_{quat}$, t-Bu), 40.6 (CH), 68.9 (OCH), 112.3 (d, J$_{C-F}$=22.8 Hz, CH), 115.7 (d, J$_{C-F}$=21.7 Hz, CH), 128.2 (d, J$_{C-F}$=2.2 Hz, C$_{quat}$), 130.7 (d, J$_{C-F}$=9.9 Hz, CH), 145.7 (d, J$_{C-F}$=8.9 Hz, C$_{quat}$), 166.0 (d, J$_{C-F}$=256 Hz, C$_{quat}$), 177.9 (OC=O), 197.3 (C=O) ppm $^{13}$C NMR (75 MHz, CDCl$_3$): DIA2 δ=14.1 (CH$_3$), 27.0 (3×CH$_3$, t-Bu), 36.0 (CH$_2$), 37.0 (CH), 67.6 (OCH), 115.8 (d, J$_{C-F}$"=21.9 Hz, CH), 116.7 (d, J$_{C-F}$=21.9 Hz, CH), 128.5 (d, J$_{C-F}$=2.3 Hz, C$_{quat}$), 130.5 (d, J$_{C-F}$=9.6 Hz, CH), 149.9 (d, J$_{C-F}$=9.0 Hz, C$_{quat}$), 165.7 (d, J$_{C-F}$=256 Hz, C$_{quat}$), 177.7 (OC=O), 198.2 (C=O) ppm

7.2. 3,7-dimethyl-4-oxo-1,2,3,4-tetrahydronaphthalen-1-yl pivalate

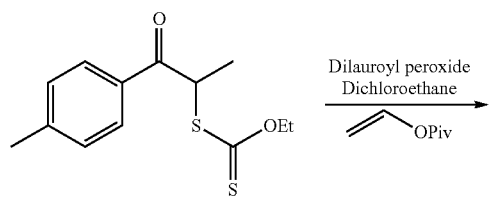

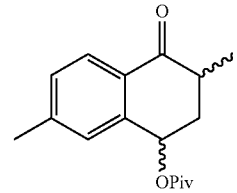

Yield: 28% brown oil $^1$H NMR (300 MHz, CDCl$_3$): DIA1 δ=1.18 (s, 3H), 1.32 (s, 9H), 1.85-1.92 (m, 1H), 2.41 (s, 3H) 2.47 (dt, J=12.4 Hz, J=4.7 Hz, 1H), 2.62-2.72 (m, 1H), 6.17 (dd, J=10.9 Hz, J=4.9 Hz, 1H), 7.11 (s, 1H), 7.23 (d, J=8.6 Hz, 1H) 8.10 (d, J=8.6 Hz, 1H)

$^1$H NMR (300 MHz, CDCl$_3$): DIA2 δ=1.19 (s, 9H), 1.28 (s, 3H), 2.17 (ddd, J=14.3 Hz, J=11.4 Hz, J=3.9 Hz, 1H), 2.35 (dt, J=14.3 Hz, J=4.6 Hz, 1H), 2.41 (s, 3H), 3.00 (mc, 1H), 6.05 (t, J=3.6 Hz, 1H), 7.11 (s, 1H), 7.23 (d, J=8.6 Hz, 1H) 8.10 (d, J=8.6 Hz, 1H), 1H).

7.3. cis- and trans-7-chloro-3-methyl-4-oxo-1,2,3,4-tetrahydronaphthalen-1-yl pivalate

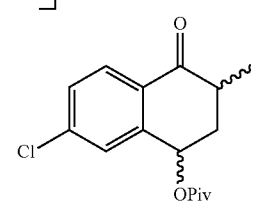

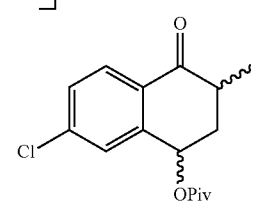

Yield: 25% brown oil $^1$H NMR (300 MHz, CDCl$_3$): DIA1 δ=1.18 (s, 3H), 1.32 (s, 9H), 1.85-1.92 (m, 1H), 2.47 (dt, J=12.4 Hz, J=4.7 Hz, 1H), 2.62-2.72 (m, 1H), 6.17 (dd, J=10.9 Hz, J=4.9 Hz, 1H), 7.11 (s, 1H), 7.23 (d, J=8.6 Hz, 1H) 8.10 (d, J=8.6 Hz, 1H), 1H) ppm.

¹H NMR (300 MHz, CDCl₃): DIA2 δ=1.19 (s, 9H), 1.28 (s, 3H), 2.17 (ddd, J=14.3 Hz, J=11.4 Hz, J=3.9 Hz, 1H), 2.35 (dt, J=14.3 Hz, J=4.6 Hz, 1H), 3.00 (mc, 1H), 6.05 (t, J=3.6 Hz, 1H), 7.11 (s, 1H), 7.23 (d, J=8.6, 1H) 8.10 (d, J=8.6, 1H), 1H) ppm.

¹³C NMR (75 MHz, CDCl₃): DIA1 δ=15.4 (CH₃), 27.2 (3×CH₃, t-Bu), 37.2 (CH₂), 39.0 ($C_{quat}$, t-Bu), 40.6 (CH), 69.2 (OCH), 113.4 (CH), 116.1 (CH), 127.4 ($C_{quat}$), 131.4 (CH), 145.2 ($C_{quat}$), 166.2 ($C_{quat}$), 178.0 (OC=O), 198.5 (C=O) ppm ¹³C NMR (75 MHz, CDCl₃): DIA2 δ=15.3 (CH₃), 27.0 (3×CH₃, t-Bu), 36.2 (CH₂), 37.5 (CH), 38.9 ($C_{quat}$, t-Bu), 68.2 (OCH), 115.8 (CH), 116.7 (d, $J_{C\text{-}F}$=21.9 Hz, CH), 128.5 ($C_{quat}$), 130.5 (CH), 149.9 ($C_{quat}$), 165.7 ($C_{quat}$), 177.9 (OC=O), 199.5 (C=O) ppm.

EXAMPLE 8

General Procedure for 2-methylnaphtol Preparation by Dehydration

It is based on the work from A. C. Vargas et al. (cited above).

A solution of tetralone (2.5 mmol, 1.0 eq) in toluene (75 mL) and p-TsOH—H₂O (7.2 mmol, 2.9 eq) was refluxed was 3-4 h with a Dean-stark apparatus. When starting material was totally consumed, the reaction mixture was allowed to cool to room temperature, neutralized with saturated Na₂CO₃, extracted with CH₂Cl₂, dried (MgSO₄) and evaporated under reduced pressure. The naphtol was directly used as such in the next step.

8.1. 6-fluoro-2-methylnaphthalen-1-ol

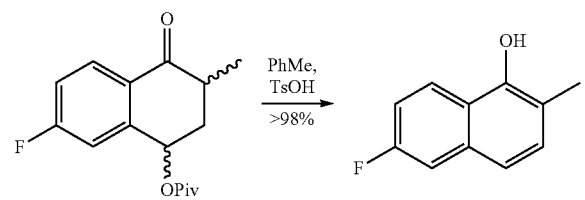

Yield: >98%

¹H NMR (300 MHz, CD₂Cl₂): δ=2.07 (s, 3H), 6.91 (td, J=2.6 Hz, J=9.0 Hz, 1H), 6.98 (AB system, J=8.6 Hz, Δν=12.3 Hz, 2H), 7.07 (dd, J=2.6 Hz, $J_{H\text{-}F}$=10.1 Hz, 1H), 7.85 (dd, 5.3 Hz, J=9.3 Hz, 1H) ppm ¹³C NMR (75 MHz, CD₂Cl₂): δ=16.0 (CH₃), 111.1 (d, $J_{C\text{-}F}$=20.0 Hz, CH), 115.9 (d, $J_{C\text{-}F}$=25.2 Hz, CH), 116.4 ($C_q$), 120.1 (d, $J_{C\text{-}F}$=5.2 Hz, CH), 122.2 ($C_q$), 124.7 (d, $J_{C\text{-}F}$=9.2 Hz, CH), 131.2 (CH), 135.0 (d, $J_{C\text{-}F}$=9.2 Hz, $C_q$), 149.7 ($C_q$), 161.3 (d, $J_{C\text{-}F}$=246.0 Hz, $C_q$) ppm MS (EI): m/z (%): 176.0 ([M]⁺, 100), 177.1 ([M+H]⁺, 13), 147.0 (36), 175.0 ([M−H]⁺, 33).

8.2. 2,6-dimethylnaphthalen-1-ol

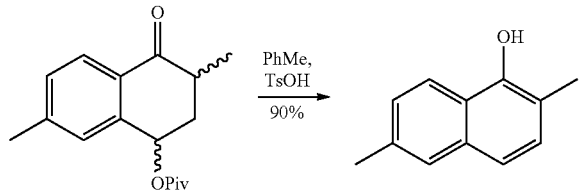

Yield: 90% Brown powder

¹H NMR (300 MHz, CDCl₃): δ=8.01 (d, J=8.6 Hz, 1H), 7.54 (s, 1H), 7.32-7.18 (m, 4H), 2.49 (s, 3H), 2.39 (s, 3H) ppm.

8.3. 7-chloro-2-dimethylnaphthalen-1-ol

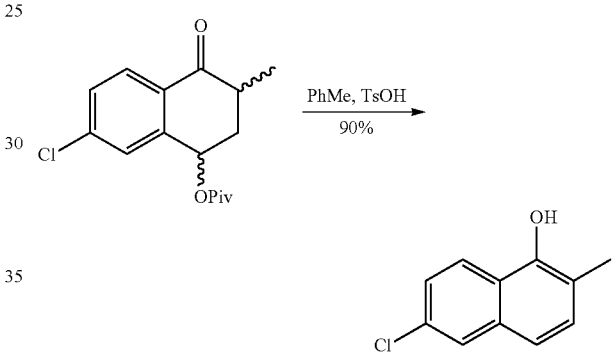

Yield: 90% Brown powder

¹H NMR (300 MHz, CDCl₃): δ=8.01 (d, J=8.6 Hz, 1H), 7.54 (s, 1H), 7.32-7.18 (m, 4H), 2.39 (s, 3H) ppm.

¹³C NMR (75 MHz, CDCl₃): δ=15.6 (CH₃), 116.4 ($C_q$) 119.2 (CH), 122.6 ($C_q$), 123.1 (CH), 126.1 (CH), 126.2 (CH), 130.3 (CH), 131.3 ($C_q$), 134.3 ($C_q$), 148.4 ($C_q$) ppm.

EXAMPLE 9

General Procedure for Preparation of Menadiones Ia1 by Diels-Alder Reaction

A solution of bromomethylquinone (1.0 eq) in dry CH₂Cl₂ (0.15 mmol/ml) was added to a suspension of ZnBr₂ (1.2 eq) in dry CH₂Cl₂ (1.5 mmol/ml). The mixture was stirred for 5 minutes and the appropriated diene was added (10 eq). After stirring overnight the reaction mixture was quenched with a solution of saturated NH₄Cl. The reaction mixture was extracted with CH₂Cl₂, and the combined CH₂Cl₂ layers were washed with brine and dried with MgSO₄. Pyridine (2 eq) was added and the mixture was stirred at rt for 4 h. CH₂Cl₂ was evaporated to yield the hydroquinone as yellow oil. The hydroquinone (1 eq) was solubilized in dioxane (0.3M) and to this solution was added 2,3-Dichloro-5,6-dicyano-1,4-benzoquinone (DDQ) (1.0 eq) at room temperature. After completion of the reaction (TLC monitoring), the white precipitate was removed by filtration. The filtrate was concentrated under reduced pressure.

The crude was purified by column chromatography (silica gel, eluant cyclohexane/EtOAc, 4:1).

9.1. 2,5-dimethylnaphthalene-1,4-dione

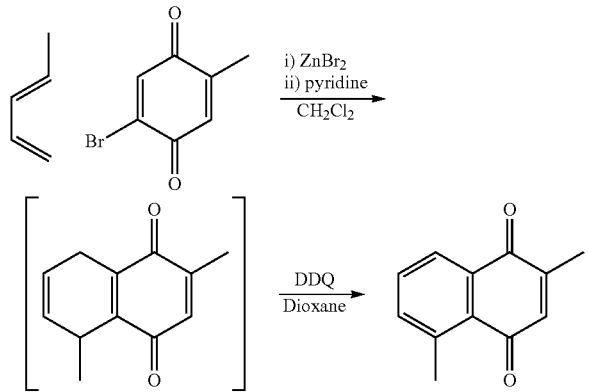

Yield: 50% (yellow needles)

Mp (from hexane/ethyl acetate): 93° C.

$^1$H NMR (300 MHz, CDCl$_3$): δ=8.04 (dd, J=7.5 Hz, 1.6 Hz, 1H), 7.61-7.50 (m, 2H), 6.78 (q, J=1.6, 1H), 2.75 (s, 3H), 2.17 (d, J=1.6, 3H) ppm.

$^{13}$C NMR (75 MHz, CDCl$_3$): δ=187.1 (C=O), 186.0 (C=O), 146.2 (C$_q$), 141.0 (C$_q$), 137.6 (CH), 137.4 (CH), 133.6 (C$_q$), 132.6 (CH), 129.7 (C$_q$), 125.4 (CH), 22.6 (CH$_3$), 15.9 (CH$_3$) ppm.

MS (EI): m/z (%): 186.0 ([M]$^+$, 100), 171 [M-CH$_3$]$^+$, 12.3)

elemental analysis calcd (%) C$_{12}$H$_{10}$O$_2$: C, 77.40; H, 5.41. Found C, 77.03; H, 5.63.

9.2. 2,6-dimethylnaphthalene-1,4-dione

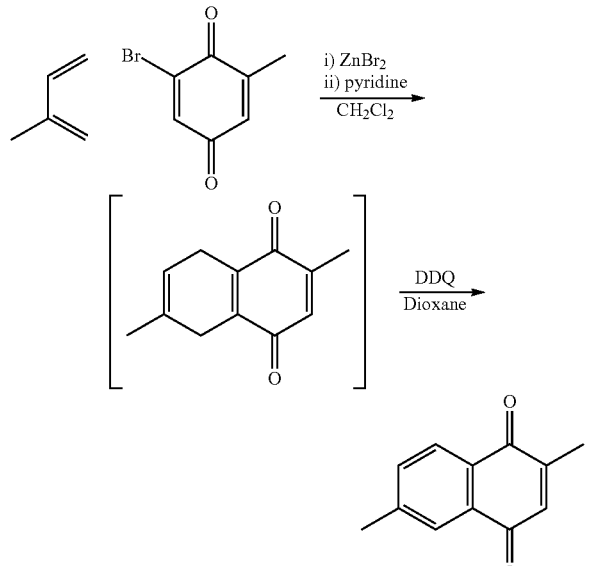

Yield: 70% yellow powder m.p (from hexane/ethyl acetate): 114-115° C. $^1$H NMR (300 MHz, CDCl$_3$): δ=7.99 (d, J=7.9 Hz, 1H), 7.85 (s, 1H), 7.52 (d, J=7.9 Hz, 1H), 6.81 (q, J=1.6 Hz, 1H), 2.49 (s, 3H), 2.19 (d, J=1.6 Hz, 3H) ppm.

$^{13}$C NMR (75 MHz, CDCl$_3$): δ=185.4 (C=O), 185.2 (C=O), 148.2 (C$_{quat}$), 144.7 (C$_{quat}$), 135.5 (CH), 135.0 (C$_{quat}$), 134.3 (CH), 132.2 (C$_{quat}$), 126.7 (CH), 126.4 (CH), 21.8 (CH$_3$), 16.5 (CH$_3$) ppm.

MS (EI): m/z (%): 186.0 ([M]$^+$, 100), 171 [M-CH$_3$]$^+$, 10)

elemental analysis calcd (%) for C$_{12}$H$_{10}$O$_2$: C, 77.40; H, 5.41. Found C, 77.12; H, 5.59.

9.3. 2,7-dimethylnaphthalene-1,4-dione

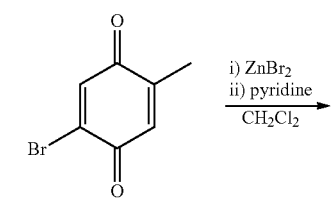

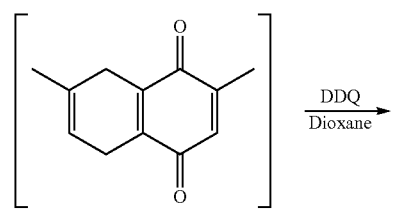

Yield: 57% Yellow needles;

m.p. (from hexane/ethyl acetate): 111-112° C.;

$^1$H NMR (300 MHz, CDCl$_3$): δ=7.95 (d, 2H, J=7.5 Hz, 1H),), 7.93 (s, 1H), 7.50 (d, J=7.5 Hz, 1H), 6.81 (q, J=1.5 Hz, 1H), 2.49 (s, 3H), 2.19 (d, J=1.6 Hz, 3H)

$^{13}$C NMR (75 MHz, CDCl$_3$): d=184.5 (C=O), 184.1 (C=O), 148.2 (C$_q$), 144.6 (C$_q$), 135.7 (CH), 134.3 (CH), 132.0 (C$_q$), 131.1 (C$_q$), 126.8 (CH), 126.2 (CH), 21.8 (CH$_3$), 16.4 (CH$_3$) ppm.

MS (EI): m/z (%): 186.0 ([M]$^+$, 100), 171 [M-CH$_3$]$^+$, 15.3)

elemental analysis calcd (%) for C$_{12}$H$_{10}$O$_2$: C, 77.40; H, 5.41. Found C, 77.77; H, 5.16.

The spectroscopic and physical data were identical to those reported in the literature: Exact Saxena and Al. J. Nat. Prod. 1996, 59, 62-65.

9.4. 2,8-dimethylnaphthalene-1,4-dione

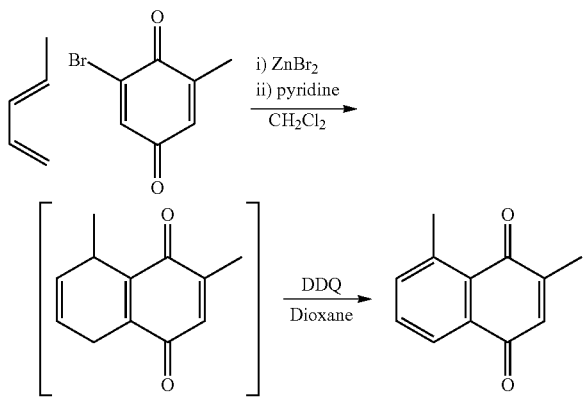

Yield: 70% (yellow needles)

m.p. (hexane/ethyl acetate): 132° C.

$^1$H NMR (300 MHz, CDCl$_3$): δ=8.00 (dd, J=7.3 Hz, 1.8 Hz, 1H), 7.62-7.49 (m, 2H), 6.81 (q, J=1.19, 1H), 2.76 (s, 3H), 2.19 (d, J=1.19, 3H)

$^{13}$C NMR (75 MHz, CDCl$_3$) 187.5 (C=O), 185.3 (C=O), 149.4 (C$_q$), 141.3 (C$_q$), 137.6 (CH), 134.3 (CH), 133.7 (C$_q$), 132.8 (CH), 129.8 (C$_q$), 125.0 (CH), 22.9 (CH$_3$), 16.8 (CH$_3$)

MS (EI): m/z (%): (186.0 [M]$^+$, 100), 171 [M-CH$_3$]$^+$, 17)

elemental analysis calcd (%) for C$_{12}$H$_{10}$O$_2$: C, 77.40; H, 5.41. Found C, 77.74; H, 5.10.

9.5. 2,6,7-trimethylnaphthalene-1,4-dione

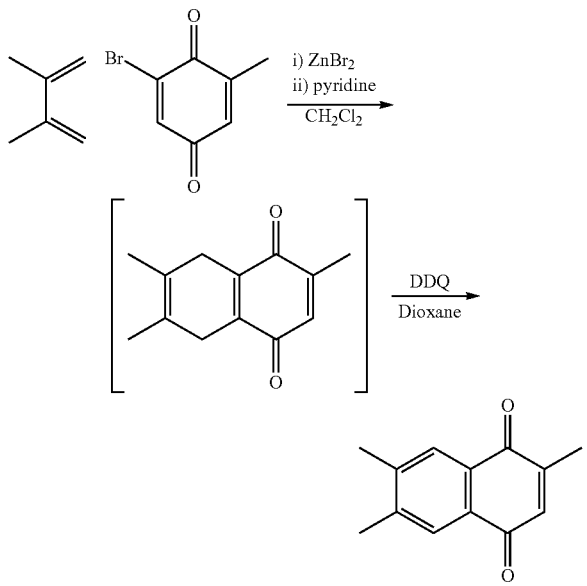

Yield: 40% (yellow needles)

Mp (from hexane/ethyl acetate): 111-112° C.

$^1$H NMR (300 MHz, CDCl$_3$): δ=7.77 (s, 1H), 7.70 (s, 1H), 6.68 (q, J=1.6 Hz, 1H), 2.31 (s, 6H), 2.09 (d, J=1.6 Hz, 3H) ppm.

$^{13}$C NMR (75 MHz, CDCl$_3$): δ=185.7 (C=O), 185.3 (C=O), 147.8 (C$_q$), 143.4 (C$_q$), 143.3 (C$_q$), 135.5 (CH), 130.3 (C$_q$), 130.2 (C$_q$), 127.5 (CH), 127.1 (CH), 20.1 (2×CH$_3$), 16.4 (CH$_3$) ppm.

MS (EI): m/z (%): (200.0 [M]$^+$, 100), 185 ([M-CH$_3$]$^+$, 19)

Elemental analysis calcd (%) for C$_{13}$H$_{12}$O$_2$: C, 77.98; H, 6.04. Found C, 77.68; H, 6.42.

EXAMPLE 10

General Procedure for Diels-Alder Reaction with Danishefsky's Diene

1-Methoxy-3-(trimethylsiloxy)-1,3-butadiene (2.0 eq) was added dropwise to a methylbromoquinone (1.0 eq) in CH$_2$Cl$_2$ (0.2M). The solution was stirred at room temperature for 2 h, then pyridine (1.5 eq) and Silica (ca. 1.5 g/mmol) were added and the suspension stirred under air at rt for 6 h. Concentration and flash column chromatography eluting with ethyl acetate/toluene (1:2) gave the hydroxy-2-methylnaphthalene-1,4-dione.

10.1 6-hydroxy-2-methylnaphthalene-1,4-dione

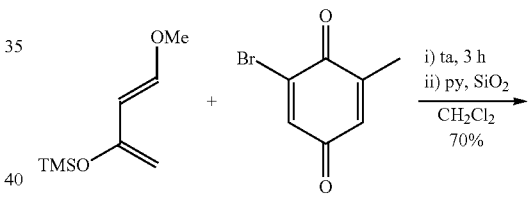

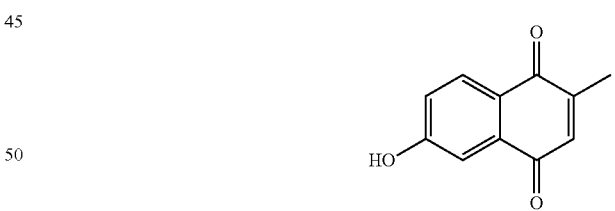

Yield: 70% (Orange solid).

m.p. 175° C. (from hexane/ethyl acetate).

$^1$H NMR (300 MHz, CD$_3$OCD$_3$): δ 7.95 (d, J=8.4 Hz, 1H), 7.39 (d, J=2.5 Hz, 1H), 7.22 (dd, J=8.4, 2.5 Hz, 1H), 6.82 (d, J=1.6 Hz, 1H), 2.13 (d, J=1.6 Hz, 3H) ppm.

$^{13}$C NMR (75 MHz, CD$_3$OCD$_3$) δ=185.5 (C=O), 184.5 (C=O), 163.4 (C$_q$), 149.4 (C$_q$), 135.9 (CH), 135.6 (C$_q$), 130.0 (CH), 125.9 (C$_q$), 121.3 (CH), 112.3 (CH), 16.4 (CH$_3$) ppm.

MS (EI) m/z (%): 188 ([M]$^+$, 100), 160 (23).

elemental analysis calcd (%) for C$_{11}$H$_8$O$_3$: C, 70.21; H, 4.29. Found C, 69.99; H, 4.32.

The spectroscopic and physical data were identical to those reported in the literature (Bringmann G. and Al, 2011, 46, 5778-5789)

10.2 7-hydroxy-2-methylnaphthalene-1,4-dione

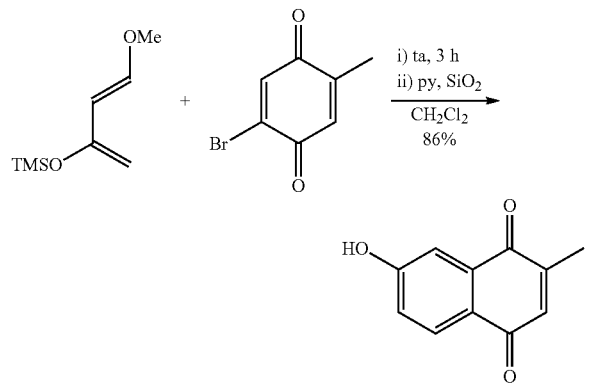

Yield: 86% (orange solid).
Mp (from hexane/ethyl acetate): 180° C. dec.
$^1$H NMR (300 MHz, CDCl$_3$): δ=10.86 (s, 1H), 7.81 (d, J=8.5 Hz, 1H), 7.29 (d, J=2.5 Hz, 1H), 7.13 (dd, J=7.9 Hz, 2.5 Hz, 1H), 6.83 (q, J=1.6 Hz, 1H), 2.06 (d, J=1.6 Hz, 3H) ppm
$^{13}$C NMR (75 MHz, CDCl$_3$): δ=185.2 (C=O), 183.4 (C=O), 162.5 (C$_q$), 147.2 (C$_q$), 135.4 (CH), 133.8 (C$_q$), 128.4 (CH), 123.9 (C$_q$), 120.5 (CH), 111.8 (CH), 15.7 (CH$_3$) ppm
MS (EI) m/z (%): 188.0 ([M]$^+$, 100), 160, (32)
elemental analysis calcd (%) for C$_{11}$H$_8$O$_3$: C, 70.21; H, 4.29. Found C, 70.03; H, 4.06.

EXAMPLE 11

General Procedure for the Synthesis of Triflates Menadiones

To a solution of hydroxymenadione (1.0 eq) in CH$_2$Cl$_2$ (0.03M) was added pyridine (2.0 eq) at room temperature under an argon atmosphere. After 10 min, Tf$_2$O (1.5 eq.) was added at 0° C. and the mixture was warmed to room temperature and stirred for 2 h. The reaction mixture was treated with a solution of 5% NaHCO$_3$ (1 ml/mmol). The mixture extracted with CH$_2$Cl$_2$. The organic phases were dried with MgSO$_4$ and concentrated in vacuo to yield menadione triflate.
Note: usually the product does not need to be further purified and can be directly engaged in the next step, the Kochi-Anderson reaction.

11.1 6-methyl-5,8-dioxo-5,8-dihydronaphthalen-2-yl trifluoromethanesulfonate

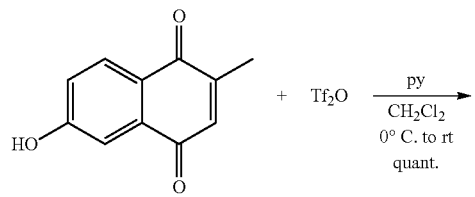

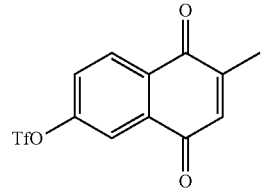

Yield: 100% (yellow solid).
Mp (petroleumether/ethyl acetate) 82° C.
$^1$H NMR (CDCl$_3$): δ=8.25 (d, J=8.4 Hz, 1H), 7.94 (d, J=2.5 Hz, 1H), 7.61 (dd, J=8.4, 2.5 Hz, 1H), 6.93 (q, J=1.6 Hz, 1H), 2.22 (d, J=1.6 Hz, 3H)
$^{13}$C NMR (CDCl$_3$) δ=184.0 (C=O), 183.0 (C=O), 153.1 (C$_q$), 149.0 (C$_q$), 136.0 (CH), 134.6 (C$_q$), 131.8 (CH), 129.7 (C$_q$), 126.5 (CH), 118.8 (q, J$_{C-F}$=320.9 Hz, CF$_3$), 117.3 (CH), 16.7 (CH$_3$) ppm
MS (EI) m/z (%): 320 (100), 188 (35).
elemental analysis calcd (%) for C$_{12}$H$_7$F$_3$O$_5$S: C, 65.90; H, 3.78. Found C, 65.58; H, 3.86.

The spectroscopic and physical data were identical to those reported in the literature (Bringmann G. and Al, 2011, 46, 5778-5789)

11.2 7-methyl-5,8-dioxo-5,8-dihydronaphthalen-2-yl trifluoromethanesulfonate

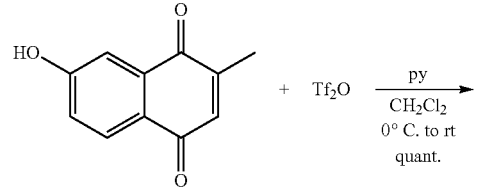

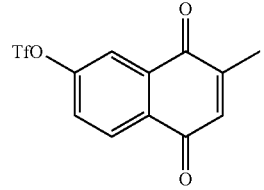

Yield: 100% (yellow solid).
Mp (from hexane/ethyl acetate): 90-91° C.
$^1$H NMR (CDCl$_3$): δ=8.20 (d, J=8.6 Hz, 1H), 7.99 (d, J=2.6 Hz, 1H), 7.63 (dd, J=8.6 Hz, 2.5 Hz, 1H), 6.91 (q, J=1.6 Hz, 1H), 2.24 (d, J=1.6 Hz, 3H) ppm.
$^{13}$C NMR (CDCl$_3$) δ d=183.6 (C=O), 183.1 (C=O), 152.8 (C$_q$), 148.7 (C$_q$), 135.8 (CH), 134.3 (C$_q$), 131.6 (CH), 129.1 (C$_q$), 126.4 (CH), 119.3 (CH), 118.7 (q, J=319.9 Hz, CF$_3$), 16.4 (CH$_3$) ppm.
MS (EI) m/z (%): 320.09 ([M]$^+$, 100), 321.09 ([M+H]$^+$, 25).
elemental analysis calcd (%) for C$_{12}$H$_7$F$_3$O$_5$S: C, 65.90; H, 3.78. Found C, 65.94; H, 3.64.

EXAMPLE 12

General Procedure for the Synthesis of Compounds Ia1

The corresponding menadione derivatives, compounds of formula (IIa1), (1 eq, 0.05 mmol·mL$^{-1}$) and a phenyl acetic acid derivative (compounds of formula (III)) (2 eq) were added to a stirred solution of MeCN/H$_2$O (3/1) and heated at 85° C. (70° C. in the flask). AgNO$_3$ (0.35 eq) was added first and then (NH$_4$)$_2$S$_2$O$_8$ (1.3 eq, 0.36 mmol·mL$^{-1}$) in MeCN/H$_2$O (3/1) was added dropwise. The reaction mixture was then heated 2-3 hours at 85° C. MeCN was evaporated and the mixture was extracted with DCM. The crude mixture was purified by flash chromatography on silica gel using a mixture diethyl ether and cyclohexane. When necessary, the compound was recristallised from hexane or a mixture of EtOAc/hexane.

12.1 3-(4-bromobenzyl)-6-methoxy-2-methylnaphthalene-1,4-dione

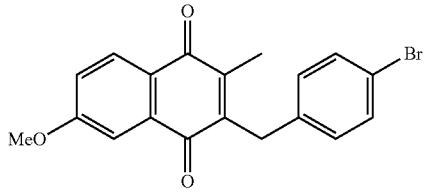 [SMILES: COc1ccc2c(c1)C(=O)C(Cc1ccc(Br)cc1)=C(C)C2=O]

Yield: 78% (yellow needles)

m.p. (from hexane/EtOAc): 135-137° C.

$^1$H NMR (300 MHz, CDCl$_3$): δ=8.04 (d, J=8.6 Hz, 1H), 7.51 (d, J=2.6 Hz, 1H), 7.25 ((AB)$_2$ system, J=8.0 Hz, Δν=40.9 Hz, 4H), 7.17 (dd, J=8.6 Hz, J=2.6 Hz, 1H), 3.96 (s, 2H), 3.93 (s, 3H), 2.23 (s, 3H) ppm $^{13}$C NMR (75 MHz, CDCl$_3$): δ=184.6 (C=O); 184.2 (C=O); 163.9 (Cq); 144.7 (Cq); 144.2 (Cq); 137.1 (Cq); 133.9 (Cq); 131.6 (2×CH); 130.2 (2×CH); 128.8 (CH); 125.6 (Cq); 120.3 (CH); 120.2 (Cq); 109.6 (CH); 55.8 (CH$_3$); 31.9 (CH$_2$); 13.3 (CH$_3$) ppm MS (EI): m/z (%): 370.0 ([M$^+$], 27), 355.0 ([M-CH$_3$]$^+$, 100)

elemental analysis calcd (%) for C$_{19}$H$_{15}$BrO$_3$: C, 61.47; H, 4.07; Br, 21.52. Found C, 61.32; H, 4.14; Br, 21.30.

12.2 6-methoxy-2-methyl-3-(4-trifluoromethyl)benzyl)naphthalene-1,4-dione

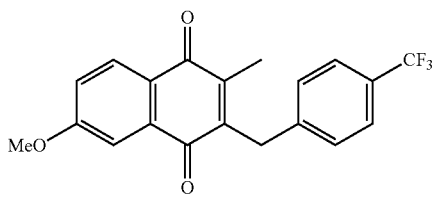 [SMILES: COc1ccc2c(c1)C(=O)C(Cc1ccc(C(F)(F)F)cc1)=C(C)C2=O]

Yield: 80% (yellow needles)

m.p. (from hexane/EtOAc): 86-87° C.

$^1$H NMR (300 MHz, CDCl$_3$): δ=8.05 (d, J=8.7 Hz, 1H), 7.51 (d, J=2.8 Hz, 1H), 7.44 ((AB)$_2$ system, J=7.8 Hz, Δν=53.6 Hz, 4H), 7.18 (dd, J=8.7 Hz, J=2.8 Hz, 1H), 4.07 (s, 2H), 3.94 (s, 3H), 2.24 (s, 3H) ppm $^{13}$C NMR (75 MHz, CDCl$_3$): δ=184.6 (C=O); 184.1 (C=O); 163.9 (Cq); 145.0 (Cq); 143.9 (Cq); 142.3 (Cq); 133.9 (Cq); 128.9 (CH); 128.8 (CH); 125.7 (Cq); 125.6 (q, J=3.7 Hz, 2×CH); 120.4 (CH); 109.7 (CH); 55.9 (CH$_3$); 32.4 (CH$_2$); 13.3 (CH$_3$) ppm MS (EI): m/z (%): 360.0 ([M$^+$], 27), 345.0 ([M-CH$_3$]$^+$, 100) elemental analysis calcd (%) for C$_{20}$H$_{15}$F$_3$O$_3$: C, 66.67; H, 4.20. Found C, 66.64; H, 4.58.

12.3. 3-(2,5-dimethoxybenzyl)-6-methoxy-2-methylnaphthalene-1,4-dione

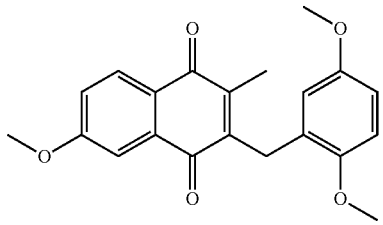

Yield: 65% (orange needles)

m.p. (hexane/EtOAc): 109-110° C.

$^1$H NMR (300 MHz, CDCl$_3$): δ=8.04 (d, J=8.0 Hz, 1H), 7.53 (d, J=2.7 Hz, 1H), 7.17 (dd, J=8.0 Hz, J=2.7 Hz, 1H), 6.81-6.63 (m, 3H), 3.99 (s, 2H), 3.94 (s, 3H), 3.82 (s, 3H), 3.71 (s, 3H), 2.23 (s, 3H) ppm.

$^{13}$C NMR (75 MHz, CDCl$_3$): δ=184.6 (C=O); 184.4 (C=O); 163.8 (Cq); 153.5 (Cq); 151.55 (Cq) 145.2 (Cq); 145.0.2 (Cq); 134.2 (Cq); 128.7 (CH); 127.7 (Cq); 125.9 (Cq); 120.1 (CH), 116.2 (CH); 110.9 (CH); 109.6 (CH); 56.0 (CH$_3$); 55.8 (CH$_3$); 55.6 (CH$_3$); 26.7 (CH$_2$); 13.3 (CH$_3$) ppm.

MS (EI): m/z (%): 352.1 ([M$^+$], 100), 337.2 ([M$^+$-CH$_3$], 93) elemental analysis calcd (%) for C$_{21}$H$_{20}$O$_5$: C, 71.58; H, 5.72. Found C, 71.23; H, 5.98.

12.4.: 3-(3,5-dimethoxybenzyl)-6-methoxy-2-methylnaphthalene-1,4-dione

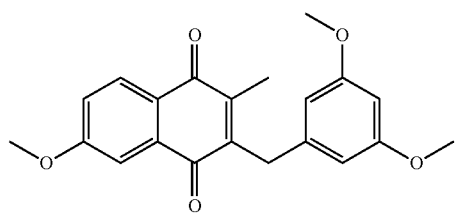

Yield: 71% (yellow needles)

m.p. (hexane/EtOAc): 149° C.

$^1$H NMR (300 MHz, CDCl$_3$): δ=8.03 (d, J=8.6 Hz, 1H), 7.52 (d, J=2.7 Hz, 1H), 7.16 (dd, J=8.6 Hz, J=2.7 Hz, 1H), 6.38 (d, J=2.3 Hz, 2H), 6.30 (t, J=2.3 Hz, 1H), 3.96 (s, 2H), 3.93 (s, 3H), 3.75 (s, 6H), 2.23 (s, 3H) ppm.

$^{13}$C NMR (75 MHz, CDCl$_3$): δ=184.6 (C=O); 184.3 (C=O); 163.8 (Cq); 160.9 (Cq); 144.8 (Cq) 144.5 (Cq); 140.2 (Cq); 134.1 (Cq); 128.8 (CH); 125.8 (Cq); 120.1 (CH), 109.7 (CH); 106.8 (2×CH); 98.0 (CH); 55.8 (CH$_3$); 55.3 (CH$_3$); 32.5 (CH$_2$); 13.3 (CH$_3$) ppm.

MS (EI): m/z (%): 352.1 ([M$^+$], 100), 337.2 ([M$^+$-CH$_3$], 93)

12.5. 3-(4-bromobenzyl)-6-fluoro-2-methylnaphthalene-1,4-dione

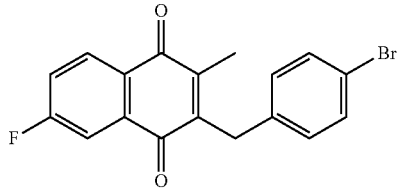 [SMILES: CC1=C(Cc2ccc(Br)cc2)C(=O)c2cc(F)ccc2C1=O]

Yield: 85% (yellow needles)

m.p. (from hexane/EtOAc) 127-129° C.

$^1$H NMR (300 MHz, CDCl$_3$): δ=8.15 (dd, J=8.6 Hz, 5.3 Hz, 1H), 7.74 (dd, J=8.6 Hz, 2.7 Hz, 1H), 7.44 ((AB)$_2$ system, J=7.6 Hz, Δν=27.6 Hz, 4H), 7.40 (m, 1H), 3.98 (s, 21H), 2.26 (s, 3H) ppm $^{13}$C NMR (75 MHz, CDCl$_3$): δ=183.9 (C=O); 183.5 (C=O); 166.0 (d, J=265.0 Hz, C$_q$); 144.9 (C$_q$); 144.8 (C$_q$); 136.8 (C$_q$); 134.5 (d, J=8.0 Hz, C$_q$); 131.8 (2×CH); 130.3 (2×CH); 129.7 (d, J=8.9 Hz, CH); 128.7 (C$_q$); 120.8 (d, J=23.0 Hz, CH); 120.4 (C$_q$); 113.2 (d, J=23.2 Hz, CH); 31.9 (CH$_2$); 13.3 (CH$_3$) ppm MS (EI): m/z (%): 358.0 ([M$^+$], 17), 343.0 ([M-CH$_3$]$^+$, 100) elemental analysis calcd (%) for C$_{18}$H$_{12}$BrFO$_2$: C, 60.19; H, 3.37; Br, 22.25. Found C, 60.08; H, 3.58; Br, 22.36.

12.6. 6-fluoro-2-methyl-3-(4-trifluoromethyl)benzyl)naphthalene-1,4-dione

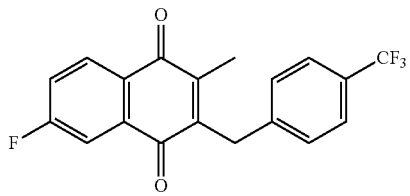 [SMILES: CC1=C(Cc2ccc(C(F)(F)F)cc2)C(=O)c2cc(F)ccc2C1=O]

Yield: 41% (yellow needles)

m.p. (from hexane) 106-107° C.

$^1$H NMR (300 MHz, CDCl$_3$): δ=8.15 (dd, J=8.6 Hz, 5.3 Hz, 1H), 7.74 (dd, J=8.6 Hz, 2.7 Hz, 1H), 7.44 ((AB)$_2$ system, J=7.8 Hz, Δν=58.8 Hz, 4H), 7.40 (dd, J=8.6 Hz, 2.7 Hz, 1H), 4.09 (s, 2H), 2.26 (s, 3H) ppm $^{13}$C NMR (75 MHz, CDCl$_3$): δ=183.8 (C=O); 183.4 (C=O); 166.0 (d, J=256.0 Hz, C$_q$); 145.1 (C$_q$); 144.5 (C$_q$); 141.9 (C$_q$); 134.4 (d, J=7.8 Hz, C$_q$); 129.7 (d, J=8.8 Hz, CH); 129.1 (C$_q$); 128.8 (2×CH); 125.9 (C$_q$); 125.6 (q, 3.3 Hz, 2×CH); 120.8 (d, J=22.7 Hz, CH); 113.2 (d, J=23.4 Hz, CH); 32.4 (CH$_2$); 13.4 (CH$_3$) ppm MS (EI): m/z (%): 349.0 [M+H$^+$], 5), 333.0 ([M-CH$_3$]$^+$, 100)

elemental analysis calcd (%) for C$_{19}$H$_{12}$F$_4$O$_2$: C, 65.52; H, 3.47. Found C, 65.39; H, 3.58.

12.7. 3-(4-bromobenzyl)-7-methoxy-2-methylnaphthalene-1,4-dione

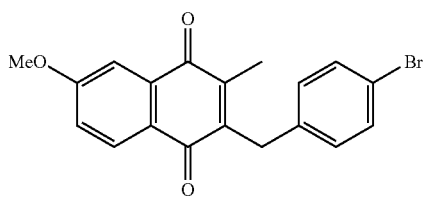 [SMILES: COc1ccc2c(c1)C(=O)C(C)=C(Cc1ccc(Br)cc1)C2=O]

Yield: 63% (yellow needles)

m.p. (from hexane/EtOAc) 149-151° C.

$^1$H NMR (300 MHz, CDCl$_3$): δ=8.05 (d, J=8.9 Hz, 1H), 7.55 (d, J=2.7 Hz, 1H), 7.40, (d, J=8.3 Hz, 2H), 7.19 (dd, J=8.7 Hz, 2.7 Hz, 1H), 7.12 (d, J=8.2 Hz, 2H), 3.98 (s, 3H), 3.96 (s, 3H), 2.23 (s, 3H) ppm $^{13}$C NMR (75 MHz, CDCl$_3$): δ=185.3 (C=O); 183.6 (C=O); 163.9 (C$_q$); 144.8 (C$_q$); 144.0 (C$_q$); 137.2 (C$_q$); 134.1 (d, J=8.0 Hz, C$_q$); 131.7 (2×CH); 130.3 (2×CH); 129.0 (CH); 125.5 (C$_q$); 120.2 (d, J=31.1 Hz, CH); 120.2 (C$_q$); 109.3 (d, J=Hz, CH), 56.1 (CH$_3$); 31.9 (CH$_2$); 13.3 (CH$_3$) ppm MS (EI): m/z (%): 357.1 ([M$^+$-CH$_3$], 65), 372.1 ([M$^+$], 23), 355 (100), 276.1 ([M$^+$-CH$_3$—Br], 46)

elemental analysis calcd (%) for elemental analysis calcd (%) for C$_{19}$H$_{15}$BrO$_3$: C, 61.47; H, 4.07; Br, 21.52. Found C, 61.18; H, 4.13.

12.8. 7-methoxy-2-methyl-3-(4-trifluoromethyl)benzyl)naphthalene-1,4-dione

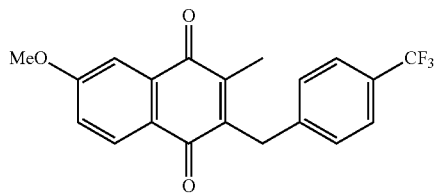 [SMILES: COc1ccc2c(c1)C(=O)C(C)=C(Cc1ccc(C(F)(F)F)cc1)C2=O]

Yield: 70% (yellow needles)

m.p. (from hexane/EtOAc) 137-139° C.

$^1$H NMR (300 MHz, CDCl$_3$): δ=8.03 (d, J=8.6 Hz, 1H), 7.53 (d, J=2.5 Hz, 2H), 7.51, (s, 1H), 7.34 (d, J=8.6 Hz, 2H), 7.18 (dd, J=8.6 Hz, 2.5 Hz, 1H), 3.98 (s, 3H), 3.96 (s, 3H), 2.23 (s, 3H) ppm $^{13}$C NMR (75 MHz, CDCl$_3$): δ=185.2 (C=O), 183.5 (C=O), 164.0 (C$_q$), 144.5 (C$_q$), 144.3 (C$_q$), 142.3 (C$_q$), 134.0 (C$_q$) 128.7 (q, J=31 Hz, C$_q$), 125.4 (C$_q$), 124.1 (q, J=270 Hz, CF$_3$), 123.5 (q, J=3.4 Hz 2×CH), 122.3 (C$_q$), 120.2 (CH), 109.6 (CH), 55.9 (CH$_3$), 32.3 (CH$_2$), 13.3 (CH$_3$) ppm MS (EI): m/z (%): 360.1 ([M⁺], 39), 345.0 ([M⁺-CH₃], 100), 343.1 (50) elemental analysis calcd (%) for $C_{20}H_{15}F_3O_3$: C, 66.67; H, 4.2. Found C, 66.64; H, 4.58.

12.9. 3-(3,5-dimethoxybenzyl)-7-methoxy-2-methyl-naphthalene-1,4-dione

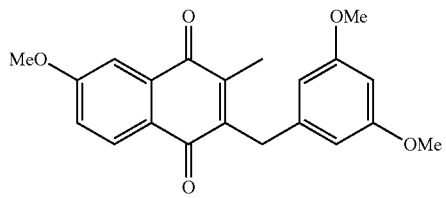 [SMILES: COc1cc(CC2=C(C)C(=O)c3cc(OC)ccc3C2=O)cc(OC)c1]

Yield: 77% (orange needles)

m.p. (from hexane/EtOAc): 151-153° C.

¹H NMR (300 MHz, CDCl₃): δ=7.95 (d, J=8.6 Hz, 1H), 7.44 (d, J=2.7 Hz, 1H), 7.08 (dd, J=8.6 Hz, J=2.7 Hz, 1H), 6.30 (d, J=2.2 Hz, 2H), 6.22 (t, J=2.2 Hz, 1H), 3.88 (s, 2H), 3.86 (s, 3H), 3.67 (s, 6H), 2.14 (s, 3H) ppm.

¹³C NMR (75 MHz, CDCl₃): δ=185.4 (C=O); 183.7 (C=O); 163.8 ($C_q$); 160.9 ($C_q$); 144.8 ($C_q$) 144.5 ($C_q$); 140.2 ($C_q$); 134.1 ($C_q$); 128.8 (CH); 125.8 ($C_q$); 120.1 (CH), 109.7 (CH); 106.8 (2×CH); 98.0 (CH); 55.8 (—OCH₃); 55.3 (—OCH₃×2); 32.5 (CH₂); 13.3 (CH₃) ppm.

MS (EI): m/z (%): 352.1 ([M⁺], 86), 337.2 ([M⁺-CH₃], 100)

elemental analysis calcd (%) for $C_{21}H_{20}O_5$: C, 71.58; H, 5.72. Found C, 71.41; H, 5.82.

12.10. 3-(2,5-dimethoxybenzyl)-6-methoxy-2-methylnaphthalene-1,4-dione

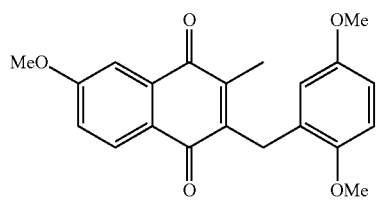 [SMILES: COc1ccc(OC)c(CC2=C(C)C(=O)c3cc(OC)ccc3C2=O)c1]

Yield: 65% (orange needles)

m.p. (from hexane/EtOAc): 180° C. dec.

¹H NMR (300 MHz, CDCl₃): δ=8.05 (d, J=8.6 Hz, 1H), 7.55 (d, J=2.7 Hz, 1H), 7.18 (dd, J=8.6 Hz, J=2.7 Hz, 1H), 6.81-6.62 (m, 3H), 4.00 (s, 2H), 3.96 (s, 3H), 3.82 (s, 3H), 3.71 (s, 3H), 2.16 (s, 3H) ppm.

¹³C NMR (75 MHz, CDCl₃): δ=185.5 (C=O); 183.7 (C=O); 163.7 ($C_q$); 153.5 ($C_q$); 151.55 ($C_q$) 145.5 ($C_q$); 144.0 ($C_q$); 134.2 ($C_q$); 128.9 (CH); 127.8 ($C_q$); 125.8 ($C_q$); 120.0 (CH), 116.2 (CH); 110.9 (CH); 109.4 (CH); 56.0 (CH₃); 55.9 (CH₃); 55.6 (CH₃); 26.6 (CH₂); 13.0 (CH₃) ppm.

MS (EI): m/z (%): 352.1 ([M⁺], 44), 337.2 ([M⁺-CH₃], 53)

elemental analysis calcd (%) for $C_{21}H_{20}O_5$: C, 71.58; H, 5.72. Found C, 71.47; H, 5.76.

12.11. 6,7-dimethoxy-2-methyl-3-(4-(trifluoromethyl)benzyl)naphthalene-1,4-dione

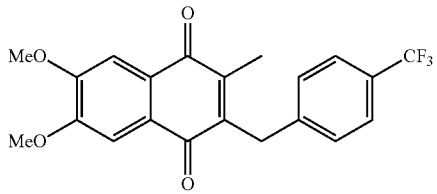 [SMILES: COc1cc2c(cc1OC)C(=O)C(Cc1ccc(C(F)(F)F)cc1)=C(C)C2=O]

Yield: 80% (orange powder)

m.p. (from hexane/EtOAc): >200° C. dec

¹H NMR (300 MHz, CDCl₃): δ=7.50 (s, 1H), 7.49 (s, 1H), 7.44 ((AB)₂ system, J=7.9 Hz, Δν=52.2 Hz, 4H), 4.05 (s, 2H), 4.01 (s, 3H), 4.00 (s, 3H), 2.22 (s, 3H) ppm.

¹³C NMR (75 MHz, CDCl₃): δ=184.5 (C=O); 184.0 (C=O); 153.4 ($C_q$); 153.3 ($C_q$); 144.2 ($C_q$); 143.8 ($C_q$); 142.5 ($C_q$); 128.9 (2×CH); 128.8 (q, J=32.8 Hz, $C_q$); 126.8 ($C_q$); 126.6 ($C_q$); 125.5 (q, J=3.8 Hz, 2×CH); 124.1 (q, J=278.3 Hz, CF₃); 107.9 (CH); 107.8 (CH); 56.5 (OMe); 56.4 (OMe); 32.3 (CH₂); 13.2 (CH₃) ppm.

MS (EI): m/z (%) 390.0 ([M⁺], 38), 375.10 ([M-CH₃]⁺, 100)

elemental analysis calcd (%) $C_{21}H_{17}F_3O_4$: C, 64.61; H, 4.39. Found C, 64.44; H, 4.49.

12.12. 6,7-dimethoxy-2-methyl-3-(4-bromobenzyl)naphthalene-1,4-dione

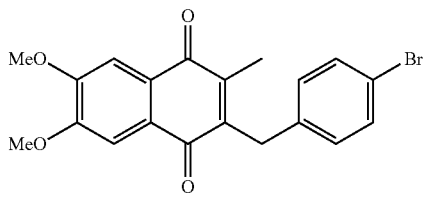 [SMILES: COc1cc2c(cc1OC)C(=O)C(Cc1ccc(Br)cc1)=C(C)C2=O]

Yield: 75% (orange powder)

m.p. (from hexane/EtOAc): >200° C. dec ¹H NMR (300 MHz, CDCl₃): δ=7.51 (s, 1H), 7.50 (s, 1H), 7.25 ((AB)₂ system, J=8.6 Hz, Δν=81.2 Hz, 4H), 4.01 (s, 3H), 4.00 (s, 3H), 3.95 (s, 2H), 2.21 (s, 3H) ppm.

¹³C NMR (75 MHz, CDCl₃): δ=184.7 (C=O); 184.1 (C=O); 153.3 ($C_q$); 153.2 ($C_q$); 144.1 ($C_q$); 143.9 ($C_q$); 137.3 ($C_q$); 131.7 (2×CH); 130.3 (2×CH); 126.8 ($C_q$); 126.7 ($C_q$), 120.2 ($C_q$); 107.9 (CH); 107.8 (CH); 56.5 (OCH₃), 56.4 (OCH₃), 31.9 (CH₂); 13.2 (CH₃) ppm.

MS (EI): m/z (%): (400.0 [M]⁺, 28), 385.0 ([M-CH₃]⁺, 100)

elemental analysis calcd (%) for C₂₀H₁₇BrO₄: C, 59.87; H, 4.27. Found C, 59.62; H, 4.49.

12.13. 2-(3,5-dimethoxybenzyl)-6,7-dimethoxy-3-methylnaphthalene-1,4-dione

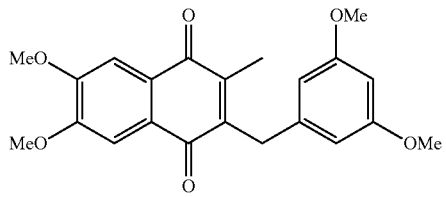 [SMILES: COc1cc(CC2=C(C)C(=O)c3cc(OC)c(OC)cc3C2=O)cc(OC)c1]

Yield: 55% (orange powder)

m.p. (from hexane/EtOAc): 168-169° C.

¹H NMR (300 MHz, CDCl₃): 7.50 (s, 2H), 6.38 (d, J=2.3 Hz, 2H), 6.30 (t, J=2.3 Hz, 1H), 4.01 (s, 3H), 4.00 (s, 3H), 3.94 (s, 2H), 3.75 (s, 6H), 2.21 (s, 3H) ppm.

¹³C NMR (75 MHz, CDCl₃): δ=184.8 (C=O); 184.1 (C=O); 160.9 ($C_q$); 153.2 ($C_q$); 144.3 ($C_q$) 144.0 ($C_q$); 140.5 ($C_q$); 126.9 ($C_q$); 126.8 ($C_q$); 108.0 (CH); 107.5 (CH), 106.8 (2×CH); 94.4 (CH); 56.5 (CH₃); 56.4 (CH₃); 55.3 (2×CH₃); 32.5 (CH₂); 13.2 (CH₃) ppm.

MS (EI): m/z (%): (400.0 [M]⁺, 42), 385.0 ([M-CH₃]⁺, 100)

elemental analysis calcd (%) for C₂₂H₂₂O₆: C, 69.10; H, 5.80. Found C, 68.84; H, 5.74.

12.14. 2-14(2,5-dimethoxybenzyl)-6,7-dimethoxy-3-methylnaphthalene-1,4-dione

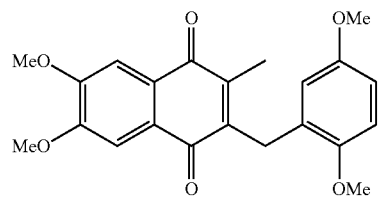 [SMILES: COc1ccc(OC)c(CC2=C(C)C(=O)c3cc(OC)c(OC)cc3C2=O)c1]

Yield: 72% (orange powder)

m.p. (from hexane/EtOAc): 166-167° C.

¹H NMR (300 MHz, CDCl₃): δ=7.52 (s, 1H), 7.51 (s, 1H), 6.80-6.62 (m, 3H), 4.02 (s, 3H), 4.00 (s, 3H), 3.96 (s, 2H), 3.81 (s, 3H), 3.70 (s, 3H), 2.14 (s, 3H) ppm.

¹³C NMR (75 MHz, CDCl₃): δ=184.9 (C=O); 184.0 (C=O); 153.5 ($C_q$); 153.2 ($C_q$); 153.1 ($C_q$); 151.5 ($C_q$) 144.7 ($C_q$); 144.4 ($C_q$); 127.9 ($C_q$); 127.0 ($C_q$); 126.9 ($C_q$); 116.2 (CH), 111.2 (CH); 110.8 (CH); 108.0 (CH); 107.7 (CH); 56.5 (CH₃); 56.4 (CH₃); 56.0 (CH₃); 55.6 (CH₃); 26.6 (CH₂); 12.9 (CH₃) ppm.

MS (EI): m/z (%): (400.0 [M]⁺, 78), 385.0 ([M-CH₃]⁺, 100)

elemental analysis calcd (%) for C₂₂H₂₂O₆: C, 69.10; H, 5.80. Found C, 69.20; H, 5.81.

12.15. 6-fluoro-3-methyl-2-(4-(trifluoromethyl)benzyl)naphthalene-1,4-dione

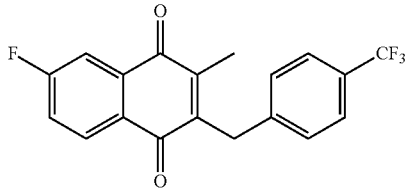 [SMILES: CC1=C(Cc2ccc(C(F)(F)F)cc2)C(=O)c2ccc(F)cc2C1=O]

Yield: 65% (yellow needles)

m.p. (from hexane/EtOAc): 104-105° C.

¹H NMR (300 MHz, CDCl₃): δ=8.15 (dd, J=8.6 Hz, 5.3 Hz, 1H), 7.76 (dd, J=8.6 Hz, 2.8 Hz, 1H), 7.44 ((AB)₂ system, J=7.6 Hz, Δν=27.6 Hz, 4H), 7.40-7.34 (m, 1H), 4.10 (s, 2H), 2.27 (s, 3H) ppm.

¹³C NMR (75 MHz, CDCl₃): δ=184.0 (C=O); 183.2 (C=O); 166.0 (d, J=244.0 Hz, $C_q$); 145.0 ($C_q$); 144.6 ($C_q$); 142.0 ($C_q$); 134.6 (d, J=7.4 Hz, $C_q$); 129.8 (d, J=9.0 Hz, CH); 128.9 (q, J=24.1 Hz $C_q$); 128.8 (2×CH); 128.4 ($C_q$); 125.6 (q, J=4.0 Hz, 2×CH); 120.8 (d, J=21.9 Hz, CH); 113.1 (d, J=24.1 Hz, CH); 32.3 (CH₂); 13.6 (CH₃) ppm.

MS (EI): m/z (%): 349.0 [M+H⁺], 5), 333.0 [M-CH₃]⁺, 100)

elemental analysis calcd (%) for C₁₉H₁₂F₄O₂: C, 65.52; H, 3.47. Found C, 65.38; H, 3.68.

12.16. 2-(4-bromobenzyl)-6-fluoro-3-methylnaphthalene-1,4-dione

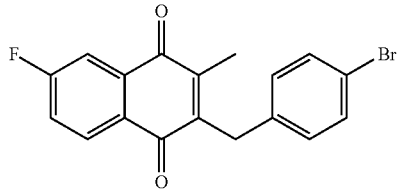 [SMILES: CC1=C(Cc2ccc(Br)cc2)C(=O)c2ccc(F)cc2C1=O]

Yield: 85% (yellow needles)

m.p. (from hexane/EtOAc): 107° C.

¹H NMR (300 MHz, CDCl₃): δ=8.14 (dd, J=8.6 Hz, 5.2 Hz, 1H), 7.75 (dd, J=8.6 Hz, 2.7 Hz, 1H), 7.35 (m, 1H), 7.26 ((AB)₂ system, J=7.6 Hz, Δν=27.6 Hz, 4H), 3.99 (s, 2H), 2.26 (s, 3H) ppm.

¹³C NMR (75 MHz, CDCl₃): δ=184.1 (C=O); 183.2 (C=O); 166.0 (d, J=254.0 Hz, $C_q$); 145.0 ($C_q$); 144.7 ($C_q$); 136.8 ($C_q$); 134.7 (d, J=8.4 Hz, $C_q$); 131.8 (2×CH); 130.3 (2×CH); 129.8 (d, J=8.9 Hz, CH); 128.5 ($C_q$); 120.8 (d, J=24.0 Hz, CH); 120.4 ($C_q$); 113.0 (d, J=24.0 Hz, CH); 31.9 (CH₂); 13.3 (CH₃) ppm.

MS (EI): m/z (%): 358.0 ([M⁺], 17), 343.0 ([M-CH₃]⁺, 100) elemental analysis calcd (%) for $C_{18}H_{12}BrFO_2$: C, 60.19; H, 3.37. Found C, 59.95; H, 3.67.

12.17. 2-(3-chloro-4-fluorobenzyl)-6-fluoro-3-methylnaphthalene-1,4-dione

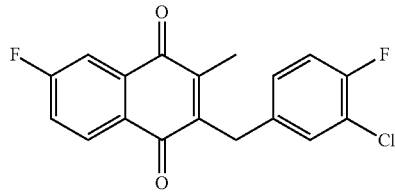 [SMILES: CC1=C(Cc2ccc(F)c(Cl)c2)C(=O)c2ccc(F)cc2C1=O]

Yield: 45% yellow powder
m.p. (from hexane/EtOAc): 117-118° C.
¹H NMR (300 MHz, CDCl₃): δ=8.13 (dd, J=8.6 Hz, 5.3 Hz, 1H), 7.74 (dd, J=8.6 Hz, 2.7 Hz, 1H), 7.38 (td, J=8.3, 2.7 Hz, 1H), 7.10-7.01 (m, 3H), 3.97 (s, 2H), 2.26 (s, 3H) ppm.
¹³C NMR (75 MHz, CDCl₃): δ=184.0 (d, $J_{C-F}$=1.0 Hz, C=O), 183.2 (C=O), 166.1 (d, $J_{C-F}$=256.8 Hz, $C_q$), 156.9 (d, $J_{C-F}$=249.0 Hz, $C_q$), 144.8 (d, $J_{C-F}$=1.7 Hz, $C_q$), 144.6 ($C_q$), 134.8 (d, $J_{C-F}$=3.3 Hz, $C_q$), 134.6 (d, $J_{C-F}$=7.5 Hz, $C_q$), 130.5 (CH), 129.8 (d, $J_{C-F}$=9.4 Hz, CH), 128.5 (d, $J_{C-F}$=2.8 Hz, $C_q$), 128.3 (d, $J_{C-F}$=6.6 Hz, CH), 121.1 (d, $J_{C-F}$=18.0 Hz, $C_q$), 120.9 (d, $J_{C-F}$=22.4 Hz, CH), 116.7 (d, $J_{C-F}$=21.6 Hz, CH), 113.1 (d, $J_{C-F}$=23.4 Hz, CH), 31.5 (CH₂), 13.4 (CH₃) ppm.
MS (EI): m/z (%): 332.0 ([M⁺], 14), 317.0 ([M-CH₃]⁺, 100)
elemental analysis calcd (%) for $C_{18}H_{11}ClF_2O_2$: C, 64.98; H, 3.33. Found C, 65.30; H, 3.68.

12.18. 6-fluoro-2-(4-fluoro-3-(trifluoromethyl)benzyl)-3-methylnaphthalene-1,4-dione

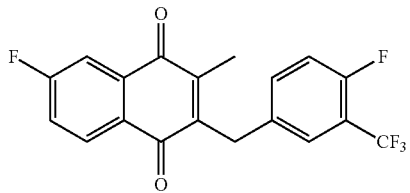 [SMILES: CC1=C(Cc2ccc(F)c(C(F)(F)F)c2)C(=O)c2ccc(F)cc2C1=O]

Yield: 55% yellow powder
m.p. (from hexane/EtOAc): 106-107° C.
¹H NMR (300 MHz, CDCl₃): δ=8.13 (dd, J=8.6, 5.3 Hz, 1H), 7.74 (dd, J=8.6, 2.7 Hz, 1H), 7.38 (dd, J=6.6, 2.7 Hz, 1H), 7.43-7.35 (m, 2H), 7.11 (t, J=9.2 Hz, 1H), 4.04 (s, 2H), 2.27 (s, 3H) ppm.
¹³C NMR (75 MHz, CDCl₃): δ=184.0 (d, $J_{C-F}$=1.3 Hz, C=O), 183.2 (C=O), 166.1 (d, $J_{C-F}$=256.0 Hz, $C_q$), 158.5 (dq, $J_{C-F}$=254.8, 1.6 Hz, $C_q$), 144.9 (d, $J_{C-F}$=1.7 Hz, $C_q$), 144.4 ($C_q$), 134.6 (d, $J_{C-F}$=8.0 Hz, $C_q$), 134.1 (d, $J_{C-F}$=d, $J_{C-F}$=3.6 Hz, $C_q$), 133.9 (d, $J_{C-F}$=7.8 Hz, CH), 129.9 (d, $J_{C-F}$=8.9 Hz, CH), 128.4 (d, $J_{C-F}$=3.3 Hz, $C_q$), 127.1 (dq, $J_{C-F}$=4.5, 1.6 Hz, CH), 124.2 (d, $J_{C-F}$=1.0 Hz, $C_q$), 120.9 (d, $J_{C-F}$=22.6 Hz, CH), 117.1 (d, $J_{C-F}$=20.7, CH), 113.1 (d, $J_{C-F}$=22.8, CH), 31.6 (CH₂), 13.4 (CH₃) ppm.
MS (EI): m/z (%): 366.0 ([M⁺], 26), 351.0 ([M-CH₃]⁺, 100)

elemental analysis calcd (%) for $C_{19}H_{11}F_5O_2$: C, 62.30; H, 3.03. Found C, 62.31; H, 3.28.

12.19. 2,5-dimethyl-3-(4-(trifluoromethyl)benzyl)naphthalene-1,4-dione

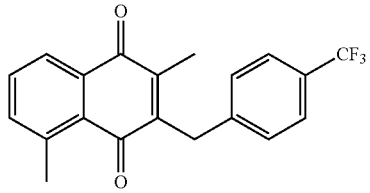 [SMILES: CC1=C(Cc2ccc(C(F)(F)F)cc2)C(=O)c2c(C)cccc2C1=O]

Yield: 63% (yellow needles)
m.p. (from hexane/EtOAc): 87-88° C.
¹H NMR (300 MHz, CDCl₃): δ=8.04 (dd, J=7.6 Hz, 1.2 Hz, 1H), 7.60-7.50 (m, 2H), 7.46 ((AB)₂ system, J=7.5 Hz, Δν=55.2 Hz, 4H), 4.09 (s, 2H), 2.74 (s, 3H), 2.23 (s, 3H) ppm.
¹³C NMR (75 MHz, CDCl₃): δ=186.3 (C=O); 185.5 (C=O); 145.6 ($C_q$); 143.2 ($C_q$); 142.4 ($C_q$); 141.2 ($C_q$); 137.6 (CH); 133.5 ($C_q$); 132.7 (CH); 129.7 ($C_q$); 128.8 (2×CH); 128.7 (q, J=31 Hz, $C_q$), 125.5 (q, J=3.8 Hz, 2×CH); 124.2 (q, J=273.0 Hz, CF₃); 125.3 (CH); 32.5 (CH₂); 22.9 (CH₃); 13.1 (CH₃) ppm.
MS (EI): m/z (%): 344.2 ([M⁺], 33), 329.2 ([M⁺-CH₃], 100)
elemental analysis calcd (%) for $C_{20}H_{15}F_3O_2$: C, 69.76; H, 4.39. Found C, 69.49; H, 4.54.

12.20. 3-(4-bromobenzyl)-2,5-dimethylnaphthalene-1,4-dione

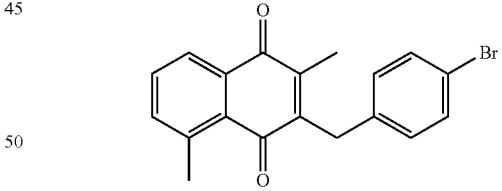

Yield: 75% (yellow needles)
m.p. (from hexane/EtOAc): 149-150° C.
¹H NMR (300 MHz, CDCl₃): δ=8.03 (dd, J=7.5 Hz, 1.5 Hz 1H), 7.59-7.49 (m, 2H), 7.27 ((AB)₂ system, J=7.4 Hz, Δν=81.3 Hz, 4H), 3.96 (s, 2H), 2.76 (s, 3H), 2.29 (s, 3H)
¹³C NMR (75 MHz, CDCl₃): δ=186.4 (C=O); 185.6 (C=O); 146.0 ($C_q$); 142.9 ($C_q$); 141.1 ($C_q$); 137.6 (CH); 137.3 ($C_q$); 133.2 ($C_q$); 132.6 (CH); 131.7 (2×CH); 130.2 (2×CH); 129.7 ($C_q$); 125.2 (CH); 120.2 ($C_q$); 32.1 (CH₂); 22.9 (CH₃); 13.1 (CH₃) ppm.
MS (EI): m/z (%) 355.03 ([M⁺], 100), 356.04 ([M+H⁺], 18),

12.21. 3-(4-bromobenzyl)-2,6-dimethylnaphthalene-1,4-dione

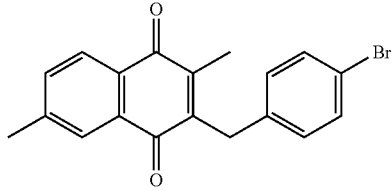 [SMILES: CC1=C(Cc2ccc(Br)cc2)C(=O)c2cc(C)ccc2C1=O]

Yield: 50% (yellow needles)

$^1$H NMR (300 MHz, CDCl$_3$): δ=7.98 (d, J=7.9 Hz, 1H), 7.87 (s, 1H), 7.50 (d, J=7.9 Hz, 1H) 7.38, (d, J=8.4 Hz, 2H), 7.11 (d, J=7.4, 2H), 3.96 (s, 2H),), 2.48 (s, 3H) 2.23 (s, 3H) ppm $^{13}$C NMR (75 MHz, CDCl$_3$): δ=185.1 (C=O); 184.9 (C=O); 144.7 (C$_{quat}$); 144.5 (C$_{quat}$); 137.2 (C$_{quat}$); 134.3 (CH); 131.8 (C$_{quat}$); 131.7 (2×CH); 130.3 (2×CH); 129.9 (C$_{quat}$) 126.8 (CH); 126.5 (CH); 120.3 (C$_{quat}$); 31.9 (CH$_2$); 21.9 (CH$_3$) 13.3 (CH$_3$) ppm MS (EI): m/z (%): 354.1 ([M$^+$], 18), 341 (78), 339.1 ([M$^+$-CH$_3$], 100), 260.1 (43), elemental analysis calcd (%) for C$_{19}$H$_{15}$BrO$_2$: C, 64.24; H, 4.26. Found C, 64.15; H, 4.27.

m.p. 103-104° C.

12.22. 2,6-dimethyl-3-(4-(trifluoromethyl)benzyl)naphthalene-1,4-dione

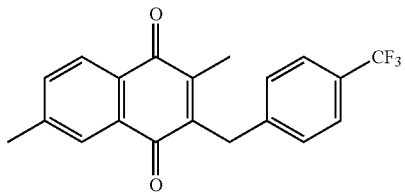 [SMILES: CC1=C(Cc2ccc(C(F)(F)F)cc2)C(=O)c2cc(C)ccc2C1=O]

Yield: 65% (yellow needles)

$^1$H NMR (300 MHz, CDCl$_3$): δ=7.98 (d, J=7.4 Hz, 1H), 7.87 (s, 1H), 7.53-7.48 (m, 3H), 7.17 (d, J=7.4, 2H), 4.07 (s, 2H),), 2.48 (s, 3H) 2.23 (s, 3H) ppm $^{13}$C NMR (75 MHz, CDCl$_3$): δ=185.0 (C=O); 184.8 (C=O); 144.8 (C$_{quat}$); 144.7 (C$_{quat}$); 144.2 (C$_{quat}$); 144.4 (C$_{quat}$); 134.4 (CH); 131.8 (C$_{quat}$); 128.9 (2×CH); 126.9 (CH); 129.9 (C$_{quat}$) 126.6 (CH); 125.6 (q, J=3.8 Hz 2×CH); 122.3 (C$_{quat}$); 32.3 (CH$_2$); 21.8 (CH$_3$) 13.3 (CH$_3$) ppm MS (EI): m/z (%): 344.2 ([M$^+$], 30), 329.2 ([M$^+$-CH$_3$], 100), 372. 2 (19)

elemental analysis calcd (%) for C$_{20}$H$_{15}$F$_3$O$_2$: C, 69.76; H, 4.39. Found C, 69.57; H, 4.44.

m.p. 93-94° C.

elemental analysis calcd (%) for C$_{19}$H$_{15}$BrO$_3$: C, 64.24; H, 4.26. Found C, 64.01; H, 4.33.

12.23. 2,7-dimethyl-3-(4-(trifluoromethyl)benzyl)naphthalene-1,4-dione

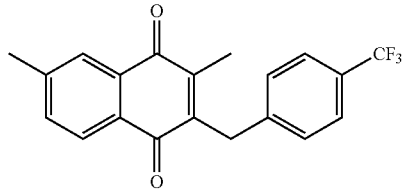 [SMILES: CC1=C(Cc2ccc(C(F)(F)F)cc2)C(=O)c2ccc(C)cc2C1=O]

Yield: 68% (yellow needles)

m.p. (from hexane/EtOAc): 102° C.

$^1$H NMR (300 MHz, CDCl$_3$): δ=7.98 (d, J=7.1 Hz, 1H), 7.88 (s, 1H), 7.51 (d, J=7.1 Hz, 1H), 7.44 ((AB)$_2$ system, J=7.3 Hz, Δν=52.0 Hz, 4H), 4.08 (s, 2H), 2.49 (s, 3H), 2.24 (s, 3H) ppm.

$^{13}$C NMR (75 MHz, CDCl$_3$): δ=185.4 (C=O); 184.4 (C=O); 144.8 (C$_q$); 144.6 (C$_q$); 144.3 (C$_q$); 142.3 (C$_q$); 134.4 (CH); 130.0 (C$_q$); 129.0 (C$_q$); 128.7 (q, J=31 Hz, C$_q$); 126.8 (2×CH) 125.5 (q, J=3.8 Hz, 2×CH); 124.1 (q, J=275.0 Hz, CF$_3$); 32.3 (CH$_2$); 21.8 (CH$_3$); 13.3 (CH$_3$) ppm.

MS (EI): m/z (%): 345.11 ([M$^+$], 100), 346.11 ([M+H$^+$], 25), elemental analysis calcd (%) for C$_{20}$H$_{15}$F$_3$O$_2$: C, 69.76; H, 4.39. Found C, 69.42; H, 4.49.

12.24. 2,7-dimethyl-3-(4-bromobenzyl)naphthalene-1,4-dione

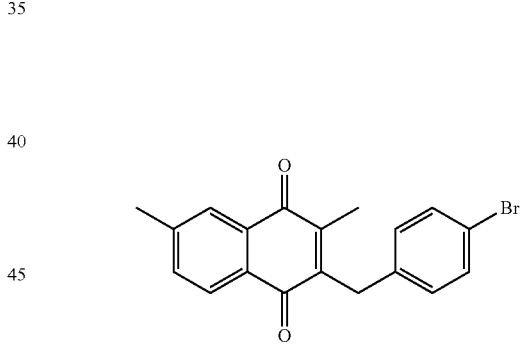

Yield: 70% (yellow needles)

m.p. (from hexane/EtOAc): 122-123° C.

$^1$H NMR (300 MHz, CDCl$_3$): δ=7.97 (d, J=7.9 Hz, 1H), 7.88 (s, 1H), 7.50 (d, J=7.9 Hz, 1H), 7.24 ((AB)$_2$ system, J=8.5 Hz, Δν=83.3 Hz, 4H), 4.08 (s, 2H), 2.49 (s, 3H), 2.24 (s, 3H) ppm.

$^{13}$C NMR (75 MHz, CDCl$_3$): δ=185.5 (C=O); 184.8 (C=O); 144.4 (C$_q$); 144.2 (C$_q$); 143.3 (C$_q$); 137.3 (C$_q$); 131.6 (2×CH); 130.3 (2×CH); 130.1 (C$_q$); 129.9 (C$_q$); 127.5 (CH); 127.3 (CH); 120.2 (C$_q$); 31.8 (CH$_2$); 20.2 (CH$_3$); 13.2 (CH$_3$) ppm.

MS (EI): m/z (%): 355.03 ([M$^+$], 100), 356.04 ([M+H$^+$], 25), elemental analysis calcd (%) for $C_{19}H_{15}BrO_3$: C, 64.24; H, 4.26. Found C, 64.05; H, 4.33.

12.25. 2,8-dimethyl-3-(4-(trifluoromethyl)benzyl)naphthalene-1,4-dione

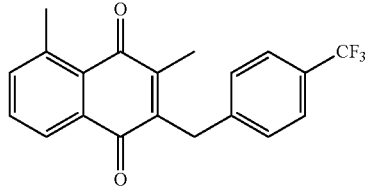 [SMILES: CC1=C(Cc2ccc(C(F)(F)F)cc2)C(=O)c2cccc(C)c2C1=O]

Yield: 75% (yellow needles)

m.p. (from hexane/EtOAc): 98-99° C.

$^1$H NMR (300 MHz, CDCl$_3$): δ=7.99 (dd, J=7.5 Hz, 1.2 Hz, 1H), 7.50-7.41 (m, 2H), 7.35 ((AB)$_2$ system, J=7.5 Hz, Δν=52.3 Hz, 4H), 3.98 (s, 2H), 2.66 (s, 3H), 2.15 (s, 3H) ppm.

$^{13}$C NMR (75 MHz, CDCl$_3$): δ=187.0 (C=O); 184.9 (C=O); 146.2 (C$_q$); 142.8 (C$_q$); 142.4 (C$_q$); 142.3 (C$_q$); 137.6 (CH); 133.5 (C$_q$); 132.7 (CH); 129.7 (C$_q$); 128.8 (2×CH); 128.7 (q, J=31 Hz, C$_q$); 125.5 (q, J=3.8 Hz, 2×CH); 124.2 (q, J=273.0 Hz, CF$_3$); 125.3 (CH); 32.5 (CH$_2$); 22.9 (CH$_3$); 13.1 (CH$_3$) ppm.

MS (EI): m/z (%): 344.2 ([M$^+$], 28), 329.2 ([M$^+$-CH$_3$], 100)

elemental analysis calcd (%) for $C_{20}H_{15}F_3O_2$: C, 69.76; H, 4.39. Found C, 69.69; H, 4.53.

12.26. 2,8-dimethyl-3-(4-bromobenzyl)naphthalene-1,4-dione

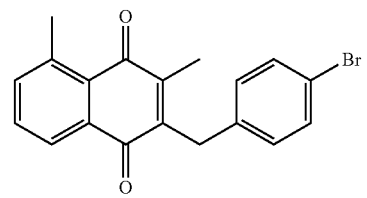 [SMILES: CC1=C(Cc2ccc(Br)cc2)C(=O)c2cccc(C)c2C1=O]

Yield: 67% (yellow needles)

m.p. (from hexane/EtOAc): 116-118° C.

$^1$H NMR (300 MHz, CDCl$_3$): δ=8.03 (dd, J=7.5 Hz, 1.5 Hz 1H), 7.59-7.49 (m, 2H), 7.27 ((AB)$_2$ system, J=8.0 Hz, Δν=40.9 Hz, 4H), 3.98 (s, 2H), 2.74 (s, 3H), 2.22 (s, 3H) ppm.

$^{13}$C NMR (75 MHz, CDCl$_3$): δ=187.1 (C=O); 185.0 (C=O); 145.9 (C$_q$); 143.1 (C$_q$); 141.0 (C$_q$); 137.5 (CH); 137.2 (C$_q$); 133.4 (C$_q$); 132.7 (CH); 131.7 (2×CH); 130.3 (2×CH); 129.8 (C$_q$); 125.4 (CH); 120.3 (C$_q$); 32.1 (CH$_2$); 22.9 (CH$_3$); 13.1 (CH$_3$) ppm.

MS (EI): m/z (%) 355.03 ([M$^+$], 100), 356.04 ([M+H$^+$], 27), elemental analysis calcd (%) for $C_{19}H_{15}BrO_3$: C, 64.24; H, 4.26. Found C, 64.19; H, 4.37.

12.27. 2,6,7-trimethyl-3-(4-(trifluoromethyl)benzyl)naphthalene-1,4-dione

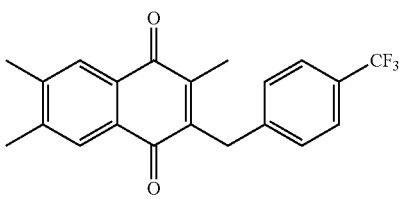 [SMILES: CC1=C(Cc2ccc(C(F)(F)F)cc2)C(=O)c2cc(C)c(C)cc2C1=O]

Yield: 87% (yellow needles)

m.p. (from hexane/EtOAc): 143-144° C.

$^1$H NMR (300 MHz, CDCl$_3$): δ=7.84 (s, 3H), 7.86 (s, 3H), 7.44 ((AB)$_2$ system, J=8.5 Hz, Δν=44.0 Hz, 4H), 4.07 (s, 2H), 2.74 (s, 3H), 2.40 (s, 3H), 2.39 (s, 3H) ppm.

$^{13}$C NMR (75 MHz, CDCl$_3$): δ=185.2 (C=O); 184.7 (C=O); 144.5 (C$_q$); 144.0 (C$_q$); 143.5 (C$_q$); 143.4 (C$_q$); 142.4 (C$_q$); 130.1 (C$_q$); 129.9 (C$_q$); 128.9 (2×CH); 128.7 (q, J=31.9 Hz, C$_q$); 127.5 (CH); 127.4 (CH); 125.5 (q, J=3.8 Hz, 2×CH); 124.1 (q, J=270.7 Hz, CF$_3$); 32.3 (CH$_2$); 20.2 (2×CH$_3$); 13.1 (CH$_3$) ppm.

MS (EI): m/z (%): 358.1 ([M$^+$], 26), 343.1 ([M$^+$-CH$_3$], 100)

elemental analysis calcd (%) for $C_{21}H_{17}F_3O_2$: C, 70.38; H, 4.78. Found C, 70.32; H, 4.96.

12.28. 2,6,7-trimethyl-3-(4-bromobenzyl)naphthalene-1,4-dione

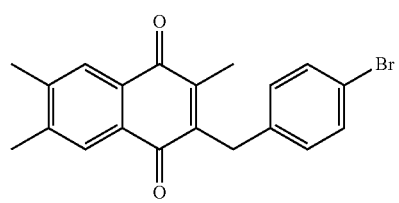 [SMILES: CC1=C(Cc2ccc(Br)cc2)C(=O)c2cc(C)c(C)cc2C1=O]

Yield: 82% (yellow needles)

m.p. (from hexane/EtOAc): 129-130° C.

$^1$H NMR (300 MHz, CDCl$_3$): δ=7.82 (s, 2H), 7.25 ((AB)$_2$ system, J=8.2 Hz, Δν=73.9 Hz, 4H), 3.98 (s, 2H), 2.39 (s, 6H), 2.22 (s, 3H) ppm.

$^{13}$C NMR (75 MHz, CDCl$_3$): δ=187.1 (C=O); 185.0 (C=O); 145.9 (C$_q$); 143.1 (C$_q$); 141.0 (C$_q$); 137.5 (CH); 137.2 (C$_q$); 133.4 (C$_q$); 132.7 (CH); 131.7 (2×CH); 130.3 (2×CH); 129.8 (C$_q$); 125.4 (CH); 120.3 (C$_q$); 32.1 (CH$_2$); 22.9 (CH$_3$); 13.1 (CH$_3$) ppm.

MS (EI): m/z (%): 368.1 ([M⁺], 26), 353.0 ([M⁺-CH₃], 100) elemental analysis calcd (%) for $C_{20}H_{17}BrO_2$: C, 65.05; H, 4.64. Found C, 64.66; H, 4.71.

12.29. 6-methyl-5,8-dioxo-7-(4-(trifluoromethyl)benzyl)-5,8-dihydronaphthalen-2-yl trifluoromethanesulfonate

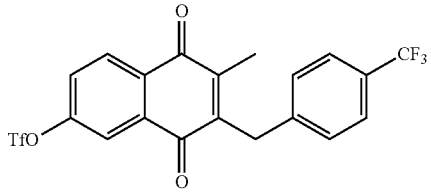 [SMILES: CC1=C(Cc2ccc(C(F)(F)F)cc2)C(=O)c2cc(OS(=O)(=O)C(F)(F)F)ccc2C1=O]

Yield: 70% (yellow needles)
m.p. (from hexane/EtOAc): 127° C.
¹H NMR (300 MHz, CDCl₃): δ=8.16 (d, J=8.6 Hz, 1H), 7.90 (d, J=2.7 Hz, 1H) 7.53 (dd, J=8.6 Hz, 2.7 Hz, 1H), 7.38 ((AB)₂ system, J=8.2 Hz, Δν=57.0 Hz, 4H), 4.03 (s, 2H), 2.21 (s, 3H) ppm.
¹³C NMR (75 MHz, CDCl₃): δ=183.4 (C=O); 182.6 (C=O); 152.9 ($C_q$); 145.0 ($C_q$); 141.6 ($C_q$); 141.6 ($C_q$); 134.0 ($C_q$); 131.4 ($C_q$); 129.4 (2×CH); 129.1 (q, J=33.1 Hz, $C_q$); 129.0 (CH); 128.0 (CH); 126.4 (CH), 125.5 (q, J=3.8 Hz, 2×CH); 124.1 (q, J=281.1 Hz, CF₃); 119.3 (CH); 118.7 (q, J=315.5 Hz, S—CF₃); 32.4 (CH₂); 13.4 (CH₃) ppm.
MS (EI): m/z (%): 478.0 ([M⁺], 23), 463.0 ([M⁺-CH₃], 100)
elemental analysis calcd (%) for $C_{20}H_{12}F_6O_5S$: C, 50.22; H, 2.83. Found C, 50.13; H, 2.84.

12.30. 7-methyl-5,8-dioxo-6-(4-(trifluoromethyl)benzyl)-5,8-dihydronaphthalen-2-yl trifluoromethanesulfonate

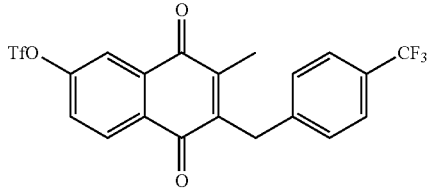 [SMILES: CC1=C(Cc2ccc(C(F)(F)F)cc2)C(=O)c2ccc(OS(=O)(=O)C(F)(F)F)cc2C1=O]

Yield: 75% (yellow needles)
m.p. (from hexane/EtOAc): 87-88° C.
¹H NMR (300 MHz, CDCl₃): δ=8.15 (d, J=8.6 Hz, 1H), 7.91 (d, J=2.5 Hz, 1H) 7.53 (dd, J=8.6 Hz, 2.5 Hz, 1H), 7.33 ((AB)₂ system, J=8.2 Hz, Δν=49.0 Hz, 4H), 4.02 (s, 2H), 2.21 (s, 3H) ppm.
¹³C NMR (75 MHz, CDCl₃): δ=183.2 (C=O); 182.8 (C=O); 152.9 ($C_q$); 145.2 ($C_q$); 145.2 ($C_q$); 144.9 ($C_q$); 134.2 ($C_q$); 129.6 (CH); 129.1 (q, J=31.4 Hz, $C_q$); 128.7 (2×CH); 126.4 (CH); 125.7 (q, J=3.8 Hz, 2×CH), 124.0 (q, J=275.8 Hz, CF₃); 119.2 (CH); 118.7 (q, J=319.9 Hz, S—CF₃); 32.4 (CH₂); 13.5 (CH₃) ppm.
MS (EI): m/z (%): 478.0 ([M⁺], 20), 463.0 ([M⁺-CH₃], 100)
elemental analysis calcd (%) for $C_{20}H_{12}F_6O_5S$: C, 50.22; H, 2.83. Found C, 50.27; H, 2.79.

EXAMPLE 13

General Procedure for the Synthesis of Hydroxymenadione Derivatives by Triflate Deprotection To a solution of trifluoromethanesulfonic ester (1 eq) in THF (0.2M), TBAF×3H₂O (3 eq) was added. The mixture was stirred for 3 h, diluted with EtOAc (10 mL) and the THF was evaporated. The mixture was neutralized with 1 N aqueous HCl solution. The organic layer was dried over anhydrous MgSO₄, concentrated in vacuo and purified by column chromatography EtOAc/Cyclohexane 4:1 to give the hydroxynaphthoquinone.

13.1 6-hydroxy-3-methyl-2-(4-(trifluoromethyl)benzyl)naphthalene-1,4-dione

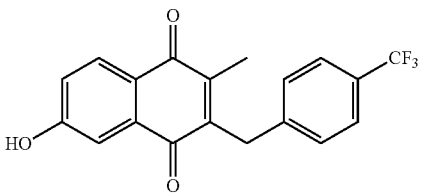 [SMILES: CC1=C(Cc2ccc(C(F)(F)F)cc2)C(=O)c2cc(O)ccc2C1=O]

Yield: 70% (yellow needles)
m.p. (from hexane/EtOAc): >200° C. dec.
¹H NMR (400 MHz, DMSO): δ=10.81 (bs, 1H), 7.85 (d, J=8.5 Hz, 1H), 7.61 ((AB)₂ system, J=8.9 Hz, Δν=53.0 Hz, 4H), 7.30 (d, J=2.5 Hz, 1H) 7.13 (dd, J=8.5 Hz, 2.6 Hz, 1H), 4.03 (s, 2H), 2.10 (s, 3H) ppm.
¹³C NMR (100 MHz, DMSO): δ=184.7 (C=O); 183.8 (C=O); 163.1 ($C_q$); 145.1 ($C_q$); 143.8 ($C_q$); 143.5 ($C_q$); 134.1 ($C_q$); 129.5 (2×CH); 129.4 (CH); 127.3 (q, J=31.4 Hz, $C_q$); 125.8 (q, J=3.9 Hz, 2×CH), 124.8 (q, J=275.6 Hz, $C_q$); 121.1 (CH); 111.7 (CH); 32.1 (CH₂); 13.5 (CH₃) ppm.
MS (EI): m/z (%): 346.04 ([M⁺], 100), 357.04 ([M+H⁺], 15),
elemental analysis calcd (%) for $C_{19}H_{13}F_3O_3$ C, 65.90; H, 3.78. Found C, 65.73; H, 3.85.

13.2 7-hydroxy-3-methyl-2-(4-(trifluoromethyl)benzyl)naphthalene-1,4-dione

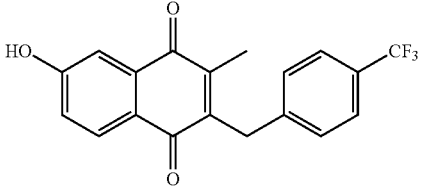 [SMILES: CC1=C(Cc2ccc(C(F)(F)F)cc2)C(=O)c2ccc(O)cc2C1=O]

Yield: 60% (yellow needles)
m.p. (from hexane/EtOAc): >200° C., dec.
¹H NMR (300 MHz, DMSO): δ=10.81 (bs, 1H), 7.87 (d, J=8.5 Hz, 1H), 7.44 ((AB)₂ system, J=8.9 Hz, Δν=53.0 Hz, 4H), 7.31 (d, J=2.6 Hz, 1H) 7.14 (dd, J=8.5 Hz, 2.6 Hz, 1H), 4.05 (s, 2H), 2.12 (s, 3H) ppm.
¹³C NMR (75 MHz, DMSO): δ=184.8 (C=O); 182.8 (C=O); 162.6 ($C_q$); 144.1 ($C_q$); 143.6 ($C_q$); 143.4 ($C_q$); 143.3 (CH); 133.8 ($C_q$); 129.1 (2×CH); 129.0 (CH); 126.8 (q, J=31.6 Hz, $C_q$); 125.6 (q, J=3.8 Hz, 2×CH); 124.2 (q, J=275.9 Hz, $CF_3$); 120.3 (CH); 111.6 (CH); 31.5 ($CH_2$); 12.9 ($CH_3$) ppm.

MS (EI): m/z (%): 346.1 ([M+], 32), 331.0 ([$M^+$-$CH_3$], 100)

elemental analysis calcd (%) for $C_{19}H_{13}F_3O_3C$, 65.90; H, 3.78. Found C, 66.13; H, 3.67.

EXAMPLE 14

General Procedure for the Synthesis of Compounds Ia4

The corresponding azamenadione derivatives, compounds of formula (II), (1 eq, 0.05 mmol·$mL^{-1}$) and a phenyl acetic acid derivative (compounds of formula (III)) (2 eq) were added to a stirred solution of $MeCN/H_2O$ (3/1) and heated at 85° C. (70° C. in the flask). $AgNO_3$ (0.35 eq) was added first and then $(NH_4)_2S_2O_8$ (1.3 eq, 0.36 mmol·$mL^{-1}$) in $MeCN/H_2O$ (3/1) was added dropwise. The reaction mixture was then heated 2-3 hours at 85° C. MeCN was evaporated and the mixture was extracted with DCM. The crude mixture was purified by flash chromatography on silica gel using a mixture diethyl ether and toluene (70/30). When necessary, the compound was further purified by trituration in diethyl ether.

14.1. 6-(4-bromobenzyl)-7-methylquinoline-5,8-dione

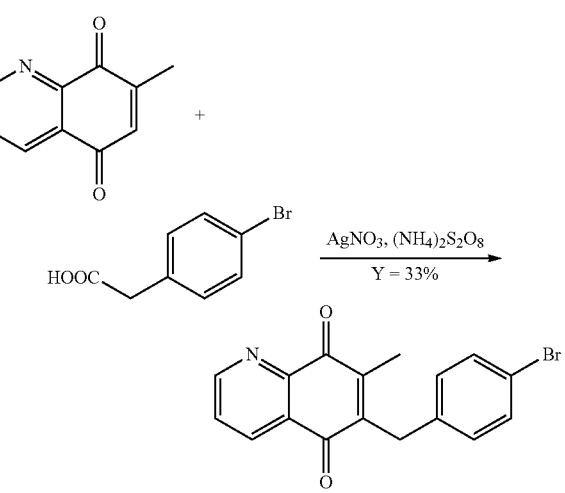

Yield: 33% m.p. 105-106° C.

$^1$H NMR (300 MHz, $CDCl_3$): δ=9.02 (s, 1H), 8.43 (d, J=7.5 Hz, 1H), 7.64-7.66 (d, J=6.1 Hz, 1H), 7.26 (($AB)_2$ system, J=8.3 Hz, Δv=72.4 Hz, 4H), 4.05 (s, 2H), 2.27 (s, 3H) ppm $^{13}$C NMR (75 MHz, $CDCl_3$): δ=184.7 (C=O), 183.0 (C=O), 154.6 (CH), 147.4 ($C_q$), 145.9 ($C_q$), 144.1 ($C_q$), 136.5 ($C_q$), 134.5 (CH), 131.8 (2×CH), 130.6 (2×CH), 128.9 ($C_q$), 127.6 (CH), 120.5 ($C_q$), 32.0 ($CH_2$), 13.3 ($CH_3$) ppm EI MS (70 eV, m/z (%)): 341.0 ([$M]^+$, 17), 325.9 ([M-$CH_3]^+$, 57), elemental analysis calcd. for $C_{17}H_{12}BrNO_2$: C, 59.67; H, 3.53; N, 4.09; Br, 23.35. Found: C, 59.57; H, 3.65; N, 4.02; Br, 23.13.

14.2. 6-(2,5-dimethoxybenzyl)-3,7-dimethylquinoline-5,8-dione

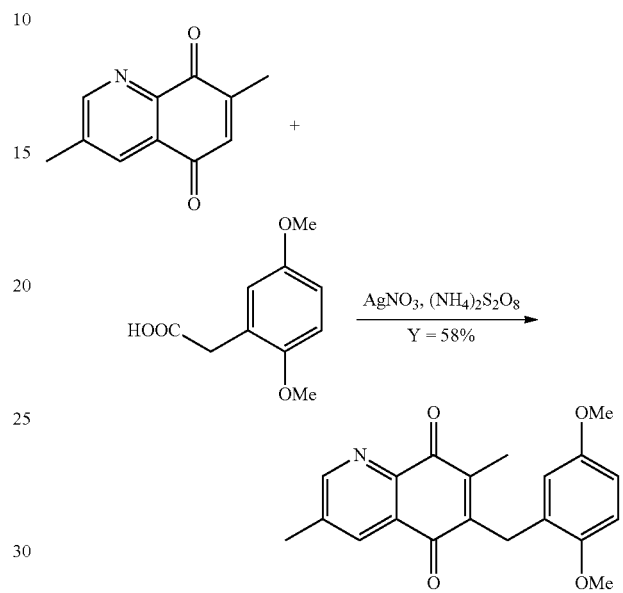

Yield: 58% m.p.: 133-135° C.

$^1$H NMR (300 MHz, $CDCl_3$): δ=8.81 (d, J=2.1 Hz, 1H), 8.18 (d, J=2.1 Hz, 1H), 6.77-6.66 (m, 3H), 4.05 (s, 2H), 3.78 (s, 3H), 3.70 (s, 3H), 2.51 (s, 3H), 2.18 (s, 3H) ppm $^{13}$C NMR (75 MHz, $CDCl_3$): δ=184.3 (C=O), 183.7 (C=O), 154.8 (CH), 153.5 ($C_q$), 151.5 ($C_q$), 145.8 ($C_q$), 145.5 ($C_q$), 144.9 ($C_q$), 138.3 ($C_q$), 134.4 (CH), 128.6 ($C_q$), 127.2 ($C_q$), 116.3 (CH), 111.2 (CH), 111.1 (CH), 55.9 ($CH_3$), 55.6 ($CH_3$), 26.9 ($CH_2$), 18.9 ($CH_3$), 13.2 ($CH_3$) ppm EI MS (70 eV, m/z (%)): 337.13 ([$M]^+$, 65), 322.1 ([M-$CH_3]^+$, 100);

elemental analysis calcd. for $C_{20}H_{19}NO_4$: C, 71.20; H, 5.68; N, 4.15. Found: C, 71.35; H, 5.75; N, 4.20.

14.3. 6-(4-bromobenzyl)-3,7-dimethylquinoline-5,8-dione

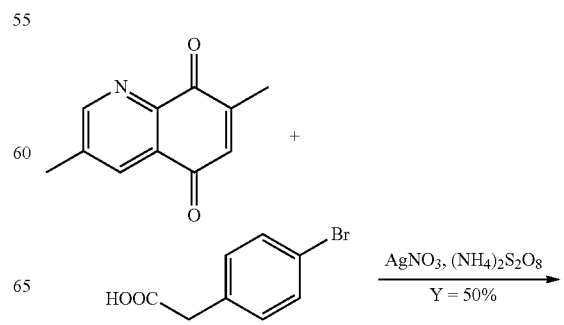

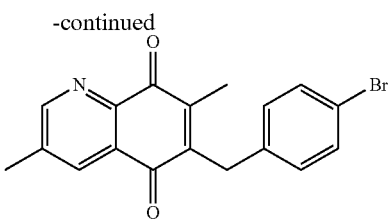

Yield: 50% m.p.: 146-148° C. (Et$_2$O)

$^1$H NMR (300 MHz, CDCl$_3$): δ=8.83 (d, J=2.0 Hz, 1H), 8.20 (d, J=2.0 Hz, 1H), 7.26 ((AB)$_2$ system, J=8.0 Hz, Δν=72.4 Hz, 4H), 4.04 (s, 2H), 2.52 (s, 3H), 2.26 (s, 3H) ppm $^{13}$C NMR (75 MHz, CDCl$_3$): δ=185.0 (C=O), 182.9 (C=O), 155.1 (CH), 145.7 (C$_q$), 145.3 (C$_q$), 143.8 (C$_q$), 138.5 (C$_q$), 136.6 (C$_q$), 134.2 (CH), 131.7 (2×CH), 130.5 (2×CH), 128.5 (C$_q$), 120.4 (C$_q$), 31.9 (CH$_2$), 18.9 (CH$_3$), 13.2 (CH$_3$) ppm elemental analysis calcd. for C$_{18}$H$_{14}$BrNO$_2$: C, 60.69; H, 3.96; N, 3.93; Br, 22.43. Found: C, 60.92; H, 4.02; N, 3.89; Br, 22.28.

14.4. 6-(3,5-dimethoxybenzyl)-3,7-dimethylquinoline-5,8-dione

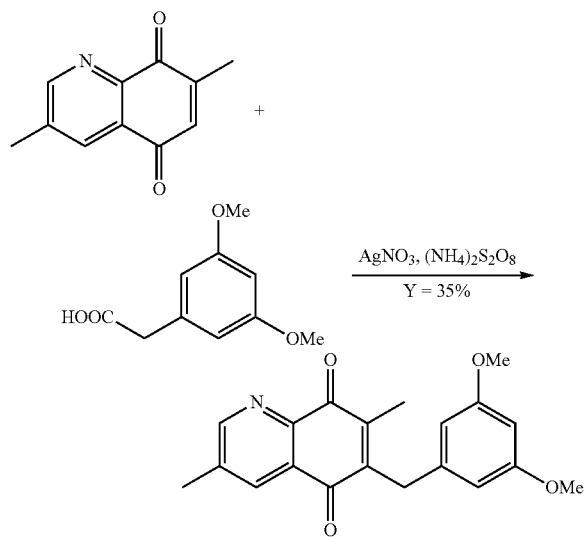

3,7-dimethylquinoline-5,8-dione (250 mg, 1.34 mmol, 1 equiv.) and 2-(3,5-dimethoxyphenyl)acetic acid (524.08 mg, 2.67 mmol, 2 equiv) gave a mixture which was purified by column chromatography using diethyl ether and toluene (70/30) to give a yellow solid.

This solid was triturated in diethyl ether, filtrated and dried under vacuum to afford 22 (160 mg, 0.47 mmol, 35%).

m.p.: 106-108° C. (Et$_2$O)

$^1$H NMR (300 MHz, CDCl$_3$): δ=8.83 (d, J=2.1 Hz, 1H), 8.20 (d, J=2.1 Hz, 1H), 6.41-6.29 (m, 3H), 4.03 (s, 2H), 3.74 (s, 6H), 2.52 (s, 3H), 2.27 (s, 3H) ppm $^{13}$C NMR (75 MHz, CDCl$_3$): δ=185.1 (C=O), 182.9 (C=O), 160.9 (C$_q$), 155.0 (CH), 145.9 (C$_q$), 145.3 (C$_q$), 143.9 (C$_q$), 139.8 (C$_q$), 138.4 (C$_q$), 134.2 (CH), 128.5 (CH), 107.0 (C$_q$), 98.3 (C$_q$), 32.5 (CH$_2$), 18.8 (CH$_3$), 13.2 (CH$_3$) ppm EI MS (70 eV, m/z (%)): 337.0 ([M]$^+$, 41), 322.0 ([M−CH$_3$]$^+$, 100)

elemental analysis calcd. for C$_{20}$H$_{19}$NO$_4$: C, 71.20; H, 5.68; N, 4.15. Found: C, 70.85; H, 5.70; N, 4.15.

analysis calcd. for C$_{20}$H$_{19}$NO$_4$: C, 71.20; H, 5.68; N, 4.15. Found: C, 70.85; H, 5.70; N, 4.15.

14.5. 3,7-dimethyl-6-(4-(trifluoromethyl)benzyl)quinoline-5,8-dione

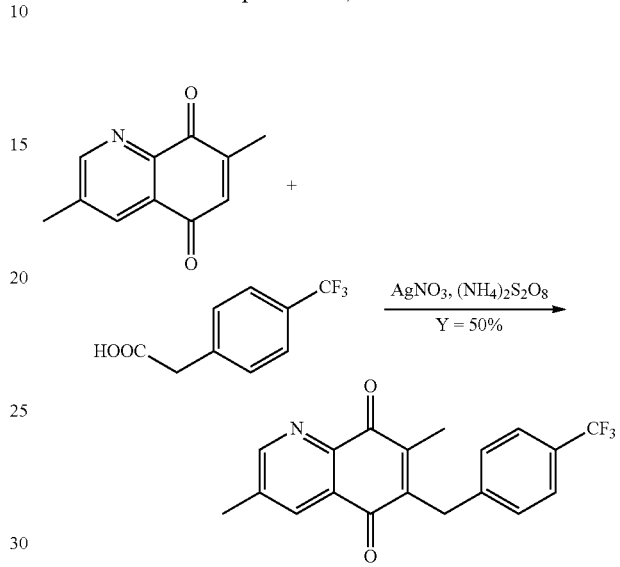

3,7-dimethylquinoline-5,8-dione (250 mg, 1.34 mmol, 1 equiv.) and 2-(4-(trifluoromethyl)phenyl)acetic acid (545.39 mg, 2.67 mmol, 2 equiv.) gave a mixture which was purified by column chromatography using diethyl ether and toluene (80/20) to give a brown solid.

This solid was triturated in diethyl ether, filtrated and dried under vacuum to afford the final compound (230 mg, 0.66 mmol, 50%).

m.p.: 121-123° C. (Et$_2$O)

$^1$H NMR (300 MHz, CDCl$_3$): δ=8.83 (s, 1H), 8.21 (s, 1H), 7.45 ((AB)$_2$ system, J=7.8 Hz, Δν=41.9 Hz), 4.14 (s, 2H), 2.52 (s, 3H), 2.27 (s, 3H) ppm $^{13}$C NMR (75 MHz, CDCl$_3$): δ=184.9 (C=O), 182.9 (C=O), 155.2 (CH), 145.3 (C$_q$), 145.2 (C$_q$), 141.7 (C$_q$), 143.2 (CH), 138.6 (C$_q$), 129.1 (2×CH), 128.9 (q, J$_{C-F}$=25.6 Hz, C$_q$), 128.5 (C$_q$), 125.6 (q, J$_{C-F}$=3.7 Hz, 2×CH), 124.0 (q, J$_{C-F}$=272.6 Hz, C$_q$), 32.3 (CH$_2$), 18.9 (CH$_3$), 13.3 (CH$_3$) ppm EI MS (70 eV, m/z (%)): 345.0 ([M]$^+$, 41), 330.0 ([M−CH$_3$]$^+$, 100)

elemental analysis calcd. for C$_{19}$H$_{14}$F$_3$NO$_2$: C, 66.09; H, 4.09; F, 16.51; N, 4.06. Found: C, 66.15; H, 4.12; N, 4.08.

14.6. 7-methyl-6-(4-(trifluoromethyl)benzyl)quinoline-5,8-dione

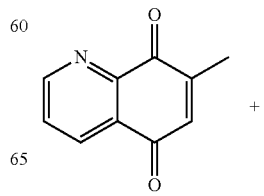

-continued

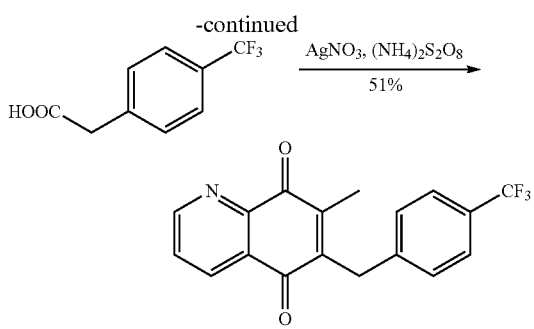

Yield: 51%

$^{1}$H NMR (300 MHz, CDCl$_3$): δ=8.95 (dd, J=4.7 Hz, 1.7 Hz, 1H), 8.36 (dd, J=7.9 Hz, 1.7 Hz, 1H), 7.59 (dd, J=7.9 Hz, 4.7 Hz, 1H), 7.38 ((AB)$_2$ system, J=8.5 Hz, Δv=41.5 Hz, 4H), 4.08 (s, 2H), 2.21 (s, 3H) ppm $^{13}$C NMR (75 MHz, CDCl$_3$): δ=184.0 (C=O), 182.9 (C=O), 154.6 (CH), 147.4 (C$_q$), 145.5 (C$_q$), 144.3 (C$_q$), 134.5 (CH), 129.1 (2×CH), 127.6, (CH), 128.7 (C$_q$), 127.6 (CH), 125.6 (q, J=3.8 Hz, 2×CH); 122.2 (C$_q$), 32.3 (CH$_2$), 13.7 (CH$_3$) ppm MS (EI): m/z (%): 331.0 ([M]$^+$, 41), 316.1 ([M-CH$_3$]$^+$, 100)

elemental analysis calcd (%) for C$_{18}$H$_{12}$F$_3$NO$_2$: C, 65.26; H, 3.65; N, 4.23. Found C, 65.28; H, 3.71; N, 4.23.

m.p. 107-109° C.

14.7. 6-(2,5-dimethoxybenzyl)-7-methylquinoline-5,8-dione

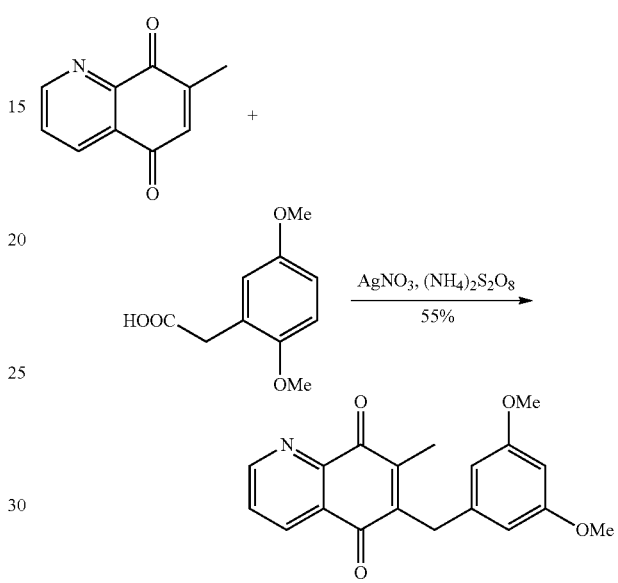

Yield: 45%

$^{1}$H NMR (300 MHz, CDCl$_3$): δ=9.02 (dd, J=4.7 Hz, J=1.7 Hz, 1H), 8.44 (dd, J=7.9 Hz, J=1.7 Hz, 1H), 7.66 (dd, J=7.8 Hz, J=4.7 Hz, 1H), 6.80-6.70 (m, 3H), 4.08 (s, 2H), 3.80 (s, 3H), 3.73 (s, 3H), 2.80 (s, 3H) ppm $^{13}$C NMR (75 MHz, CDCl$_3$): δ=184.9 (C=O), 183.0 (C=O), 154.3 (CH), 153.6 (C$_q$), 151.5 (C$_q$), 147.8 (C$_q$), 146.6 (C$_q$), 144.4 (C$_q$), 134.4 (CH), 129.0 (C$_q$), 127.3 (CH), 127.1 (C$_q$), 116.5 (CH), 111.6 (CH), 111.3 (CH), 56.0 (CH$_3$), 55.7 (CH$_3$), 27.1 (CH$_2$), 13.1 (CH$_3$) ppm EI MS (70 eV, m/z (%)): 323.2 ([M]$^+$, 53), 308.1 ([M-CH$_3$]$^+$, 100), 293.1 (43), elemental analysis calcd. for C$_{19}$H$_{17}$NO$_4$·0.45H$_2$O: C, 68.85; H, 5.44; N, 4.23. Found: C, 68.25; H, 5.30; N, 4.28.

m.p. 135-137° C.

14.8. 6-(3,5-dimethoxybenzyl)-7-methylquinoline-5,8-dione

Yield: 55%

$^{1}$H NMR (300 MHz, CDCl$_3$): δ=9.02 (dd, J=4.7 Hz, J=1.7 Hz, 1H), 8.44 (dd, J=7.9 Hz, J=1.7 Hz, 1H), 7.66 (dd, J=7.8 Hz, J=4.7 Hz, 1H), 6.41 (d, J=2.2 Hz, 2H), 6.29 (t, J=2.2 Hz, 1H), 4.04 (s, 2H), 3.75 (s, 6H), δ=2.33 (s, 3H) ppm $^{13}$C NMR (75 MHz, CDCl$_3$): δ=184.8 (C=O), 183.0 (C=O), 160.9 (C$_q$), 154.4 (CH), 147.5 (C$_q$), 146.0 (C$_q$), 144.1 (C$_q$), 139.7 (C$_q$), 134.4 (CH), 128.9 (C$_q$), 127.5 (CH), 107.4 (2×CH), 98.3 (CH), 55.3 (2×OCH$_3$), 32.6 (CH$_2$), 13.3 (CH$_3$) ppm EI MS (70 eV, m/z (%)): 323.2 ([M]$^+$, 42), 308.1 ([M-CH$_3$]$^+$, 100), 166.1 (77), 293.1 (58), 173.0 (53), 166.1 (77).

elemental analysis calculated for C$_{19}$H$_{17}$NO$_4$: C, 70.58; H, 5.30; N, 4.33. Found: C, 70.30; H, 5.41; N, 4.26.

EXAMPLE 15

Synthesis of Azamenadiones (Compounds IIa4)

7-methylquinoline-5,8-dione (R=H)

3,7-dimethylquinoline-5,8-dione (R=Me)

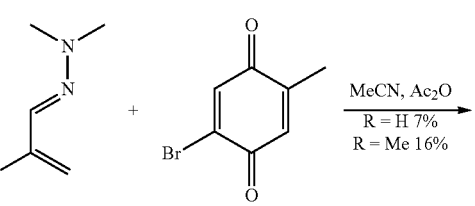

-continued

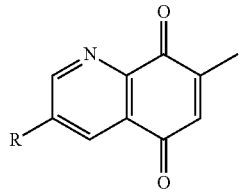

(E)-1,1-dimethyl-2-(2-methylallylidene)hydrazine (2.18 g, 19.50 mmol, 1.3 equiv.) and acetic anhydride (19.15 mL) were added in 250 mL of MeCN and stirred at room temperature. 2-bromo-5-methylcyclohexa-2,5-diene-1,4-dione (3 g, 14.9 mmol, 1 equiv.) in 125 mL of MeCN was then added dropwise (slowly during 60 min). The reaction mixture was stirred at room temperature during 120 minutes.

The crude was then concentrated and purified by column chromatography using diethyl ether and toluene (80/20) to give a brown solid.

This solid was triturated in diethyl ether, filtrated and dried under vacuum to give 452 mg, 2.41 mmol, 16%)

m.p.: 178-180° C.

$^1$H NMR (300 MHz, CDCl$_3$): δ=8.85 (s, 1H), 8.22 (s, 1H), 6.97-6.98 (d, $^4$J=1.5 Hz, 1H), 2.53 (s, 3H), 2.22-2.23 (d, $^4$J=1.5 Hz, 3H) ppm $^{13}$C NMR (75 MHz, CDCl$_3$): δ=184.56 (C=O), 183.68 (C=O), 155.09 (CH), 149.04 (C$_q$), 145.63 (C$_q$), 138.65 (C$_q$), 134.86 (CH), 133.94 (CH), 128.67 (C$_q$), 18.86 (CH$_3$), 16.69 (CH$_3$) ppm elemental analysis calculated for C$_{11}$H$_9$NO$_2$: C, 70.58; H, 4.85; N, 7.48. Found: C, 70.27; H, 4.74; N, 7.26.

EXAMPLE 16

Synthesis of Compound of Formula (XXIII)

16.1. Condensation of the 2-bromo-1.4-dimethoxy-3-methylnaphthalene derivative and a starting benzoylchloride derivative General Procedure:

The 2-bromo-1,4-dimethoxy-3-methylnaphthalene derivative (Bauer H, Fritz-Wolf K, Winzer A, Kühner S, Little S, Yardley V, Vezin H, Palfey B, Schirmer R H, Davioud-Charvet E. J Am Chem. Soc. 2006, 128:10784-94) (1.0 equiv.) was placed in an Argon flushed flask. Dry THF was added and the mixture was cooled to −78° C. BuLi (1.1 equiv.) was added dropwise and the mixture was stirred 10 min at −78° C. Then, the benzoylchloride (1.1 equiv.) was added under stirring and the reaction mixture was stirred at −78° C. for 30 min. The reaction mixture was then allowed to warm to RT. The mixture was poured into a 20 mL 1:1 mixture of diluted HCl:saturated NaCl and it was extracted twice with 20 mL Et$_2$O. The organic phase was dried over MgSO$_4$ and evaporated. The resulting oil was purified through flash chromatography.

16.1.1. (1.4-dimethoxy-3-methylnaphthalen-2-yl)(2-fluorophenyl)methanone LJ103

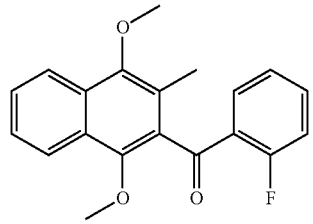 [SMILES: COc1c(C)c(C(=O)c2ccccc2F)c(OC)c2ccccc12]

2-bromo-1,4-dimethoxy-3-methylnaphthalene (500 mg. 1.78 mmol) and commercially available 2-fluorobenzoyl-chloride (307 mg. 1.96 mmol) were treated according to general procedure 12.1. The resulting orange oil was purified through flash chromatography (Cyclohexane:EtOAc 10:1). The product was obtained as a white powder. Rf(Cyclohexane:EtOAc 10:1)=0.28. Yield=295 mg (51%).

$^1$H NMR (300 MHz, CDCl$_3$): δ=8.03-8.06 (m, 1H), 7.95-7.98 (m, 1H), 7.68 (cm, 1H), 7.39-7.51 (m, 3H), 7.12 (cm, 1H), 7.02 (ddd, $^3$J$_{HF}$=11 Hz, $^3$J$_{HH}$=8 Hz, $^4$J$_{HH}$=1 Hz, 1H), 3.82 (s, 3H), 3.72 (s, 3H, OCH$_3$), 2.22 (s, 3H, OCH$_3$) ppm.

$^{13}$C NMR (75 MHz, CDCl$_3$): δ=194.34 (C=O), 161.93 (d. $^1$J$_{CF}$=260 Hz. Cq-F), 150.50 (Cq-O), 149.31 (Cq-O), 135.05 (CHar), 132.54 (Cq), 131.58 (CHar), 129.50 (Cq), 127.15 (CHar), 126.87 (Cq), 126.75 (Cq), 125.93 (CHar), 124.32 (CHar), 123.41 (Cq), 122.68 (CHar), 122.45 (CHar), 116.97 (CHar-F), 63.48 (OCH$_3$), 61.51 (OCH$_3$), 12.73 (CH$_3$) ppm.

$^{19}$F NMR (282 MHz, CDCl$_3$): δ=−111.81 (cm, $^3$J$_{HF}$=11 Hz, $^4$J$_{HF}$=7 Hz)

EA calcd for C$_{20}$H$_{17}$O$_3$F (%): C, 74.06; H, 5.28; O, 14.80. Found: C, 73.76; H, 5.40.

Mp=133-135°

16.1.2. (1.4-dimethoxy-3-methylnaphthalen-2-yl)(2-fluoro-3-trifluoromethyl) phenyl)methanone LJ116

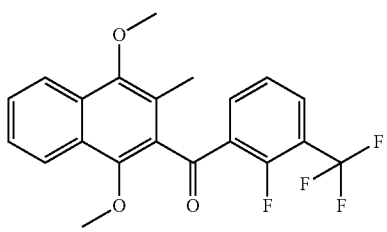 [SMILES: COc1c(C)c(C(=O)c2cccc(C(F)(F)F)c2F)c(OC)c2ccccc12]

2-bromo-1.4-dimethoxy-3-methylnaphthalene (100 mg. 0.356 mmol) and commercially available 2-fluoro-3-trifluoromethyl-benzoylchloride (90 mg. 0.392 mmol) were treated according to general procedure 12.1. The resulting brown oil was purified through flash chromatography (Cyclohexane:EtOAc 10:1). The product was obtained as yellow oil. Rf(Cyclohexane:EtOAc 10:1)=0.35. Yield=45 mg (32%).

$^1$H NMR (300 MHz, CDCl$_3$): δ=8.13-8.15 (m, 1H). 8.03-8.05 (m, 1H). 7.92-7.98 (m, 1H). 7.79-7.83 (m, 1H). 7.50-

7.62 (cm, 2H), 7.31-7.36 (m, 1H). 3.92 (s, 3H, OCH$_3$). 3.79 (s, 3H, OCH$_3$). 2.33 (s, 3H, CH$_3$) ppm.

$^{13}$C NMR (75 MHz, CDCl$_3$): δ=193.18 (C=O), 159.01 (d, $^1J_{CF}$=269 Hz, Cq-F), 150.69 (Cq-O), 149.83 (Cq-O), 137.21 (CHar), 135.06 (CHar), 133.43 (Cq), 131.64 (Cq), 131.51 (CHar), 128.50 (Cq), 128.43 (q, $^1J_{CF}$=259 Hz, CF$_3$), 128.38 (Cq), 127.52 (CHar), 126.13 (CHar), 124.40 (Cq), 124.18 (CHar), 123.32 (Cq), 122.62 (CHar), 63.55 (OCH$_3$), 61.57 (OCH$_3$), 12.77 (CH$_3$) ppm.

EI MS (70 eV, m/z (%): 392.0 ([M+], 25)

16.1.3. (1.4-dimethoxy-3-methylnaphthalen-2-yl)(2-fluoro-4-(trifluoromethyl) phenyl)methanone LJ123

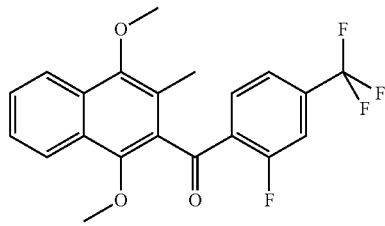 [SMILES: COc1c(C)c(C(=O)c2ccc(C(F)(F)F)cc2F)c(OC)c2ccccc12]

2-bromo-1.4-dimethoxy-3-methylnaphthalene (300 mg, 1.07 mmol) and commercially available 2-fluoro-4-trifluoromethyl-benzoylchloride (265 mg. 1.17 mmol) were treated according to general procedure 12.1. The resulting yellow oil was purified through flash chromatography (Cyclohexane:EtOAc 10:1). The product was obtained as a yellow oil. Rf(Cyclohexane:EtOAc 10:1)=0.50. Yield=175 mg (42%).

$^1$H NMR (300 MHz, CDCl$_3$): δ=8.13-8.15 (m, 1H). 8.03-8.05 (m, 1H). 7.92-7.98 (m, 1H). 7.79-7.83 (m, 1H). 7.50-7.62 (cm, 2H), 7.31-7.36 (m, 1H). 3.92 (s, 3H, OCH$_3$). 3.79 (s, 3H, OCH$_3$). 2.33 (s, 3H, CH$_3$) ppm.

$^{13}$C NMR (75 MHz, CDCl$_3$): δ=193.18 (C=O), 159.01 (d, $^1J_{CF}$=269 Hz, Cq-F), 150.69 (Cq-O), 149.83 (Cq-O), 137.21 (CHar), 135.06 (CHar), 133.43 (Cq), 131.64 (Cq), 131.51 (CHar), 128.50 (Cq), 128.43 (q, $^1J_{CF}$=259 Hz, CF$_3$), 128.38 (Cq), 127.52 (CHar), 126.13 (CHar), 124.40 (Cq), 124.18 (CHar), 123.32 (Cq), 122.62 (CHar), 63.55 (OCH$_3$), 61.57 (OCH$_3$), 12.77 (CH$_3$) ppm.

EI MS (70 eV, m/z (%): 392.0 ([M+], 25)

EXAMPLE 17

Synthesis of Compounds of Formula (Ib)

17.1. Selective Demethylation

General Procedure:

A solution of the 1.4-dimethoxy-3-methylnaphthalen-2-yl)(substituted-phenyl)methanone (1.0 equiv.) in dry DCM was cooled to 0° C. and kept stirring for 30 min. Then, BBr3 (1.0 equiv., 1M in DCM) was added dropwise to the solution and the reaction mixture was stirred at 0° C. for 2 h (TLC control). The reaction mixture was quenched with MeOH. Saturated NaCl was added to the mixture which was extracted three times with DCM and twice with EtOAc. The organic layers were combined, dried over MgSO$_4$ and evaporated.

17.1.1. (2-fluorophenyl)(1-hydroxy-4-methoxy-3-methylnaphthalen-2-yl) methanone LJ108

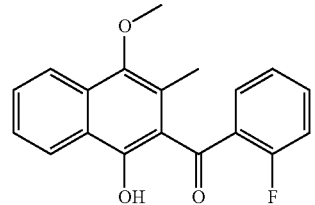 [SMILES: COc1c(C)c(C(=O)c2ccccc2F)c(O)c2ccccc12]

(1,4-dimethoxy-3-methylnaphthalen-2-yl)(2-fluorophenyl)methanone LJ103 (75 mg, 0.231 mmol) was treated according to general procedure 12.1. The product was obtained as a yellow powder. Rf(Cyclohexane:DCM 3:2)=0.29. Yield=68 mg (94%).

$^{13}$C NMR (75 MHz, CDCl$_3$): δ=197.52 (C=O), 159.33 (d, $^1J_{CF}$=253 Hz, Cq-F), 158.69 (Cq), 146.71 (Cq), 133.28 (d, $^3J_{CF}$=8 Hz, CHar), 131.92 (Cq), 130.43 (CHar), 130.20 (d, $^2J_{CF}$=14 Hz, Cq-F), 129.76 (d, $^4J_{CF}$=3 Hz, CHar), 125.72 (CHar), 124.92 (CHar), 124.56 (d, $^3J_{CF}$=6 Hz, CHar-F), 123.38 (Cq), 123.36 (Cq), 121.80 (CHar), 116.42 (d, $^2J_{CF}$=21 Hz, CHar), 116.44 (Cq), 61.10 (OCH$_3$), 15.43 (CH$_3$) ppm.

EI MS (70 eV, m/z (%): 310.1 ([M+], 21)

17.1.2. 2-fluoro-3-(trifluoromethyl)phenyl)(1-hydroxy-4-methoxy-3-methylnaphthalen-2-yl)methanone LJ118

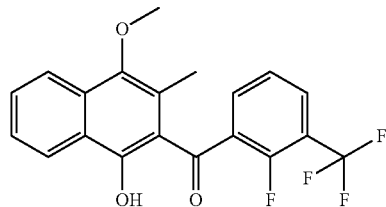 [SMILES: COc1c(C)c(C(=O)c2cccc(C(F)(F)F)c2F)c(O)c2ccccc12]

(1,4-dimethoxy-3-methylnaphthalen-2-yl)(2-fluoro-3-(trifluoromethyl)phenyl)methanone LJ116 (40 mg, 0.102 mmol) was used as a starting material and treated according to general procedure 12.1. The resulting dark yellow oil was purified through flash chromatography (Cyclohexane:EtOAc 10:1). The product was obtained as a bright yellow oil. Rf(Cyclohexane:EtOAc 10:1)=0.23. Yield=15 mg (38%).

$^{13}$C NMR (75 MHz, CDCl$_3$): δ=195.51 (C=O), 159.51 (Cq-O), 156.48 (dd, $^1J_{CF}$=262 Hz, $^3J_{CF}$=6 Hz, Cq-F), 146.99 (Cq-O), 133.47 (CHar), 132.22 (Cq), 131.56 (d, $^2J_{CF}$=14 Hz, Cq), 130.87 (CHar), 129.92 (CHar), 125.96 (CHar), 125.02 (CHar), 124.89 (Cq), 124.65 (CHar), 122.66 (Cq), 122.21 (q, $^1J_{CF}$=273 Hz, CF$_3$) 121.90 (CHar), 119.33 (dq, $^2J_{CF}$=33 Hz, Cq-CF$_3$) 116.08 (Cq), 61.09 (OCH$_3$), 15.51 (CH$_3$) ppm.

$^{19}$F NMR (282 MHz, CDCl$_3$): δ=−61.49 (d, $^4J_{FF}$=13 Hz, CF$_3$), −115.91 ($^4J_{FF}$=13 Hz, $^4J_{HF}$=6 Hz, F) ppm.

EI MS (70 eV, m/z (%): 378.3 ([M+], 48)

17.1.3. (2-fluoro-4-(trifluoromethyl)phenyl)(1-hydroxy-4-methoxy-3-methylnaphthalen-2-yl)methanone LJ130

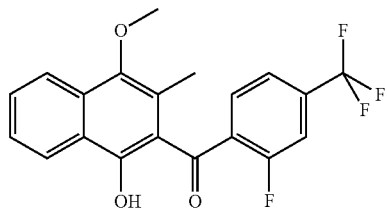 [SMILES: COc1c(C)c(C(=O)c2ccc(C(F)(F)F)cc2F)c(O)c2ccccc12]

(1,4-dimethoxy-3-methylnaphthalen-2-yl)(2-fluoro-4-(trifluoromethyl) phenyl)methanone LJ123 (23 mg, 0.060 mmol) was used as a starting material and treated according to general procedure 12.1. The resulting yellow oil was purified through flash chromatography (DCM:Cyclohexane 1:1). The product was obtained as a yellow solid. Rf(DCM:Cyclohexane 1:1)=0.55. Yield=15 mg (68%).

$^1$H NMR (300 MHz, CDCl$_3$): δ=12.87 (OH), 8.48-8.50 (m, 1H), 8.00-8.03 (m, 1H), 7.69-7.74 (m, 1H), 7.52-7.63 (cm, 3H), 7.43-7.46 (m, 1H), 3.82 (s, 3H, OCH$_3$), 1.98 (s, 3H, CH$_3$) ppm.

$^{19}$F NMR (282 MHz, CDCl$_3$): δ=−63.01 (s, CF$_3$), −111.93 (dd, $^3J_{HF}$=10 Hz, $^4J_{HF}$=7 Hz, F) ppm.

EI MS (70 eV, m/z (%)): 378.0 ([M+], 100), 363.0 (52), 345.0 (35).

17.2. Double Demethylation

General Procedure:
The general procedure followed the process for preparation of the following compound.

17.2.1. (1,4-dihydroxy-3-methylnaphthalen-2-yl)(2-fluoro-4-(trifluoromethyl) phenyl)methanone LJ139

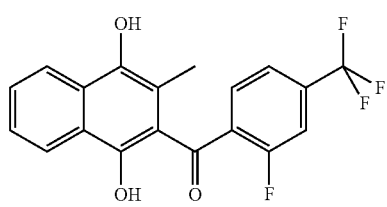 [SMILES: Cc1c(C(=O)c2ccc(C(F)(F)F)cc2F)c(O)c2ccccc2c1O]

(1,4-dimethoxy-3-methylnaphthalen-2-yl)(2-fluoro-4-(trifluoromethyl)phenyl)methanone LJ123 (250 mg, 0.64 mmol) dissolved in 40 mL DCM was cooled to 0° C. and kept stirring for 30 min. Pure BBr$_3$ (122 μL, 1.27 mmol, 2.0 equiv.) was added dropwise to the solution and the reaction mixture was stirred at 0° C. for 1 h. The reaction mixture was quenched with 60 mL MeOH. Saturated NaCl was added to the mixture and it was extracted with DCM (2×50 mL). The organic layer wad dried over MgSO$_4$ and evaporated to give 300 mg of a red-orange solid. The red-orange residue was recrystallised in 10 mL of a 10:1 Cyclohexane:EtOAc mixture. The product was obtained as bright orange crystals. Yield=220 mg (94%).

m.p. 104° C. (dec.)

$^1$H NMR (300 MHz, CDCl$_3$): δ=12.55 (s, 1H, OH), 8.46-8.49 (m, 1H), 8.06-8.09 (m, 1H), 7.69-7.74 (cm, 1H), 7.51-7.62 (cm, 3H), 7.42-7.46 (m, 1H), 4.68 (s, 1H, OH), 1.94 (s, 3H, CH$_3$) ppm.

$^{13}$C NMR (75 MHz, CDCl$_3$): δ=194.45 (C=O), 161.87 (Cq-OH), 159.31 (Cq-OH), 147.61 (d, $^1J_{CF}$=300 Hz, Cq-F), 144.79 (Cq), 143.80 (Cq), 134.15 (dq, $^2J_{CF}$=33 Hz, $^3J_{CF}$=9 Hz, Cq-CF$_3$), 132.68 (CHar), 131.76 (Cq), 127.93 (Cq), 127.19 (CHar), 125.45 (CHar), 124.98 (d, $^2J_{CF}$=23 Hz, Cq), 122.85 (CHar), 122.71 (CHar), 122.10 (CHar), 116.28 (Cq), 114.89 (dd, $^2J_{CF}$=25 Hz, $^3J_{CF}$=4 Hz, CHar), 13.76 (CH$_3$) ppm.

$^{19}$F NMR (CDCl$_3$, 282 MHz): δ=−63.44 (s, CF$_3$), −111.44 (dd, $^3J_{HF}$=10 Hz, $^4J_{HF}$=7 Hz, F) ppm.

EI MS (70 eV, m/z (%)): 364.1 ([M+], 100)

EA calcd for C$_{19}$H$_{12}$O$_3$F$_4$ (%): C, 62.64; H, 3.32; O, 13.18. Found: C, 62.20; H, 3.08.

17.3. Access to Benzoxanthones by Intramolecular Cyclization

General Procedure: The benzophenone derivative (1.0 equiv.) and K$_2$CO$_3$ (2.0 equiv.) were placed in a round-bottom flask. The flask was sealed under Argon and 10 mL of dry Acetone were added. The reaction mixture was stirred at 50° C. for 2 h. The suspension was then filtered through a pad of celite and washed with 25 mL Et$_2$O. The filtrate was concentrated under vacuo. The resulting product was purified through flash chromatography.

17.3.1. 5-methoxy-6-methyl-7H-benzo[c]xanthen-7-one LJ115

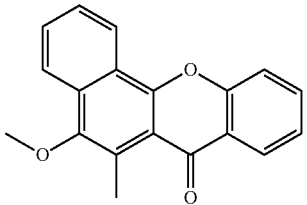 [SMILES: COc1c(C)c2c(=O)c3ccccc3oc2c2ccccc12]

(2-fluorophenyl)(1-hydroxy-4-methoxy-3-methylnaphthalen-2-yl)methanone LJ103 (150 mg. 0.483 mmol) was used as a starting material and treated according to general procedure 12.3. The product was obtained as an orange powder. Rf(Cyclohexane:EtOAc 10:1)=0.36. Yield=96 mg (69%).

$^1$H NMR (300 MHz, CDCl$_3$): δ=8.61-8.64 (m, 1H), 8.31-8.34 (m, 1H), 8.13-8.16 (m, 1H), 7.69-7.75 (m, 2H), 7.58-7.65 (m, 2H), 7.37-7.42 (cm, 1H), 3.91 (s, 3H, OCH$_3$), 2.96 (s, 3H, CH$_3$) ppm.

$^{13}$C NMR (75 MHz, CDCl$_3$): δ=178.68 (C=O), 154.81 (Cq-O), 151.84 (Cq-O), 149.81 (Cq-O), 133.93 (CHar), 130.99 (Cq), 129.87 (CHar), 126.57 (CHar), 126.29 (CHar), 125.86 (Cq), 124.22 (CHar), 123.79 (Cq), 123.28 (CHar), 123.21 (Cq), 122.17 (CHar), 117.46 (CHar), 117.35 (Cq), 61.45 (OCH$_3$), 14.51 (CH$_3$) ppm.

EI MS (70 eV, m/z (%)): 290.1 ([M+], 53)

EA calcd for C$_{19}$H$_{14}$O$_3$ (%): C, 78.61; H, 4.86; O, 16.53. Found: C, 78.81; H, 4.92.

Mp=175-177° C.

17.3.2. 5-methoxy-6-methyl-11-(trifluoromethyl)-7H-benzo[c]xanthen-7-one LJ119

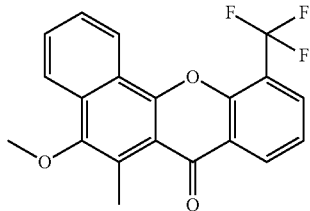 [SMILES: COc1c(C)c2c(=O)c3cccc(C(F)(F)F)c3oc2c2ccccc12]

(2-fluoro-3-(trifluoromethyl)phenyl)(1-hydroxy-4-methoxy-3-methylnaphthalen-2-yl)methanone LJ118 (15 mg. 0.040 mmol) was used as a starting material and treated according to general procedure 12.3. The product was obtained as a light yellow cotton-like solid.

Yield=12 mg (86%).

$^1$H NMR (300 MHz, CDCl$_3$): δ=8.66-8.68 (m, 1H), 8.54-8.57 (m, 1H), 8.17-8.20 (m, 1H), 8.02-8.05 (m, 1H), 7.76-7.82 (cm, 1H), 7.67-7.73 (cm, 1H), 7.47-7.53 (cm, 1), 3.92 (s. 3H. OCH$_3$), 2.97 (s. 3H. CH$_3$) ppm.

$^{13}$C NMR (75 MHz, CDCl$_3$): δ=177.39 (C=O), 151.79 (Cq-O), 151.52 (Cq-O), 150.50 (Cq-O), 131.27 (q. $^3J_{CF}$=4 Hz. CHar), 130.99 (CHar), 130.30 (CHar), 126.92 (CHar), 125.56 (Cq), 124.05 (Cq), 123.70 (Cq), 123.49 (CHar), 123.34 (CHar), 123.13 (q. $^1J_{CF}$=273 Hz. CF$_3$), 122.15 (CHar), 119.70 (Cq), 119.08 (q. $^2J_{CF}$=32 Hz. Cq-CF$_3$), 117.32 (Cq), 61.54 (OCH$_3$), 14.46 (CH$_3$) ppm.

$^{19}$F NMR (282 MHz, CDCl$_3$): δ=−61.31 (s, CF$_3$)

EI MS (70 eV, m/z (%)): 358.0 ([M+], 60), 343.0 (100).

EA calcd for C$_{20}$H$_{13}$O$_3$F$_3$ (%): C, 67.04; H, 3.66; O, 13.40. Found: C, 66.95; H, 3.80.

Mp=198-200° C.

17.3.3. 5-methoxy-6-methyl-10-(trifluoromethyl)-7H-benzo[c]xanthen-7-one LJ128

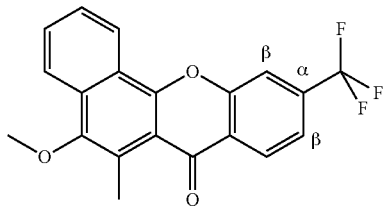 [SMILES: COc1c(C)c2c(=O)c3ccc(C(F)(F)F)cc3oc2c2ccccc12]

(2-fluoro-4-(trifluoromethyl)phenyl)(1-hydroxy-4-methoxy-3-methylnaphthalen-2-yl)methanone LJ130 (15 mg. 0.040 mmol) was used as a starting material and treated according to general procedure 12.3. The product was obtained as a white cotton-like solid. Rf(DCM:Cyclohexane 1:1)=0.37. Yield=11 mg (79%).

$^1$H NMR (300 MHz, CDCl$_3$): δ=8.66-8.69 (m, 1H), 8.46-8.49 (m, 1H), 8.18-8.21 (m, 1H), 7.96 (s, 1H), 7.77-7.82 (cm, 1H), 7.64-7.72 (m, 2H), 3.93 (s, 3H, OCH$_3$), 2.96 (s, 3H, CH$_3$) ppm.

$^{13}$C NMR (75 MHz, CDCl$_3$): δ=177.66 (C=O), 154.23 (Cq-O), 152.02 (Cq-O), 150.33 (Cq-O), 135.40 (q. $^2J_{CF}$=33 Hz. Cq-CF$_3$), 131.25 (Cq), 130.27 (CHar), 127.94 (CHar), 126.64 (CHar), 125.71 (Cq), 125.20 (Cq), 123.53 (Cq), 123.28 (q. $^1J_{CF}$=273 Hz. CF$_3$), 123.18 (CHar), 122.30 (CHar), 120.53 (q. $^3J_{CF}$=4 Hz. CHar), 117.53 (Cq), 115.47 (q. $^3J_{CF}$=4 Hz. CHar), 61.48 (OCH$_3$), 14.46 (CH$_3$) ppm.

$^{19}$F NMR (CDCl$_3$, 282 MHz): δ=−62.95 (s, CF$_3$)

EI MS (70 eV, m/z (%)): 358.0 ([M+], 53)

EA calcd for C$_{20}$H$_{13}$O$_3$F$_3$ (%): C, 67.04; H. 3.66; O, 13.40; F, 15.91. Found: C, 66.64; H, 3.81.

Mp=167-169° C.

17.3.4. 5-hydroxy-6-methyl-10-(trifluoromethyl)-7H-benzo[c]xanthen-7-one LJ144

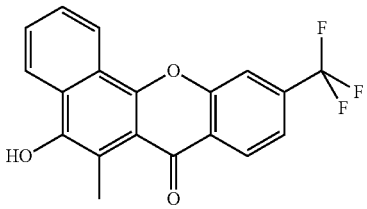 [SMILES: Cc1c(O)c2ccccc2c2oc3cc(C(F)(F)F)ccc3c(=O)c12]

(1,4-dihydroxy-3-methylnaphthalen-2-yl)(2-fluoro-4-(trifluoromethyl)phenyl) methanone LJ139 (100 mg. 0.275 mmol) was used as a starting material and treated according to general procedure 12.3. The resulting red-orange solid (90 mg) was recrystallised in 5 mL of a 10:1:0.1 Cyclohexane: EtOAc:Acetone mixture. The product was obtained as a bright yellow powder. Yield=60 mg (63%).

$^1$H NMR (300 MHz, CDCl$_3$): δ=8.64-8.67 (m, 1H). 8.46-8.48 (m, 1H). 8.28-8.31 (m, 1H). 7.95 (s, 1H). 7.63-7.81 (m, 3H). 5.33 (s, 1H, OH). 2.96 (s, 3H, CH$_3$) ppm.

$^{13}$C NMR (75 MHz, DMSO-d$^6$): δ=176.89 (C=O), 153.76 (Cq-O), 148.98 (Cq-O), 146.30 (Cq-O), 133.48 (Cq-CF$_3$), 126.87 (q, $^1J_{CF}$=273 Hz, CF$_3$), 129.68 (CHar), 127.58, (CHar), 126.61 (CHar), 125.20 (Cq), 122.74 (CHar), 122.39 (Cq), 122.32 (Cq), 121.58 (Cq), 120.12 (CHar), 116.94 (Cq), 116.09 (Cq), 115.93 (CHar), 13.76 (CH$_3$) ppm.

$^{19}$F NMR (CDCl$_3$, 282 MHz): δ=−63.03 (s, CF$_3$) ppm.

EI MS (70 eV, m/z (%)): 344.0 ([M+], 100)

EA calcd for C$_{19}$H$_{11}$O$_3$F$_3$ (%): C, 66.28%; H, 3.22%; O, 13.94%; F, 16.55%. Found: C, 66.23%; H, 3.58%.

Mp=229-231° C.

EXAMPLE 18

Inhibition of the Hematin Polymerisation

18.1. Material and Method

The antischistosomial effect is measured by the evaluation of the ability of the compounds to inhibit hematin polymerization according to the biochemical assay previously developed by Ncokazi. K. K. Egan. T. J. *Anal. Biochem.* 2005, 338, 306-319 adapted to the compounds of the present invention. The assays were monitored by UV-Vis absorption spectrophotometry and IC$_{50}$ values for inhibition of β-hematin formation were determined from the absorbance at 405 nm versus the drug (equiv.)/hematin (equiv.) ratio.

18.2. Results

They are given in the table below:

| Compound | Structure | Maximum inhibition (%) | IC$_{50}$ drug (equiv.)/ hematin (equiv.) ratio |
|---|---|---|---|
| LJ186 | 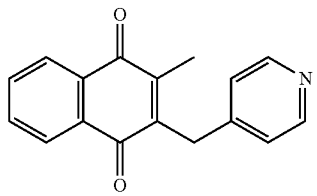 [SMILES: CC1=C(Cc2ccncc2)C(=O)c2ccccc2C1=O] | 80 | 4.2 |
| LJ144K | 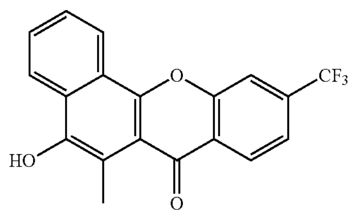 [SMILES: Cc1c(O)c2ccccc2c2oc3cc(C(F)(F)F)ccc3c(=O)c12] | 75 | 2.5 |

The two compounds LJ83K (=PTM58) and LJ186 are very potent inhibitors of the β-hematin polymerization. Both 3-benzylnaphtoquinone derivatives form 1:2 or 2:1 complexes with hematin displaying apparent association constants at pH 7.5 of about $10^{11}$-$10^{13}$ M$^{-1}$. Also the benzoxanthone derivative LJ144K form 1:1 charge-transfer complexes with hematin displaying apparent association constants at pH 7.5 of about $10^{5}$-$10^{6}$ M$^{-1}$. These thermodynamic values are comparable to those reported in the literature for antiparasitic xanthones targeting hematin polymerization (Monti. D., Vodopivec. B., Basilico. N., Olliaro. P., Taramelli. D. *Biochemistry* 1999, 38, 8858-8863).

EXAMPLE 19

Effect Against *P. falciparum* Strains 19.1. Material and Methods

The library of representative compounds was tested for antimalarial effects using the $^3$H-hypoxanthine incorporation-based assay (FIG. 1). Inhibition of the growth of *P. falciparum* by the compounds was evaluated by determining the inhibitor concentration required for killing 50% of the parasite (IC$_{50}$ values). In a screening assay all compounds were tested against the CQ-resistant *P. falciparum* strain Dd2.

In Vitro Antiparasitic Bioassays.

*P. falciparum* in vitro culture was carried out using standard protocols (Trager, W.; Jensen, J. B. *Science* 1976, 193, 673-675) with modifications (Friebolin, W.; Jannack, B.; Wenzel, N.; Furrer, J.; Oeser, T.; Sanchez, C. P.; Lanzer, M.; Yardley, V.; Becker, K.; Davioud-Charvet, E. *J. Med. Chem.* 2008, 51, 1260-1277). Drug susceptibility of *P. falciparum* was studied using a modified method (O'Brien, J.; Wilson, I.; Orton, T.; Pognan, F. *Eur. J. Biochem.* 2000, 267, 5421-5426) of the protocol described previously for the $^3$H-hypoxanthine incorporation-based assay (Desjardins, R. E.; Canfield, C. J.; Haynes, J. D.; Chulay, J. D. *Antimicrob. Agents Chemother.* 1979, 16, 710-718). All assays included CQ diphosphate (Sigma, UK) as standard and control wells with untreated infected and uninfected erythrocytes. IC$_{50}$ values were derived by sigmoidal regression analysis (Microsoft x/fit™)

Determination of IC$_{50}$ Values Against Dd2 *P. falciparum* Strain.

The IC$_{50}$ was tested by standard in vitro antiproliferation assays based on the $^3$H-hypoxanthine incorporation. Infected erythrocytes in ring stage (0.5% parasitemia, 2.5% hematocrit) in 96-well plates were exposed to the compounds for 48 h and then to radioactive hypoxanthine for 24 h. The amount of radioactivity in precipitable material served as an index of cell proliferation. Chloroquine was added as reference and displayed an IC$_{50}$ value of 110 nM.

19.2. Results

They are given in FIG. 1. The most effective compounds in killing *Plasmodium falciparum* are the 6- and 7-substituted naphthoquinones, in particular the 6- and the 7-fluoro menadione analogues, DAL54 and EC060, of the lead compounds P_TM24 or P_TM29, and the pyridinyl-4-methyl-substituted menadione LJ186. These compounds were found more active than chloroquine or as active as P_TM29 in assays using the multi-resistant *P. falciparum* strain Dd2. Using the Kochi-Anderson reaction from structurally diverse phenyl acetic acids, 4-pyridylacetic acid and polysubstituted menadiones, synthesized according the present processes of preparation, the preparation of various 3-benzyl menadiones derivatives, substituted at 6- and 7- of the menadione core, and pyridinyl-4-methyl-substituted menadione LJ186 analogues was applied.

Also, new azanaphthoquinones were constructed from Diels-Alder reaction and various aza-analogues were prepared and tested as antimalarial agents in assays using the multi-resistant *P. falciparum* strain Dd2. While various 6-methyl-7-(substituted-benzyl)quinoline-5,8-dione with structures disclosed in the international application WO 2009/118327 were tested and used as references in the antimalarial assays new aza analogues, exemplified by 7-methyl-6-(substituted-benzyl)quinoline-5,8-dione derivatives, were also produced following the two-step sequence—Diels-Alder reaction and then Kochi-Anderson reaction—and tested in the antimalarial assays.

Finally, putative metabolites of the antiparasitic (substituted-benzyl)menadione and (substituted-benzyl)azamenadione derivatives, generated from a cascade of redox reactions (FIG. 2), were synthesized. They are illustrated with the benzoyl-naphthoquinones and benzxanthones. They were tested in assays using the chloroquine-sensitive *P. falciparum* strain 3D7. The potential metabolite LJ144K was found to display significant antimalarial effects with $IC_{50}$ values in submicromolar range. The methylated precursors did not show antimalarial effects in the same range.

EXAMPLE 20

Effect Against *S. mansoni* Worms 20.1. Material and Methods

The compounds were tested to determine whether they could affect the survival of axenically cultured adult *S. mansoni* worms. Adult *S. mansoni* worms were cultured in the presence of different concentrations of the inhibitors and mobility and parasite death were monitored. Two groups were used for each compound: one is drug alone, and the other is drug+human RBCs (10 μl/well) or +10 μM hemoglobin (Hb). The final concentrations of compounds were 50 μM.

In Vitro Drug Treatments:

Compounds were dissolved in dimethylsulfoxide (DMSO) and added at concentrations indicated to freshly perfused worms in RPMI1640 containing 25 mM Hepes, pH 7, 150 units/ml penicillin, 125 μg/ml streptomycin, and 10% fetal calf serum (Cell Grow, Fisher). Media were replaced every two days with fresh media with addition of the compounds at the designated concentrations. Control worms were treated with equal amounts of DMSO alone. Worms were subsequently observed for motility and mortality and collected at the indicated times for analysis.

In Vivo Drug Treatments:

Compound LJ83K was dissolved in DMSO and administrated by intraperitoneal injection to *S. mansoni* infected-mice (NIH-Swiss, National Cancer Institute) at 33 mg/kg once a day for 2 consecutive days following the schedule in FIG. 5. Compound LJ83K at this dosage has been shown to be well tolerated by mice. Control *S. mansoni*-infected mice were administrated a corresponding amount of the drug carrier on the same timetable. Age-matched uninfected mice were used as reference group.

Enzyme Assays:

Enzyme preparation and assays were as described as described (Kuntz A N, Davioud-Charvet E, Sayed A A, Califf L L, Dessolin J, Arnér E S, Williams D L. Thioredoxin glutathione reductase from *Schistosoma mansoni*: an essential parasite enzyme and a key drug target. PLoS Med. 2007 June; 4(6):e206) with 15 nM TGR at 25° C. in 0.1 M potassium phosphate, pH 7.4, 10 mM EDTA. Thioredoxin reductase activity of TGR was determined using either 3 mM 5,5'-dithiobis(2-nitrobenzoic acid) (DTNB, Ellman's reagent) or 10 μM recombinant 6-histidine tagged *S. mansoni* thioredoxin-2 (DLW and al., unpublished). One enzyme unit was defined as the NADPH-dependent production of 2 μmol of 2-nitro-5-thiobenzoic acid per minute using $\epsilon_{412}$ nm=13.6 mM$^{-1}$ cm$^{-1}$ or the consumption of 1 μmol of NADPH ($\epsilon_{340}$ nm=6.22 mM$^{-1}$ cm$^{-1}$) during the first three minutes. Glutathione reductase activity was determined with 100 μM GSH disulfide and 100 μM NADPH by measuring the decrease in $A_{340}$ nm due to consumption of NADPH ($\epsilon_{340}$ nm=6.22 mM$^{-1}$ cm$^{-1}$) during the first three minutes. Each assay was done in triplicate and each experiment was repeated three times.

20.2. Results

They are given in FIGS. 3 to 5.

Antiparasitic (substituted-benzyl)menadione and (substituted-benzyl)azamenadione derivatives, and their potential metabolites illustrated with the benzoyl-naphthoquinones and benzxanthones, were tested in assays using *Schistosoma mansoni* worms in culture. To stimulate the drug metabolism in the parasites the tests were carried out in the absence or in the presence of hemoglobin or red blood cells (RBC). In the presence or in the absence of RBCs, the two most active compounds, LJ83K (P_TM58) and LJ81K (P_TM60), exhibited killing effects on the parasites; the parasites developed a "hairy phenotype" with appearance of spicula on the tegument, 4 hours after treatment suggesting an important perturbation in the metabolism of the parasite (see FIG. 3). These schistosomicidal effects might be mediated via a prodrug effect through heme-catalyzed oxidation reactions, responsible for the release of metabolites including the 3-benzoyl-menadione derivatives acting as subversive substrates of the disulfide reductases, i.e. both glutathione reductases of the infected red blood cells, and the thioredoxin-glutathione reductase from schistosomes. In the in vivo experiments, all injections were ip: the first injection was carried out six weeks post-infection, the second was performed two days later. Perfusion was 7 days after the second injection date. LJ83K was injected twice at 33 mg/kg (FIG. 5). LJ83K administration resulted in a significant, ca. 60% reduction (P=0.031) in worm burdens.

For azamenadiones designed in order to increase the solubility of the final naphthoquinones and for compounds designed to increase the resistance to oxidative metabolism in the worms the mobility of worms is decreased (data not shown).

Among the polysubstituted P_TM29 analogues, DAL29-I135 and DAL48-I133 could kill the parasites but survival rates were ca 50% after 48 hours no significant difference in the survival rates was found between the presence of and the absence of RBCs. It should be noted however that DAL48-I33 treatment led to the worms to develop a hairy phenotype within 48 hours. DAL50-I137 killed the parasites and RBCs could increase its potency. DAL53-I141 could kill parasites (71% dead worms after 48 h) but no significant difference in the survival rates was found between the presence of and the absence of RBCs (FIG. 4). Furthermore, the 6-chloro analogue of P_TM29, EC050, exhibited the highest antischistosomal action against ex vivo *S. mansoni* worms with 100% death after 24 h.

The invention claimed is:

1. A method of treating a subject suffering from a blood-feeding parasite of genus *Eimeria*, *Babesia*, or *Schistosoma*, comprising administering to said subject an effective amount of a compound of formula (Ia):

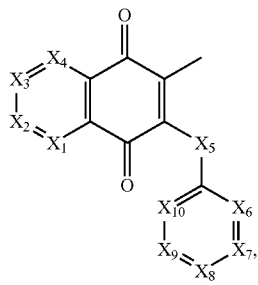

(Ia)

wherein:
each of $X_1$, $X_2$, $X_3$ and $X_4$ represents a carbon atom, or
either one of $X_1$, $X_2$, $X_3$ and $X_4$ represents a nitrogen atom, and each of the three others of $X_1$, $X_2$, $X_3$ and $X_4$ represents a carbon atom, or
each of $X_1$ and $X_4$ represents a nitrogen atom and each of $X_2$ and $X_3$ represents a carbon atom;
$X_5$ represents CO, $CH_2$ or CHOH;
each of $X_6$, $X_7$, $X_8$, $X_9$ and $X_{10}$ represents a carbon atom, or one of $X_6$, $X_7$, $X_8$, $X_9$ and $X_{10}$ represents a nitrogen atom and each of the four others of $X_6$, $X_7$, $X_8$, $X_9$ and $X_{10}$ represents a carbon atom;
$X_1$, $X_2$, $X_3$, and $X_4$, when they are carbon atoms optionally being substituted with
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$,
—$SCH_2F$,
a trifluoromethyl group, or
a trifluoromethoxy group, and
$X_6$, $X_7$, $X_8$, $X_9$, $X_{10}$, when they are carbon atoms optionally being substituted by
a hydrogen atom,
a halogen atom,
a hydroxy group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
a trifluoromethyl group,
a trifluoromethoxy group,
a difluoromethoxy group,
a difluoromethyl group,
COOH,
COO($C_1$-$C_4$) alkyl group,
$CONR_1(CH_2)_m CN$ with $R_1$ being a hydrogen atom or a linear or branched ($C_1$-$C_4$)alkyl group and m=1, 2 or 3,
$CSNR_1(CH_2)_m CN$ with $R_1$ being a hydrogen atom or a linear or branched ($C_1$-$C_4$)alkyl group m=1, 2 or 3,
$CONR_1$Het with $R_1$ being a hydrogen atom or a linear or branched ($C_1$-$C_4$) alkyl group and Het representing a pyridine-2-yl group, said pyridine-2-yl group optionally substituted by an amino group in -6 or by a —$CONH_2$ group in -5,
$NO_2$,
CN,
$NR_2R_3$ with $R_2$ and $R_3$ each independently representing a hydrogen atom, an amino protecting group that is a Boc group or a ($C_1$-$C_4$) alkyl group, or $R_2$ and $R_3$ forming with the nitrogen atom which bears them a cyclic group selected from the group consisting of morpholine, piperidine, and piperazine groups, said cyclic groups being optionally substituted,
an aryl group or an aryl group substituted by one or more substituents selected from the group consisting of a ($C_1$-$C_4$) alkyl group, a —$NO_2$ group, a —$COOR_4$ with $R_4$ being a hydrogen atom or a linear or branched ($C_1$-$C_4$) alkyl group, a —$NR_5R_6$ with $R_5$ and $R_6$ independently being a hydrogen atom or a linear or branched ($C_1$-$C_4$) alkyl group, or
a heterocyclic group selected from the group consisting of a morpholinyl group, a piperidinyl group, and a piperazinyl group, each of said heterocyclic groups being optionally substituted by one or more substituents selected from the group consisting of a linear or branched ($C_1$-$C_4$)alkyl group, —$COOCH_2CH_3$, and a

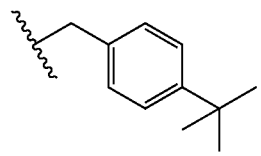 [SMILES: *Cc1ccc(C(C)(C)C)cc1]

group,
and pharmaceutically acceptable derivatives thereof.

2. A method of preventing or reducing the incidence of a parasitic disease due to blood-feeding parasites of genus *Eimeria, Babesia,* or *Schistosoma* in a subject, comprising administering to the subject an effective amount of a compound of formula (Ia):

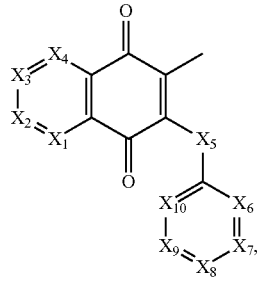

(Ia)

wherein:
each of $X_1$, $X_2$, $X_3$ and $X_4$ represents a carbon atom, or
either one of $X_1$, $X_2$, $X_3$ and $X_4$ represents a nitrogen atom, and each of the three others of $X_1$, $X_2$, $X_3$ and $X_4$ represents a carbon atom, or
each of $X_1$ and $X_4$ represents a nitrogen atom and each of $X_2$ and $X_3$ represents a carbon atom;
$X_5$ represents CO, $CH_2$ or CHOH;
each of $X_6$, $X_7$, $X_8$, $X_9$ and $X_{10}$ represents a carbon atom, or one of $X_6$, $X_7$, $X_8$, $X_9$ and $X_{10}$ represents a nitrogen atom and each of the four others of $X_6$, $X_7$, $X_8$, $X_9$ and $X_{10}$ represents a carbon atom;
$X_1$, $X_2$, $X_3$, and $X_4$, when they are carbon atoms optionally being substituted with a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$,
—$SCH_2F$,
a trifluoromethyl group, or
a trifluoromethoxy group, and $X_6, X_7, X_8, X_9, X_{10}$, when they are carbon atoms optionally being substituted by
a hydrogen atom,
a halogen atom,
a hydroxy group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
a trifluoromethyl group,
a trifluoromethoxy group,
a difluoromethoxy group,
a difluoromethyl group,
COOH,
COO ($C_1$-$C_4$) alkyl group,
$CONR_1(CH_2)_m CN$ with $R_1$ being a hydrogen atom or a linear or branched ($C_1$-$C_4$)alkyl group and m=1, 2 or 3,
$CSNR_1(CH_2)_m CN$ with $R_1$ being a hydrogen atom or a linear or branched ($C_1$-$C_4$)alkyl group m=1, 2 or 3,
$CONR_1$Het with $R_1$ being a hydrogen atom or a linear or branched ($C_1$-$C_4$) alkyl group and Het representing a pyridine-2-yl group, said pyridine-2-yl group optionally substituted by an amino group in -6 or by a —$CONH_2$ group in -5,
$NO_2$,
CN,
$NR_2R_3$ with $R_2$ and $R_3$ each independently representing a hydrogen atom, an amino protecting group that is a Boc group or a ($C_1$-$C_4$) alkyl group, or $R_2$ and $R_3$ forming with the nitrogen atom which bears them a cyclic group selected from the group consisting of morpholine, piperidine, and piperazine groups, said cyclic groups being optionally substituted,
an aryl group or an aryl group substituted by one or more substituents selected from the group consisting of a ($C_1$-$C_4$) alkyl group, a —$NO_2$ group, a —$COOR_4$ with $R_4$ being a hydrogen atom or a linear or branched ($C_1$-$C_4$) alkyl group, a —$NR_5R_6$ with $R_5$ and $R_6$ independently being a hydrogen atom or a linear or branched ($C_1$-$C_4$) alkyl group, or
a heterocyclic group selected from the group consisting of a morpholinyl group, a piperidinyl group, and a piperazinyl group, each of said heterocyclic groups being optionally substituted by one or more substituents selected from the group consisting of a linear or branched ($C_1$-$C_4$) alkyl group, —$COOCH_2CH_3$, and a

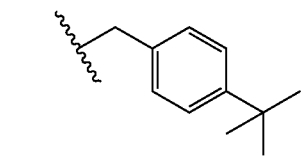 [SMILES: *Cc1ccc(C(C)(C)C)cc1]

group,
and pharmaceutically acceptable derivatives thereof.

3. The method according to claim 1, wherein the compound is selected from the group consisting of:

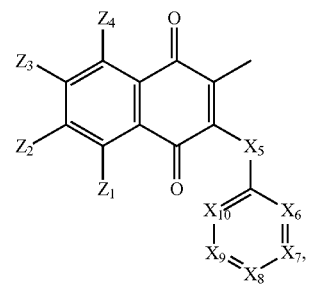

(Ia1)

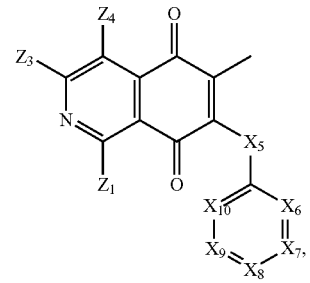

(Ia2)

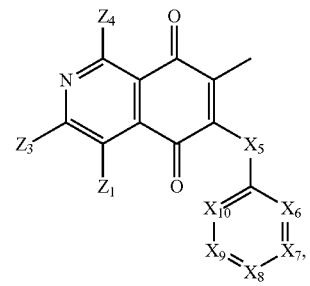

(Ia3)

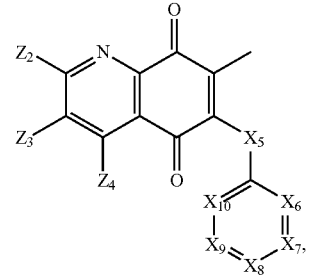

(Ia4)

(Ia5)

(Ia6)

wherein in each of Ia1, Ia2, Ia3, Ia4, Ia5 and Ia6: $Z_1$, $Z_2$, $Z_3$ and $Z_4$ each independently represents

- a hydrogen atom,
- a halogen atom,
- a hydroxy group,
- a triflate group,
- a phosphate group,
- a linear or branched ($C_1$-$C_4$)alkyl group,
- a linear or branched ($C_1$-$C_4$)alkoxy group,
- a thio($C_1$-$C_4$)alkoxy group,
- a pentafluorosulfanyl group,
- —$SCF_3$,
- —$SCH_2F$,
- a trifluoromethyl group, or
- a trifluoromethoxy group, and pharmaceutically acceptable derivatives thereof.

4. The method according to claim 2, wherein the compound is of a formula selected from the group consisting of:

(Ia1)

(Ia2)

(Ia3)

(Ia4)

(Ia5)

(Ia6)

wherein in each of Ia1, Ia2, Ia3, Ia4, Ia5 and Ia6: $Z_1$, $Z_2$, $Z_3$ and $Z_4$ each independently represents

- a hydrogen atom,
- a halogen atom,
- a hydroxy group,
- a triflate group,
- a phosphate group,
- a linear or branched ($C_1$-$C_4$)alkyl group, a linear or branched ($C_1$-$C_4$)alkoxy group,
a thio($C_1$-$C_4$)alkoxy group,
a pentafluorosulfanyl group,
—$SCF_3$
—$SCH_2F$,
a trifluoromethyl group, or
a trifluoromethoxy group;
and pharmaceutically acceptable derivatives thereof.

5. A method of treating a subject suffering from a parasitic disease due to *Plasmodium*, comprising administering to the subject an effective amount of a compound of formula (Ia):

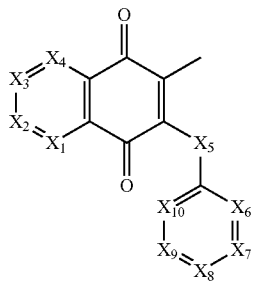

(Ia)

wherein
each of $X_1$, $X_2$, $X_3$ and $X_4$ represents a carbon atom, or
$X_1$ represents a carbon atom, one of $X_2$, $X_3$ and $X_4$ represents a nitrogen atom and each of the two others of $X_2$, $X_3$ and $X_4$ represents a carbon atom, or
$X_1$ represents a nitrogen atom and each of $X_2$, $X_3$ and $X_4$ represents a carbon atom, or
each of $X_1$ and $X_4$ represents a nitrogen atom and each of $X_2$ and $X_3$ represents a carbon atom,
$X_5$ represents CO, $CH_2$ or CHOH,
each of $X_6$, $X_7$, $X_8$, $X_9$ and $X_{10}$ represents a carbon atom, or one of $X_6$, $X_7$, $X_8$, $X_9$ and $X_{10}$ represents a nitrogen atom and each of the four others of $X_6$, $X_7$, $X_8$, $X_9$ and $X_{10}$ represents a carbon atom,
$X_1$, $X_2$, $X_3$, $X_4$, when they are carbon atoms optionally being substituted with,
a hydrogen atom,
a halogen atom,
a hydroxy group,
a triflate group,
a phosphate group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
—$SCF_3$,
—$SCH_2F$,
a trifluoromethyl group, or
a trifluoromethoxy group, and
$X_6$, $X_7$, $X_8$, $X_9$, $X_{10}$, when they are carbon atoms optionally being substituted with
a hydrogen atom,
a halogen atom,
a hydroxy group,
a linear or branched ($C_1$-$C_4$)alkyl group,
a linear or branched ($C_1$-$C_4$)alkoxy group,
a thio($C_1$-$C_4$)alkoxy group,
a pentafluorosulfanyl group,
a trifluoromethyl group,
a trifluoromethoxy group,
a difluoromethoxy group, a difluoromethyl group,
COOH,
COO ($C_1$-$C_4$) alkyl group,
$CONR_1(CH_2)_mCN$ with $R_1$ being a hydrogen atom or a linear or branched ($C_1$-$C_4$)alkyl group and m=1, 2 or 3,
$CSNR_1(CH_2)_mCN$ with $R_1$ being a hydrogen atom or a linear or branched ($C_1$-$C_4$)alkyl group m=1, 2 or 3,
$CONR_1$Het with $R_1$ being a hydrogen atom or a linear or branched ($C_1$-$C_4$) alkyl group and Het representing a pyridine-2-yl group, said pyridine-2-yl group optionally substituted by an amino group in -6 or by a —$CONH_2$ group in -5,
$NO_2$,
CN,
$NR_2R_3$ with $R_2$ and $R_3$ each independently representing a hydrogen atom, an amino protecting group that is a Boc group or a ($C_1$-$C_4$) alkyl group, or $R_2$ and $R_3$ forming with the nitrogen atom which bears them a cyclic group selected from the group consisting of morpholine, piperidine, and piperazine groups, said cyclic groups being optionally substituted,
an aryl group or an aryl group substituted by one or more substituents selected from the group consisting of a ($C_1$-$C_4$) alkyl group, a —$NO_2$ group, a —$COOR_4$ with $R_4$ being a hydrogen atom or a linear or branched ($C_1$-$C_4$) alkyl group, a —$NR_5R_6$ with $R_5$ and $R_6$ independently being a hydrogen atom or a linear or branched ($C_1$-$C_4$) alkyl group, or
a heterocyclic group selected from the group consisting of a morpholinyl group, a piperidinyl group, and a piperazinyl group, each of said heterocyclic groups being optionally substituted by one or more substituents selected from the group consisting of a linear or branched ($C_1$-$C_4$)alkyl group, —$COOCH_2CH_3$, and a

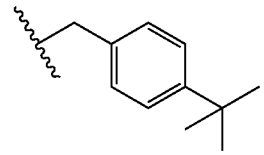 [SMILES: *Cc1ccc(C(C)(C)C)cc1]

group,
and pharmaceutically acceptable derivatives of the compound thereof,
with the proviso that: if each of $X_1$, $X_2$, $X_3$ and $X_4$ represents a carbon atom, or if $X_1$ represents a nitrogen atom, then at least one of $X_6$, $X_7$, $X_8$, $X_9$ and $X_{10}$ represents a nitrogen atom.

6. A method of preventing or reducing the incidence of a parasitic disease due to *Plasmodium* in a subject, comprising administering to the subject an effective amount of the compound of formula (Ia):

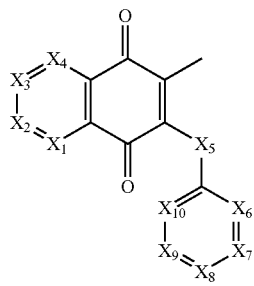

(Ia)

wherein
each of $X_1$, $X_2$, $X_3$ and $X_4$ represents a carbon atom, or
$X_1$ represents a carbon atom, one of $X_2$, $X_3$ and $X_4$ represents a nitrogen atom and each of the two others of $X_2$, $X_3$ and $X_4$ represents a carbon atom, or
$X_1$ represents a nitrogen atom and each of $X_2$, $X_3$ and $X_4$ represents a carbon atom, or
each of $X_1$ and $X_4$ represents a nitrogen atom and each of $X_2$ and $X_3$ represents a carbon atom,
$X_5$ represents CO, $CH_2$ or CHOH,
each of $X_6$, $X_7$, $X_8$, $X_9$ and $X_{10}$ represents a carbon atom, or one of $X_6$, $X_7$, $X_8$, $X_9$ and $X_{10}$ represents a nitrogen atom and each of the four others of $X_6$, $X_7$, $X_8$, $X_9$ and $X_{10}$ represents a carbon atom, and
when they are carbon atoms optionally being substituted with
a hydrogen atom,
a halogen atom,
a hydroxy group,
a triflate group,
a phosphate group,
a linear or branched $(C_1-C_4)$alkyl group,
a linear or branched $(C_1-C_4)$alkoxy group,
a thio$(C_1-C_4)$alkoxy group,
a pentafluorosulfanyl group,
—$SCF_3$,
—$SCH_2F$,
a trifluoromethyl group, or
a trifluoromethoxy group, and
$X_6$, $X_7$, $X_8$, $X_9$, $X_{10}$, when they are carbon atoms optionally being substituted with
a hydrogen atom,
a halogen atom,
a hydroxy group,
a linear or branched $(C_1-C_4)$alkyl group,
a linear or branched $(C_1-C_4)$alkoxy group,
a thio$(C_1-C_4)$alkoxy group,
a pentafluorosulfanyl group,
a trifluoromethyl group,
a trifluoromethoxy group,
a difluoromethoxy group,
a difluoromethyl group,
COOH,
COO $(C_1-C_4)$ alkyl group,
$CONR_1(CH_2)_mCN$ with $R_1$ being a hydrogen atom or a linear or branched $(C_1-C_4)$alkyl group and m=1, 2 or 3,
$CSNR_1(CH_2)_mCN$ with $R_1$ being a hydrogen atom or a linear or branched $(C_1-C_4)$alkyl group m=1, 2 or 3,
$CONR_1Het$ with $R_1$ being a hydrogen atom or a linear or branched $(C_1-C_4)$ alkyl group and Het representing a pyridine-2-yl group, said pyridine-2-yl group optionally substituted by an amino group in -6 or by a —$CONH_2$ group in -5,
$NO_2$,
CN,
$NR_2R_3$ with $R_2$ and $R_3$ each independently representing a hydrogen atom, an amino protecting group that is a Boc group or a $(C_1-C_4)$ alkyl group, or $R_2$ and $R_3$ forming with the nitrogen atom which bears them a cyclic group selected from the group consisting of morpholine, piperidine, and piperazine groups, said cyclic groups being optionally substituted,
an aryl group or an aryl group substituted by one or more substituents selected from the group consisting of a $(C_1-C_4)$ alkyl group, a —$NO_2$ group, a —$COOR_4$ with $R_4$ being a hydrogen atom or a linear or branched $(C_1-C_4)$ alkyl group, a —$NR_5R_6$ with $R_5$ and $R_6$ independently being a hydrogen atom or a linear or branched $(C_1-C_4)$ alkyl group, or
a heterocyclic group selected from the group consisting of a morpholinyl group, a piperidinyl group, and a piperazinyl group, each of said heterocyclic groups being optionally substituted by one or more substituents selected from the group consisting of a linear or branched $(C_1-C_4)$alkyl group, —$COOCH_2CH_3$, and a

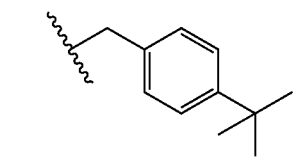 [SMILES: *Cc1ccc(C(C)(C)C)cc1]

group,
and pharmaceutically acceptable derivatives of the compound thereof,
with the proviso that: if each of $X_1$, $X_2$, $X_3$ and $X_4$ represents a carbon atom, or if $X_1$ represents a nitrogen atom, then at least one of $X_6$, $X_7$, $X_8$, $X_9$ and $X_{10}$ represents a nitrogen atom.

7. The method according to claim 5, wherein the compound is selected from the group consisting of:

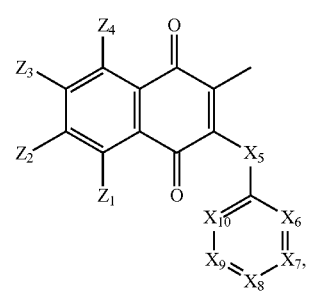

(Ia1)

-continued (Ia2)

(Ia3)

(Ia4)

(Ia5)

and (Ia6)

wherein in each of Ia1, Ia2, Ia3, Ia4, Ia5 and Ia6: $Z_1$, $Z_2$, $Z_3$ and $Z_4$ each independently represent,
  a hydrogen atom,
  a halogen atom,
  a hydroxy group,
  a triflate group,
  a phosphate group,
  a linear or branched ($C_1$-$C_4$)alkyl group, a linear or branched ($C_1$-$C_4$)alkoxy group, a thio($C_1$-$C_4$)alkoxy group, a pentafluorosulfanyl group,

—$SCF_3$

—$SCH_2F$, a trifluoromethyl group, or a trifluoromethoxy group, and pharmaceutically acceptable derivatives of the compound thereof, with the proviso that in the compound of formula (Ia1) and in the compound of formula (Ia6) at least one of $X_6$, $X_7$, $X_8$, $X_9$ and $X_{10}$ represents a nitrogen atom.

8. The method according to claim 6, wherein the compound is selected from the group consisting of:

(Ia1)

(Ia2)

(Ia3)

(Ia4)

-continued (Ia5)

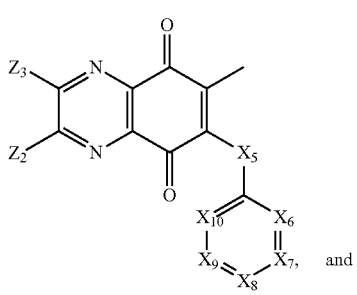

and (Ia6)

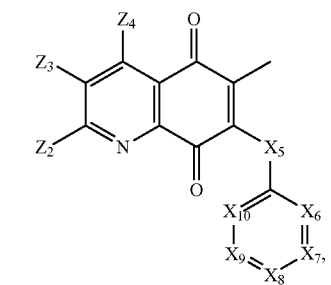

wherein $Z_1$, $Z_2$, $Z_3$ and $Z_4$ each independently represent,
- a hydrogen atom,
- a halogen atom,
- a hydroxy group,
- a triflate group,
- a phosphate group,
- a linear or branched ($C_1$-$C_4$)alkyl group,
- a linear or branched ($C_1$-$C_4$)alkoxy group,
- a thio($C_1$-$C_4$)alkoxy group,
- a pentafluorosulfanyl group,
- —$SCF_3$
- —$SCH_2F$,
- a trifluoromethyl group, or
- a trifluoromethoxy group,
- and pharmaceutically acceptable derivatives of the compound thereof,
- with the proviso that in the compound of formula (Ia1) and in the compound of formula (Ia6) one of $X_6$, $X_7$, $X_8$, $X_9$ and $X_{10}$ represents a nitrogen atom.

9. A method of treating a subject suffering from a parasitic disease due to *Plasmodium*, comprising administering to the subject an effective amount of at least one of the following compounds:

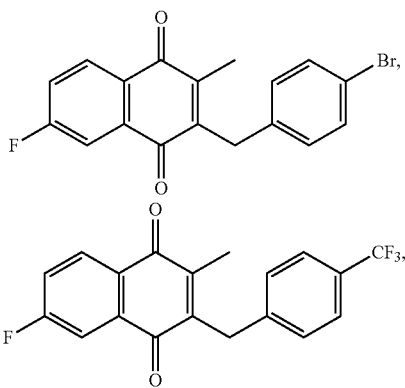

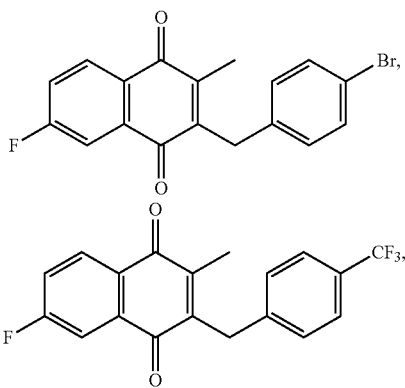

-continued

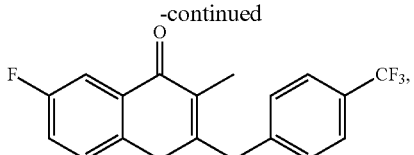

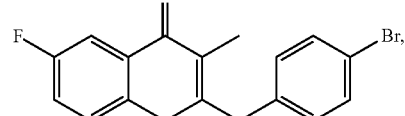

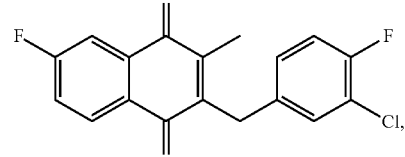

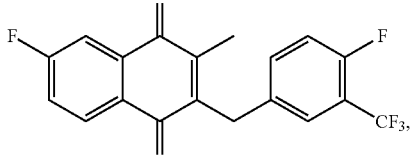

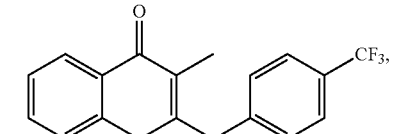

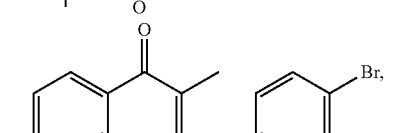

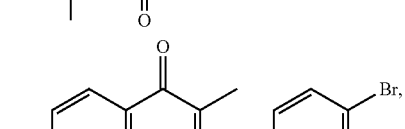

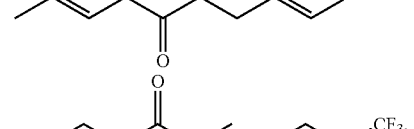

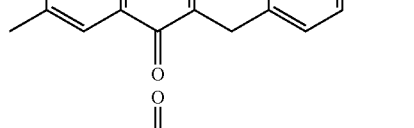

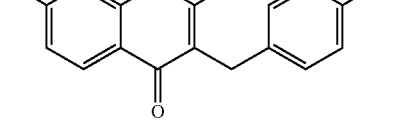

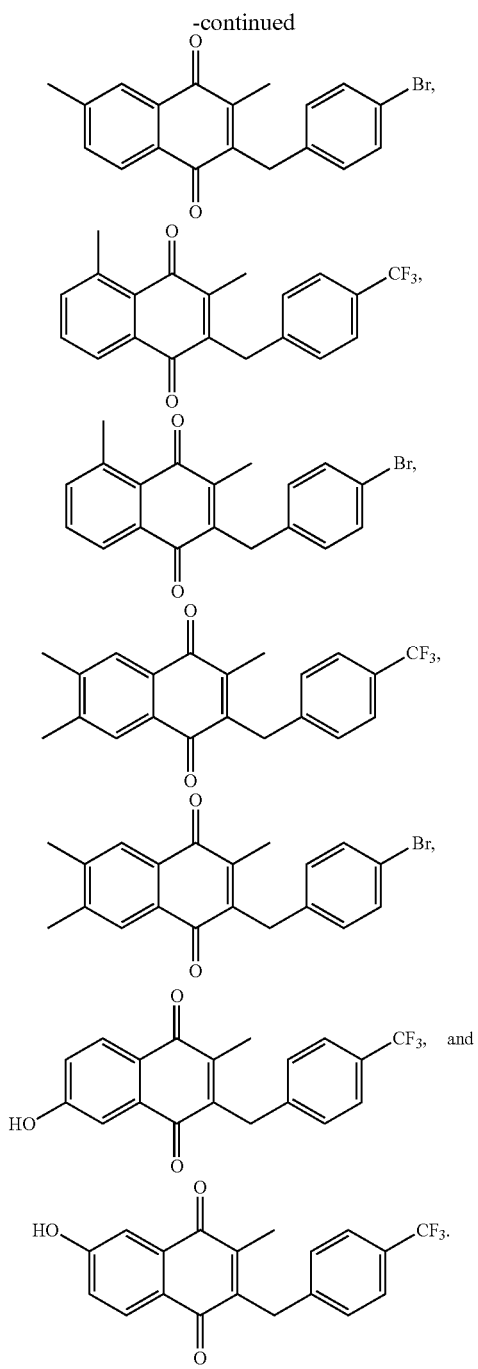
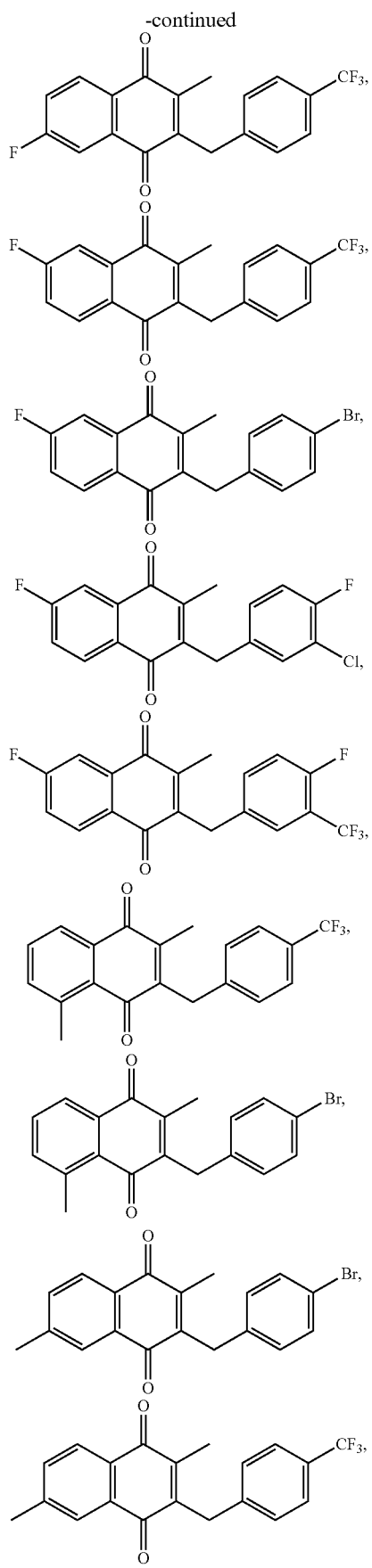
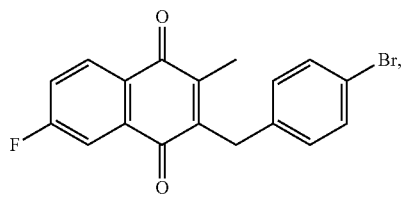
10. A method of preventing or reducing the incidence of a parasitic disease due to *Plasmodium* in a subject, comprising administering to the subject an effective amount of at least one of the following compounds:

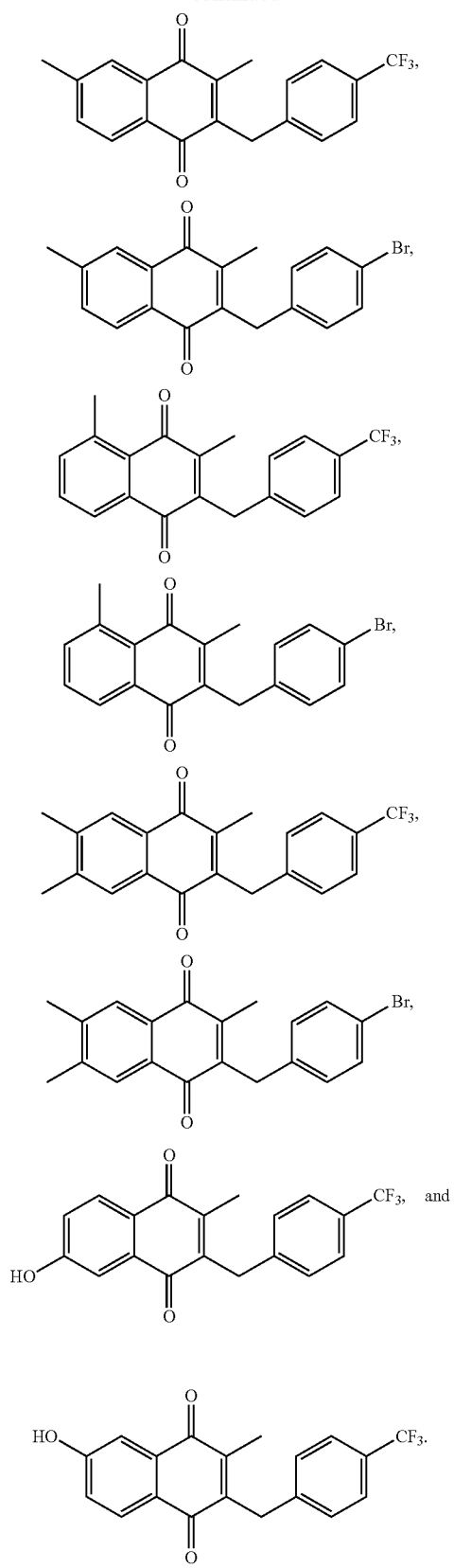
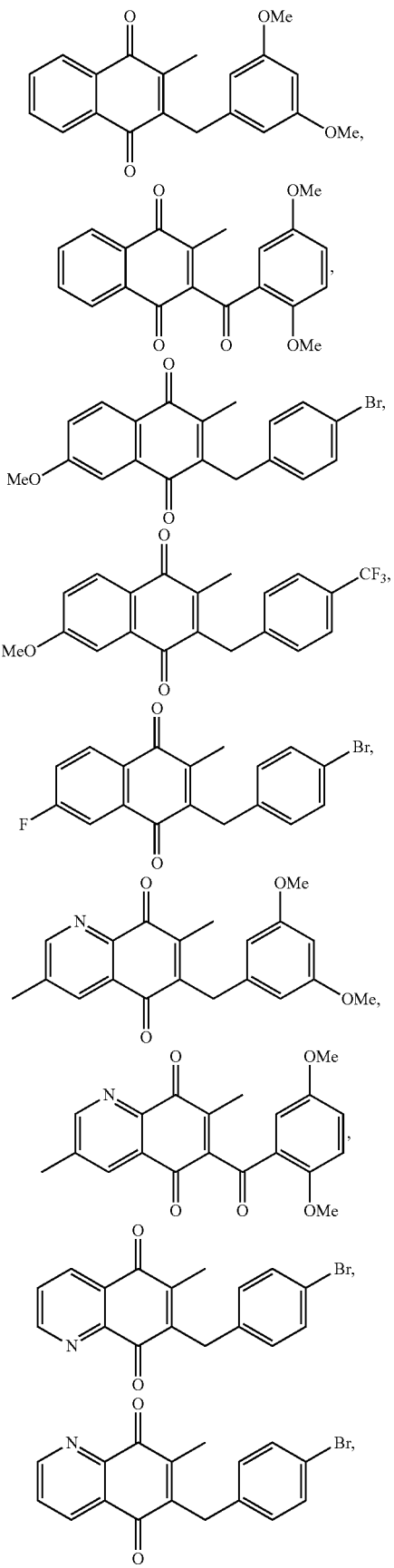
11. The method of claim 1, wherein the compound of formula (Ia) is selected from the group consisting of:

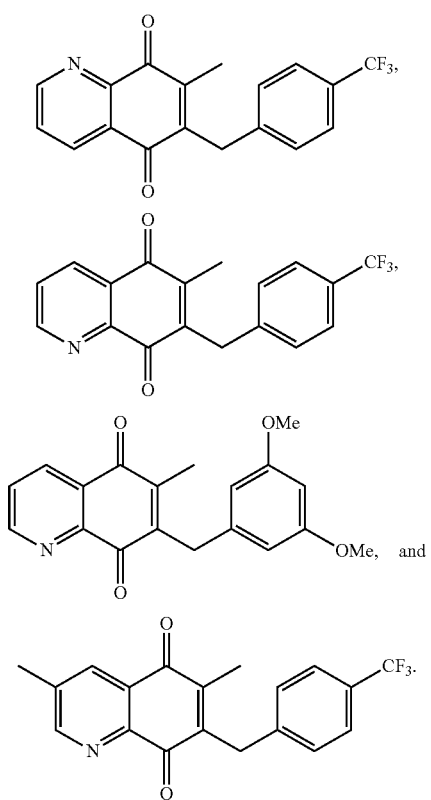
12. The method of claim 2, wherein the compound of formula (Ia) is selected from the group consisting of:
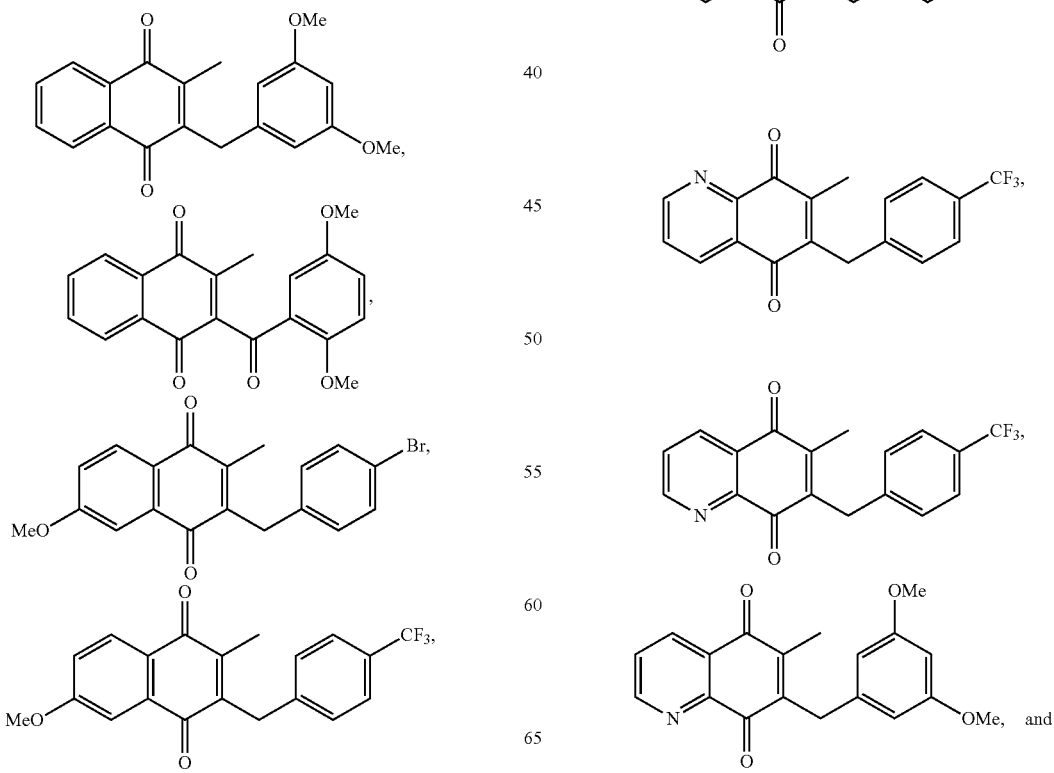
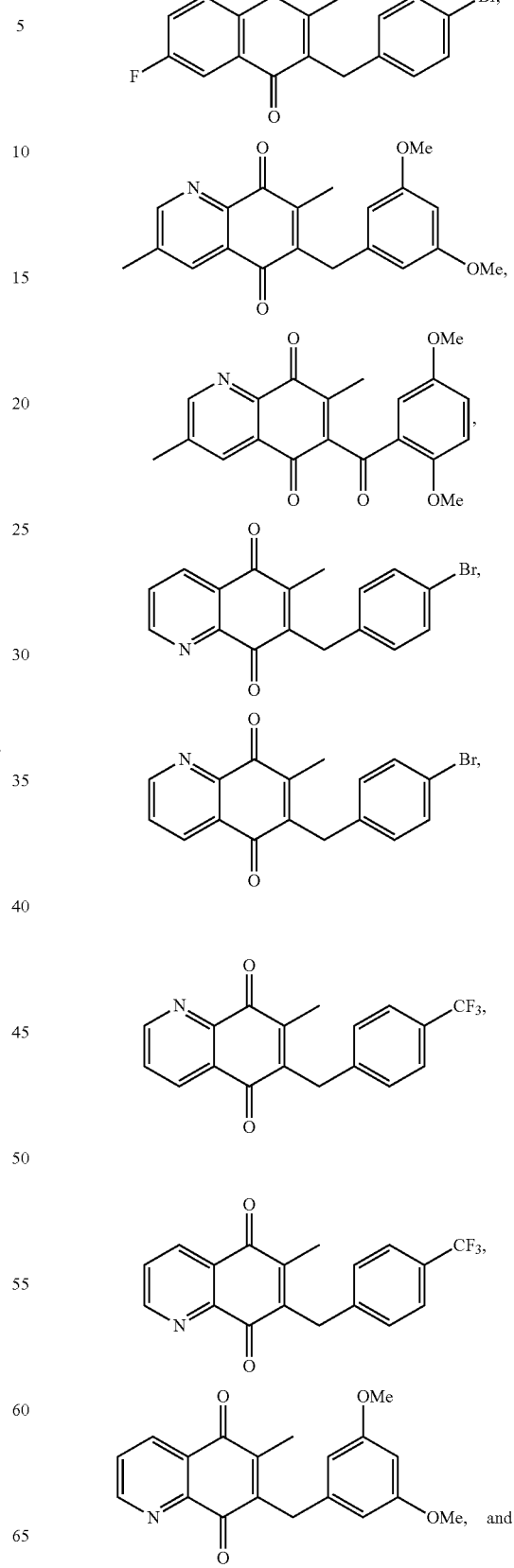

-continued
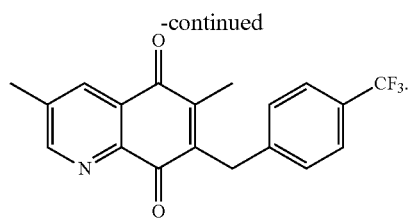
* * * * *